United States Patent
Copley et al.

(10) Patent No.: US 6,277,599 B1
(45) Date of Patent: Aug. 21, 2001

(54) ANTI-CEA ANTIBODY DESIGNATED 806.077, HYBRIDOMA AND METHOD OF MANUFACTURE

(75) Inventors: Clive Graham Copley; Michael Derek Edge; Stephen Charles Emery, all of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/171,945

(22) PCT Filed: Apr. 29, 1997

(86) PCT No.: PCT/GB97/01165

§ 371 Date: Oct. 29, 1998

§ 102(e) Date: Oct. 29, 1998

(87) PCT Pub. No.: WO97/42329

PCT Pub. Date: Nov. 13, 1997

(30) Foreign Application Priority Data

May 4, 1996 (GB) .................................. 9609405
Feb. 14, 1997 (GB) .................................. 9703103

(51) Int. Cl.$^7$ .................................. C12N 15/13
(52) U.S. Cl. .................. 435/69.6; 435/326; 435/328; 435/344.1; 530/387.3; 530/388.8; 530/388.85
(58) Field of Search ............... 530/387.1, 387.3, 530/388.1, 388.8, 388.85; 435/326, 328, 332, 344, 344.1, 69.6; 424/130.1, 155.1, 156.1, 157.1

(56) References Cited

FOREIGN PATENT DOCUMENTS

| 633029 | 10/1995 | (EP) . |
|---|---|---|
| WO 92/01059 | 1/1992 | (WO) . |
| WO 94/25585 | 11/1994 | (WO) . |
| WO 95/15341 | 6/1995 | (WO) . |
| WO 96/11013 | 4/1996 | (WO) . |

OTHER PUBLICATIONS

D. Blakey et al, "Anti–tumour effects of an antibody–carboxypeptidase G2 conjugate in combination with phenol mustard prodrugs.", *British Journal of Cancer*, Nov. 1995, pp. 1083–1088, vol. 72, No. 5, Basingstoke, GB.

M. Michael et al., "In vitro and in vivo characterization of a recombinant carboxypeptidase G2:anti–CEA scFv fusion protein," *Immunotechnology*, 1996, pp. 47–57, vol. 2, No. 1, Amsterdam, NL.

S. Leung et al., "Bacterial expression of a keptide fusion protein facilitates 32P labeling of a humanized, anti–carcinoembryonic antigen (hMN–14) antibody fragment," *Cancer Research*, Dec. 1, 1995, pp. 5968S–5972S, vol. 55, No. 23, suppl., Baltimore, MD, USA.

K. Bosslet et al., "Tumor–selective prodrug activation by fusion protein–mediated catalysis," *Cancer Research*, Apr. 1, 1994, pp. 2151–2159, vol. 54, No. 7, Baltimore, MD, USA.

Abraham, *Journal of Immunological Methods*, 183, 1995, pp. 119–125.

Accolla, *Proc. Natl. Acad. Sci.*, 77, 1980, pp. 563–566.

Banjo, *Cancer Research*, 34, Aug. 1974, pp. 2114–2121.

Chandrasekaran, *The Journal of Biological Chemistry*, 258, 1983, pp. 7213–7222.

Chournoyer, *Cancer Research*, 48, 1988, pp. 3153–3157.

Durbin, *Proc. Natl. Acad. Sci.*, 91, 1994, pp. 4313–4317.

Haggarty, *Cancer Research*, 46, 1986, pp. 300–309.

Hammarstrom, *Cancer Research*, 49, 1989, pp. 4852–4858.

Hansen, *Cancer*, 71, Jun. 1993, pp. 3478–3485.

Hedin, *Molecular Immunology*, 19, 1982, pp. 1641–1648.

Hefta, *Cancer Research*, 52, Oct. 1992, 5647–5655.

Konstadoulakis, *Journal of Clinical Immunology*, 14, 1994, pp. 310–313.

Kuroki, *Cancer Research*, 41, Feb. 1981, 713–718.

Kupchik, *Cancer Research*, 41, Sep. 1981, pp. 3306–3310.

Oikawa, *Biochemical and Biophysical Research Communications*, 142, 1987, pp. 511–518.

Rogers, *Br. J. Cancer*, 43, 1981, pp. 1–4.

Thomas, *Biochemical and Biophysical Research Commuications*, 188, 1992, pp. 671–677.

*Primary Examiner*—Sheela Huff
*Assistant Examiner*—Larry R. Helms
(74) *Attorney, Agent, or Firm*—Rothwell, Figg, Ernst & Manbeck

(57) ABSTRACT

An anti-CEA monoclonal antibody, designated 806.077, of murine origin is useful for the diagnosis and therapy of cancer. The antibody complementarity determining regions have the following sequences: heavy chain CDR1 DNYMH, CDR2 WIDPENGDTE YAPKFRG, CDR3 LIYAGYLAMD Y; and light chain CDR1 SASSSVTYMH, CDR2 STSNLAS, CDR3 QQRSTYPLT. The antibody optionally is humanized and can be in the form of a conjugate with either an enzyme, such as carboxypeptidase, or a co-stimulatory molecule such as the extracellular domain of human B7.1.

8 Claims, 3 Drawing Sheets

Single cut restriction enzymes
+ HindIII cuts twice
+ XmaI cuts three times
+ PstI cuts six times.

ANTI-CEA ANTIBODY DESIGNATED 806.077, HYBRIDOMA AND METHOD OF MANUFACTURE

This application is a § 371 national phase filing of PCT/GB97/01165, filed Apr. 29, 1997.

The present invention relates to a novel anti-CEA monoclonal antibody (named "806.077 antibody" or "806.077 Ab" herein) useful for the diagnosis and therapy of cancer.

It is established that the transformation of normal tissue cells to tumour cells is associated with a change in structure on the cell surface. Altered cell surface structures can serve as antigens and the tumour modified structures represent a type of so-called tumour-associated antigen (see for example Altered Glycosylation in Tumour Cells, Eds. Reading, Hakamori and Marcus 1988, Arthur R. Liss publ.). Such antigens may be exploited for example by the generation of monospecific antibodies using hybridoma technology as is presently well established after being first described by Kohler and Milstein (Nature, 256, 495–497, 1975).

One tumour-associated antigen is CEA (Carcinomembryonic Antigen) as first described by Gold and Freedman, J Exp Med, 121 439, 1965. This antigen is present on the tumour cell surface and can also be demonstrated in blood serum.

The concept of using antibodies to target tumour associated antigens in the treatment of cancer has been appreciated for some time (Herlyn et.al. (1980) Cancer Research 40 717). Antibodies may be used to target various chemical and biological agents to the tumour and such conjugates have been particularly successful in forming the basis for many methods of both in vitro and in vivo diagnosis. The use of immunoconjugates in the therapy of cancer is also promising (Lord et al.(1985) Trends in Biotechnology 3, 175; Vitetta et al (1987) Science 238, 1098). This approach is technically more demanding than diagnostic applications and requires that tumour associated antigens which are targetted in such immunotherapeutic approaches, are highly tumour specific and not expressed at significant levels in vital human tissues. Whilst not wishing to be bound by theoretical considerations, as well as the property of having specific tumour associated tissue distribution, for some applications it is desirable that the antibody remain at the cell surface after antigen binding rather than being quickly internalised. For example in ADEPT (antibody directed enzyme prodrug therapy, see U.S. Pat. Nos. 4,975,278 and 5,405,990) it is believed to be preferred that the antibody remain at the cell surface to facilitate prodrug activation by antibody-enzyme conjugate.

Antibody conjugates also have application in tumour immunotherapy. The following few paragraphs set out the scientific background for this application. In order to respond to an immune stimulus, T-cells require two signals. One such signal is provided by recognition of MHC displayed peptides by the T-cell receptor (TCR). It has been demonstrated however that TCR stimulation alone results in T-cell unresponsiveness or anergy and a second or co-stimulatory signal is required to stimulate specific T-cell activation and proliferation (reviewed by Schwartz R. H. J.Exp.Med., 1996, 184, 1–8). Upon receiving both signals, the resulting cytotoxic T-cells mediate the immune response by killing the target cells. A number of potential co-stimulatory molecules have been identified (eg B7, ICAMs, LFA-1 and 3, CD40, CD70 and CD24, reviewed by Galea-Lauri J. et al Cancer Gene Therapy, 1996, 3, 202–213). The major co-stimulatory function appears to be provided by the related molecules B7.1 (also called CD80) and B7.2 (also called CD86) which can interact with two receptors, CD28 and CTLA-4 (Hellstrom K. E. et al Immunol. Rev., 1995, 145, 123–145 and Lenschow D. J. et al Ann.Rev.Immunol., 1996, 14, 233–258). B7.1 and B7.2 are expressed on antigen presenting cells (APC) such as dendritic cells whereas CD28 and CTLA-4 are present on T-cells. B7.2 appears to be constitutively expressed on the surface of APCs but after contact with a T-cell, expression of B7.1 is up-regulated. Analogously, CD28 is expressed on T-cells but after activation is down-regulated and replaced by CTLA-4 expression. The stimulation of CD28 and CTLA-4 by B7.1 and B7.2 represents a complex pattern of signalling which controls not only the activation of the T-cell, but the subsequent control of proliferation to modulate the immune-response (Greene J. et al J.Biol.Chem., 1996, 271, 26762–26771). This phenomenon may explain the sometimes conflicting data reported by workers studying these co-stimulatory molecules.

In cancer, tumour infiltrating lymphocytes have been identified but the lack of immune-response to the tumour may be due to T-cell anergy. Tumour cells can display specific or selective antigens on their surface but lack B7.1/B7.2 allowing them to escape immune surveillance. Indeed, in vivo experiments have demonstrated that B7.1/B7.2 transfected tumour cells are less tumourigenic than untransfected cells from the same line and that the transfected cells are capable of inducing protective immunity against rechallenge with parental cells (Townsend S. E. and Allison J. P., 1993, Science, 259, 368–370). This demonstrates that once stimulated, the immune response can become B7.1/B7.2 independent. Hellstrom has proposed that expression of B7.1/B7.2 in tumour cells by gene therapy has the potential to stimulate a host reponse which can reduce or eliminate the disease. Gajewski (J.Immunol., 1996, 156, 465–472) and Matulonis et al (J.Immunol., 1996, 156, 1126–1131) have reported that B7.1 is superior to B7.2 in the activation of T-cells. The use of B7.1 in solution (as a fusion with antibody constant domains) is reported to provide only modest co-stimulation to T-cells receiving TCR stimulation via an independent source (Linsley P.S. et al J.Exp.Med., 1991, 173, 721–730).

There is a need for further and improved anti-CEA antibodies useful in cancer diagnosis and therapy.

The present invention is based on the discovery of a novel anti-CEA antibody termed 806.077 antibody herein.

According to one aspect of the present invention there is provided an anti-CEA antibody comprising complementarity determining regions (CDRs) in which the CDRs have the following sequences:

a) heavy chain
  CDR1 DNYMH (SEQ ID NO: 29)
  CDR2 WIDPENGDTE YAPKFRG (SEQ ID NO: 31)
  CDR3 LIYAGYLAMD Y(SEQ ID NO: 32);

b) light chain
  CDR1 SASSSVTYMH (SEQ ID NO: 26)
  CDR2 STSNLAS (SEQ ID NO: 27)
  CDR3 QQRSTYPLT (SEQ ID NO: 28).

The CDRs or complementarity determining regions are those sequences within the hypervariable loops of antibody variable domains which are believed to be critical in determining the specificity of the antigen-antibody interaction (Kabat, E. A., Lu, T. T., Reid-Miller, M., Perry, H. M. & Gottesman, K. S. (1987). Sequences of Proteins of Immunological Interest. 4th edition. Washington D.C.: United States Dept. of Health and Human Services; the reader is also referred to this reference for details of Kabat antibody residue numbering). CDRs a defined herein however include framework residues where these contribute to binding. For the 806.077 antibody the CDRs were determined by homology with the hypervariable sequences of other murine antibodies. In this specification the terms "VK" and "VH" mean variable regions of the light and heavy antibody chains respectively. Anatomy of the antibody molecule has been reviewed by Padlan (1994) in Molecular Immunology 31, 169–217.

The Light Chain CDRs are:
VK CDR1 Kabat residues 24–34 inclusive, SASSSVTYMH (SEQ ID NO: 26);
VK CDR2 Kabat residues 50–56 inclusive, STSNLAS (SEQ ID NO: 27);
VK CDR3 Kabat residues 89–97 inclusive, QQRSTYPLT (SEQ ID NO: 28);
The Heavy Chain CDRs are:
VH CDR1 Kabat residues 31–35B inclusive, DNYMH (SEQ ID NO: 29);
preferred VH CDR1 Kabat residues are no. 27–35B inclusive, FNIKDNYMH (SEQ ID NO: 30);
VH CDR2 Kabat residues 50–65 inclusive, WIDPENGDTE YAPKFRG (SEQ ID NO: 31)
VH CDR3 Kabat residues 95–102 inclusive, LIYAGYLAMD Y (SEQ ID NO: 32); and
preferred VH CDR3 Kabat residues are no. 93–102 inclusive, HVLIYAGYLA MDY (SEQ ID NO: 33).

Preferably binding affinity for CEA antigen is at least 10E-5M, more preferably binding affinity for CEA is at least 10E-6M, more preferably binding affinity for CEA is at least 10E-7M, more preferably binding affinity for CEA is at least 10E-8M, more preferably binding affinity for CEA is at least 10E-9M, more preferably binding affinity for CEA is at least 10E-10M and especially binding affinity for CEA is at least 10E-11M.

The term antibody as used herein generally means an immunoglobulin molecule (or fragment thereof or modified antibody construct such as scFv which retains specific CEA antigen binding). The CDRs are principally responsible for antigen binding, the non-CDR protein sequence is normally derived from an immunoglobulin but may be derived from immunoglobulin domain of a immunoglobulin super family member.

According to another aspect of the present invention there is provided a CEA antibody comprising the following, optionally humanised, structure:
a heavy chain variable region sequence (SEQ ID NO: 11)
EVQLQQSGAE LVRSGASVKL SCTASGFNIK DNYM-HWVKQR 40
PEQGLEWIAW IDPENGDTEY APKFRGKATL TADSSSNTAY 80
LHLSSLTSED TAVYYCHVLI YAGYLAMDYW GQGTS-VAVSS 120
and;
a light chain variable region sequence (SEQ ID NO: 9):
DIELTQSPAI MSASPGEKVT ITCSASSSVT YMHW-FQQKPG 40
TSPKLWIYST SNLASGVPAR FSGSGSGTSY SLTISRMEAE 80
DAATYYCQQR STYPLTFGAG TKLELKRA 108;
or any one of the following constructs thereof:
F(ab')$_2$; F(ab'), Fab, Fv, single chain Fv & V-min.

F(ab')$_2$ fragment constructs are preferred. Any suitable antibody fragment which retains 806.077 antibody binding characteristics is contemplated. For example a recently described antibody fragment is "L-F(ab)$_2$" as described by Zapata (1995) in Protein Engineering, 8, 1057–1062. Disulphide bonded Fvs are also contemplated. Optionally the antibody forms part of a conjugate as described below.

A preferred humanised antibody comprises at least one of the following sequences:
a heavy chain variable region sequence which is VH1 (SEQ ID NO: 55);
a light chain variable region sequence which is VK4 (SEQ ID NO: 71);
a human CH1 heavy chain IgG3 constant region;
a human kappa light chain CL region; and
a human IgG3 hinge region;
optionally in the form of a F(ab')$_2$ fragment.

According to another aspect of the present invention there is provided a polynucleotide sequence capable of encoding for the heavy or light chain variable region of a CEA antibody of the invention. Preferably the heavy or light chain variable region is fused (optionally via some linking sequence) to a gene encoding a protein effector moiety (as part of a conjugate, see text below), preferably fusion is through the antibody heavy chain. Generally fusion can be either at the N or C terminus of the antibody chain. For B7 conjugates fusion at the N-terminus of the antibody chain is preferred.

CPB has an N-terminal pro domain which is believed to assist correct folding of protein before the pro domain is removed to release active enzyme. If proCPB is fused at its C terminus to the N terminus of an antibody chain this allows removal of pro domain (e.g. by trypsin treatment) from the N terminus of the fusion construct. Alternatively if proCPB was attached to the C terminus of an antibody chain then the problem arises of having to remove the pro domain from the "middle" of the construct without destroying the fusion protein. The solution is to co-express the pro domain separately (in trans). This has the advantage, once the cell lines have been constructed, of not requiring trypsin activation of expressed fusion protein to remove CPB pro domain. Constructs with proCPB fused at its C terminus to the N terminus of an antibody chain have the advantage of not requiring construction of co-expression cell lines which require high level expression of the pro domain along -with high level expression of other proteins.

In this specification conservative amino acid analogues of specific amino acid sequences are contemplated which retain the binding properties of the CEA antibody of the invention but differ in sequence by one or more conservative amino acid substitutions, deletions or additions. However the specifically listed amino acid sequences are preferred. Typical conservative amino acid substitutions are tabulated below.

| Original | Conservative Substitutions | |
|---|---|---|
| | Exemplary Substitutions | Preferred Substitutions |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

-continued

Conservative Substitutions

| Original | Exemplary Substitutions | Preferred Substitutions |
|---|---|---|
| Met (M) | Leu; Phe; Ile | Leu |
| Phe (F) | Leu; Val; Ile; Ala | Leu |
| Pro (P) | Gly | Gly |
| Ser (S) | Thr | Thr |
| Thr (T) | Ser | Ser |
| Tyr (Y) | Trp; Phe; Thr; Ser | Phe |
| Val (V) | Ile; Leu; Met; Phe; Ala; Norleucine | Leu |

In this specification nucleic acid variations (deletions, substitutions and additions) of specific nucleic acid sequences are contemplated which retain which the ability to hybridise under stringent conditions to the specific sequence in question. A hybridisation test is set out in Example 9 hereinafter. However specifically listed nucleic acid sequences are preferred. It is contemplated that peptide nucleic acid may be an acceptable equivalent of polynucleotide sequences, at least for purposes that do not require translation into protein (Wittung (1994) Nature 368, 561).

According to another aspect of the present invention there is provided an antibody or antibody fragment as herein described characterised in that it is humanised.

A humanised antibody, related fragment or antibody binding structure is a polypeptide composed largely of a structural framework of human derived immunoglobulin sequences supporting non human derived amino acid sequences in and around the antigen binding site (complementarity determining regions or CDRs; this technique is known as CDR grafting which often involves some framework changes too, see the Examples below). Appropriate methodology has been described for example in detail in WO 91/09967, EP 0328404 and Queen et al. Proc Natl Acad Sci 86,10029, Mountain and Adair (1989) Biotechnology and Genetic Engineering Reviews 10, 1 (1992) although alternative methods of humanisation are also contemplated such as antibody veneering of surface residues (EP 519596, Merck/NIH, Padlan et al). Preferred humanised 806.077 antibodies are any one of Examples 11–47 or 107–122. A preferred humanised heavy chain variable region is VH1 (see Examples). A preferred light chain variable region is VK4 optionally incorporating any of the additional changes described in Examples 107–109. A preferred human heavy chain constant region is IgG3.

Chimaeric humanised antibodies represent another aspect of the invention. Preparation of chimaeric humanised antibody fragments of antibody 806.077 antibody is described in Example 8 herein. Chimaeric antibodies are generally constructed by combining the variable region from one species with a constant region from another antibody from a different species.

The term "humanised" in relation to antibodies as used herein includes any method of humanisation such as for example CDR grafting or chimaeric antibody preparation or any hybrid thereof such as for example a CDR grafted heavy chain in combination with a chimaerised light chain (see Example 110 for a suitable embodiment).

In particular, a rodent antibody on repeated in vivo administration in man either alone or as a conjugate will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like. For example, the gene sequences for the variable domains of the rodent antibody which bind CEA can be substituted for the variable domains of a human myeloma protein, thus producing a recombinant chimaeric antibody. These procedures are detailed in EP 194276, EP 0120694, EP 0125023, EP 0171496, EP 0173494 and WO 86/01533. Alternatively the gene sequences of the CDRs of the CEA binding rodent antibody may be isolated or synthesized and substituted for the corresponding sequence regions of a homologous human antibody gene, producing a human antibody with the specificity of the original rodent antibody. These procedures are described in EP 023940, WO 90/07861 and WO91/09967. Alternatively a large number of the surface residues of the variable domain of the rodent antibody may be changed to those residues normally found on a homologous human antibody, producing a rodent antibody which has a surface 'veneer' of residues and which will therefore be recognized as self by the human body. This approach has been demonstrated by Padlan et.al. (1991) Mol. Immunol. 28, 489.

According to another aspect of the present invention there is provided a host cell transformed with a polynucleotide sequence or a transgenic non-human animal or transgenic plant developed from the host cell in which the polynucloetide sequence encodes at least the variable region of the heavy chain or light chain of a CEA antibody of the invention, optionally in the form of a conjugate as described herein.

According to another aspect of the present invention there is provided hybridoma 806.077 deposited as ECACC deposit no. 96022936 and variant cell lines thereof.

Hybridoma 806.077 was deposited at the European Collection of Animal Cell Cultures (ECACC), PHLS Centre for Applied Microbiology & Research, Porton Down Salisbury, Wiltshire SP4 0JG, United Kingdom on Feb. 29, 1996 under accession no. 96022936 in accordance with the Budapest Treaty.

According to another aspect of the present invention there is provided plasmid pNG3-Vkss-HuCk deposited as NCIMB deposit no.40798.

Plasmid pNG3-Vkss-HuCk was deposited at The National Collections of Industrial and Marine Bacteria (NCIMB), 23 St Machar Drive, Aberdeen AB2 1RY, Scotland, United Kingdom on Apr. 11, 1996 under deposit reference number NCIMB 40798 in accordance with the Budapest Treaty.

According to another aspect of the present invention there is provided plasmid pNG4-VHss-HuIgG2CH1' deposited as NCIMB deposit no. 40797.

Plasmid pNG4-VHss-HuIgG2CH1' was deposited at The National Collections of Industrial and Marine Bacteria (NCIMB), 23 St Machar Drive, Aberdeen AB2 1RY, Scotland, United Kingdom on Apr. 11, 1996 under deposit reference number NCIMB 40797 in accordance with the Budapest Treaty.

According to another aspect of the present invention there is provided plasmid pNG3-Vkss-HuCk-NEO deposited as NCIMB deposit no. 40799.

Plasmid pNG3-Vkss-HuCk-NEO was deposited at The National Collections of Industrial and Marine Bacteria (NCIMB), 23 St Machar Drive, Aberdeen AB2 1RY, Scotland, United Kingdom on Apr. 11, 1996 under deposit reference number NCIMB 40799 in accordance with the Budapest Treaty.

According to another aspect of the present invention there is provided a method of making at least a variable region of a heavy or light chain of an anti-CEA antibody as herein defined comprising:
a) transforming a host cell with a polynucleotide sequence which encodes at least the variable region of the heavy or light chain of the anti-CEA antibody and optionally developing the transformed host cell into a transgenic non-human mammal or transgenic plant;
b) subjecting the host cell, transgenic non-human mammal or transgenic plant to conditions conducive to expression, and optionally secretion, of at least the variable region and optionally;
c) at least partially purifying the variable region.

According to another aspect of the present invention there is provided a method of making an antibody or a conjugate as defined herein which comprises:
a) subjecting a host cell, a transgenic non-human mammal or a transgenic plant as defined herein, or the 806.077 hybridoma, to conditions conducive to expression, and optionally secretion, of the antibody or conjugate; and optionally
b) at least partially purifying the antibody or conjugate.

Preferably both heavy and light chain variable regions are expressed in the same cell and assembled thereby to form an anti-CEA antibody. Preferably the heavy or light chain variable region is fused (optionally via some linking sequence) to a gene encoding a protein effector moiety (as part of a conjugate, see text below), preferably fusion is through the antibody heavy chain. Generally fusion can be either at the N or C terminus of the antibody chain. For B7 conjugates fusion at the N-terminus of the antibody chain is preferred. CPB has an N-terminal pro domain which is believed to assist correct folding of protein before the pro domain is removed to release active enzyme. If proCPB is fused at its C terminus to the N terminus of an antibody chain this allows removal of pro domain (e.g. by trypsin treatment) from the N terminus of the fusion construct. Alternatively if proCPB was attached to the C terminus of an antibody chain then the problem arises of having to remove the pro domain from the "middle" of the construct without destroying the fusion protein. The solution is to co-express the pro domain separately (in trans). This has the advantage, once the cell lines have been constructed, of not requiring trypsin activation of expressed fusion protein to remove CPB pro domain. Constructs with proCPB fused at its C terminus to the N terminus of an antibody chain have the advantage of not requiring construction of co-expression cell lines which require high level expression of the pro domain along with high level expression of other proteins.

According to another aspect of the present invention there is provided a method of making monoclonal antibody 806.077 comprising:
a) culturing hybridoma 806.077 antibody deposited as ECACC deposit no. 96022936 in medium under conditions conducive to expression of antibody therefrom and;
b) obtaining antibody 806.077 antibody from the culture medium and optionally;
c) preparing a F(ab')$_2$ fragment of antibody 806.077 antibody by enzymic digestion.

According to another aspect of the present invention there is provided a conjugate which comprises an effector moiety and an anti-CEA 806.077 antibody of the invention as herein described. An effector moiety is an entity having the effect of bestowing another activity (e.g. an enzyme, toxin or radioactive ligand) to the 806.077 antibody in forming the conjugate.

In one embodiment, preferably the effector moiety is an enzyme suitable for use in an ADEPT system. In International Patent Application WO 96/20011, published Jul. 4, 1996, we proposed a "reversed polarity" ADEPT system based on mutant human enzymes having the advantage of low immunogenicity compared with for example bacterial enzymes. A particular host enzyme was human pancreatic CPB (see for example, Example 15 [D253K]human CPB & 16 [D253R]human CPB therein) and prodrugs therefor (see Examples 18 & 19 therein). The host enzyme is mutated to give a change in mode of interaction between enzyme and prodrug in terms of recognition of substrate compared with the native host enzyme. In our subsequent International Patent Application No PCT/GB96/01975 (published Mar. 6, 1997 as WO 97/07796) further work on mutant CPB enzyme/prodrug combinations for ADEPT are described. Preferred enzymes suitable for ADEPT are any one of CPG2 or a reversed polarity CPB enzyme, for example any one of [D253K]HCPB, [G251T,D253K]HCPB or [A248S,G251T, D253K]HCPB.

806.077 Antibody conjugates also have application in tumour immunotherapy. Accordingly in another preferred embodiment the conjugate effector moiety is a co-stimulatory molecule, preferably the co-stimulatory molecule is B7, more preferably human B7.1 or B7.2 and especially human B7.1. Preferably the conjugate is in the form of a fusion protein, preferably in which the fusion protein is formed through linking a C-terminus of the co-stimulatory molecule to an N-terminus 806.077 antibody chain, preferably via the antibody chain heavy chain, preferably in which the 806.077 antibody lacks an Fc antibody region, more preferably a F(ab')$_2$ antibody fragment, more preferably the antibody is humanised or human. An especially preferred conjugate is described in Example 104 below.

The use of antibody to target a co-stimulatory molecule to tumour cells is predicted to bestow the function of antigen presenting to the tumour cells such that T-cells receive specific TCR stimulation from the tumour cell itself and a co-stimulatory signal from the antibody targeted molecule. The use of human or humanised antibodies is preferred for the treatment of human tumours because murine antibodies may evoke an immune reaction when used in man which might result in a reduction in effectivness on repeat therapy. The use of a fusion protein combining a tumour antigen binding region linked to the extracellular portion of a co-stimulatory molecule is novel. Hayden et al (Tissue Antigens, 1996, 48, 242–254) have reported the use of a bi-specific antibody molecule combining an anti-tumour antigen binding domain with an anti-CD28 binding domain. Whilst this molecule is capable of interacting with CD28 on T-cells, the signal it may deliver has the disadvantage of being qualitatively different from that provided by the natural CD28 ligands, for example the affinity of binding is greater than that between B7.1 and CD28. The cross-species homology between B7.1,B7.2 and CD28,CTLA-4 indicates evolutionary conservation of binding region sequences. Consequently it is believed that, for example B7.1 from man can interact with CD28 from mouse and may impart a similar co-stimulatory signal. For treatment of human disease a human or humanised protein is preferable. However, the use of a human or humanised protein in animal models could produce similar effects to that anticipated in man and such animal models should provide relevant data as to the efficacy of a human/humanised antibody fusion protein with human B7.1/B7.2 in the treatment of human disease.

Conjugation of the effector moiety and antibody may be by any suitable method such as for example chemical linkage via heterobifunctional linkers or recombinant gene fusion techniques. In general fusion proteins are preferred conjugates, particularly for conjugates with HCPB or B7.

Preferred conjugates are those in which the effector moiety is selected from any one of the following:
a) an enzyme suitable for use in an ADEPT system;
b) CPG2;
c) [G251T,D253K]HCPB;
d) [A248S,G251T,D253K]HCPB;
e) a co-stimulatory molecule;
f) extracellular domain of B7;
g) extracellular domain of human B7.1; and
h) extracellular domain of human B7.2;
optionally in the form of a fusion protein.

It will be appreciated that the conjugate of the present invention does not necessarily consist of one effector molecule and one antibody molecule. For example the conjugate may comprise more than one effector molecule per antibody molecule. In general, F(ab')$_2$ antibody conjugates which are fusions between the antibody and an enzyme or an extracellular domain of B7 will have 2 moles of enzyme or B7 per mole of antibody.

Especially preferred conjugates are a fusion protein selected from any one of the following conjugates, (sequences being listed in N terminus to C terminus direction):
a) a humanised 806.077 F(ab')$_2$-{[A248S,G251T,D253K]HCPB}$_2$ fusion comprising:
an antibody Fd' chain of structure VH1(SEQ ID NO: 55)/CH1 constant region from IgG3/hinge region from IgG3;
the Fd' chain being fused via its C terminus to the N terminus of [A248S,G251T,D253K]HCPB; and
an antibody light chain of formula VK4(SEQ ID NO: 71)/CL region from kappa light chain:
b) {[A248S,G251T,D253K]HCPB}$_2$-humanised 806.077 F(ab')$_2$ fusion comprising: [A248S,G251T,D253K]HCPB;
the HCPB being fused at its C terminus, via a (GGGS)$_3$ linker, to the N terminus of an antibody Fd' chain of structure VH1(SEQ ID NO: 55)/CH1 constant region from IgG3/hinge region from IgG3; and
an antibody light chain of formula VK4(SEQ ID NO: 71)/CL region from kappa light chain; and
c) a (human B7.1 extracellular domain)$_2$-humanised 806.077 F(ab')$_2$ fusion comprising: human B7.1 extracellular domain;
the B7.1 being fused at its C terminus to the N terminus of an antibody Fd' chain of structure VH1(SEQ ID NO: 55)/CH1 constant region from IgG3/hinge region from IgG3; and
an antibody light chain of structure VK4(SEQ ID NO: 71)/CL region from kappa light chain.

In this specification the antibody hinge region in relation to conjugates is defined according to the principles set out by Padlan (1994) in Molecular Immunology 31. 169–217: see Table 2 therein in particular. In these especially preferred conjugates there are 2 moles of enzyme or B7.1 per mole of F(ab')$_2$. The forward slash ("/") is merely a separator to indicate discrete structural elements joined by peptide bonds that make up parts of the conjugate.

The VH1 and/or VK4 variable region humanised sequences have the advantage of preserving good binding properties with minimal additional changes required to the human framework. The IgG3 hinge region has the advantage of giving good $F(ab')_2$ production levels and homogeneity of product.

In another preferred embodiment relating to the especially preferred conjugates defined above, fusion is effected through the antibody light chain. In yet another preferred embodiment relating to the especially preferred conjugates defined above, the CH1 constant region from IgG3/hinge region from IgG3 structural element may be replaced by the corresponding IgG2 element.

When the effector molecule is a toxin, this toxin moiety generally comprises a component which possesses cytotoxic properties and hence is capable of killing cells following internalisation.

The toxin moiety and the anti-CEA antibody may be coupled directly to one another, or they may be coupled indirectly. The toxin moiety and the anti-CEA antibody are, in general, coupled such that the geometry of the conjugate permits the anti-CEA antibody to bind to its target cell. Advantageously, the toxin moiety and the anti-CEA antibody are coupled such that the conjugate is extracellularly stable, and intracellularly unstable so that the toxin moiety and the anti-CEA antibody remain coupled outside the target cell, but following internalisation, the toxin moiety is released. Thus, advantageously the conjugate has an intracellularly cleavable/extracellularly stable site.

Examples of conjugates in which the toxin moiety is directly coupled to the target cell binding moiety include those in which the toxin moiety and the anti-CEA antibody are coupled by a disulphide bridge formed between a thiol group on the toxin moiety and a thiol group on the anti-CEA antibody. Details of the preparation and properties of immunotoxins and other conjugates are given in European patent application EP 528 527 (publication no.) the contents of which is incorporated herein by reference thereto.

According to another aspect of the present invention there is provided a polynucleotide sequence capable of encoding a polypeptide of an antibody or a conjugate as defined in any preceding claim. The term "capable of encoding" is intended to encompass polynucleotide sequences taking into account degeneracy in the genetic code in that some amino acids are encoded by more than one codon.

According to another aspect of the present invention there is provided a vector comprising a polynucleotide as defined above.

According to another aspect of the present invention there is provided a host cell transformed with a polynucleotide sequence as defined above or a transgenic non-human animal or transgenic plant developed from the host cell.

According to another aspect of the present invention there is provided a pharmaceutical composition comprising a conjugate of the invention described herein in association with a pharmaceutically-acceptable diluent or carrier, optionally in a form suitable for intravenous administration.

According to another aspect of the present invention there is provided a conjugate as described herein for use as a medicament.

According to another aspect of the present invention there is provided use of a conjugate as described herein for preparation of a medicament for treatment of neoplastic disease.

It will be appreciated that the dose and dosage regimen will depend upon the particular effector moiety employed, the population of the target cell and the patient's history. The dose of the conjugate administered will typically be in the range 0.1 to 1 mg/kg of patient weight.

The conjugates of the present invention will normally be administered in the form of a pharmaceutical composition. Thus according to the present invention there is also provided a pharmaceutical compostion which comprises a conjugate (as defined herein) in association with a pharmaceutically-acceptable diluent or carrier. An example of such a formulation is given herein in Example 10.

Pharmaceutical compositions of the present invention may be formulated in a variety of dosage forms. Generally, the conjugates of the present invention will be administered parenterally, preferably intravenously. A particular parenteral pharmaceutical composition is one which is formulated in a unit dosage form which is suitable for administration by injection. Thus, particularly suitable compositions comprise a solution, emulsion or suspension of the immunotoxin in association with a pharmaceutically acceptable parenteral carrier or diluent. Suitable carriers or diluents include aqueous vehicles, for example water or saline, and non-aqueous vehicles, for example fixed oils or liposomes. The compositions may include agents which enhance the stability of the conjugate in the composition. For example, the composition may include a buffer. The concentration of the conjugate will vary, but in general, the conjugate will be formulated at concentrations of about 1 to 10 mg/ml.

According to another aspect of the present invention there is provided an expression vector coding for an anti-CEA antibody of the invention as herein defined.

According to another aspect of the present invention there is provided an expression vector encoding at least the variable region of a heavy or light chain of an anti-CEA antibody as herein defined.

According to another aspect of the present invention there is provided a host cell transformed with a vector as herein described which is compatible with expression therein.

According to another aspect of the present invention there is provided a host cell transformed with a polynucleotide sequence as herein defined.

Mammalian cells (CHO, COS, myeloma) have been used as host for the co-expression of antibody H and L chain cDNAs and fragments thereof to produce antibody with the specified binding activity (Bebbington, C., 1991, Methods, vol 2, p136–145, and Adair, J., 1992, Immunological Reviews, vol 130). For expression of constructs leading to direct expression of active CPB, COS or CHO cell expression systems are preferred. The cDNAs can be introduced on plasmids and allowed to integrate into chromosomal DNA especially for CHO cells or allowed to replicate to very high copy number especially in COS cells. The plasmids generally require a selectable marker for maintenance in transfected hosts, an efficient eukaryotic promoter to allow a high level of transcription from the cDNAs, convenient restriction enzyme sites for cloning and polyadenylation and transcription termination signals for message stabilty. Several such vectors have been described in the literature (Bebbington, C. et al, 1992, Bio/Technology, vol 10, p169–175, and Wright, A., 1991, Methods, vol 2, p125–135) and there are commercially available vectors, (such as pRc/CMV ,Invitrogen Corp.) which are suitable.

The expression of a range of antibody fragments in E.coli is well documented (reviewed by Pluckthun, A., Immunological Reviews, 1992, vol 130, p151–188 and Skerra, A., Current Opinion in Immunology, 1993, vol 5, p256–262). Intracellular expression of Fd and L chains has been described (Cabilly, S., 1989, Gene. vol 85, p553–557) but this may require in vitro refolding and re-association of the chains (Buchner, J and Rudolph, R., 1991, Bio/Technology, vol 9, p157–162) to produce binding activity. A more efficient route to obtaining active antibody fragments is through periplasmic secretion (Better, M. et al, 1988, Science, vol 240, p1041–1043). The H and L chain components of the antibody fragment are co-expressed from a single plasmid. Each antibody chain is provided with a bacterial leader peptide which directs it to the E.coli periplasm where the leader is cleaved and the free chains associate to produce soluble and active antibody fragments. This process is believed to mimic the natural process in eukaryotic cells where the expressed antibody chains pass into the lumen of the endoplasmic reticulum prior to association into whole antibodies. This process often results in the presence of binding activity in the culture supernatant.

Some expression systems involve transforming a host cell with a vector; such systems are well known such as for example in E. coli, yeast and mammalian hosts (see Methods in Enzymology 185, Academic Press 1990). Other systems of expression are also contemplated such as for example transgenic non-human mammals in which the gene of interest, preferably cut out from a vector and preferably in association with a mammary promoter to direct expressed protein into the animal's milk, is introduced into the pronucleus of a mammalian zygote (usually by microinjection into one of the two nuclei (usually the male nucleus) in the pronucleus) and thereafter implanted into a foster mother. A proportion of the animals produced by the foster mother will carry and express the introduced gene which has integrated into a chromosome. Usually the integrated gene is passed on to offspring by conventional breeding thus allowing ready expansion of stock. Preferably the protein of interest is simply harvested from the milk of female transgenic animals. The reader is directed to the following publications: Simons et al. (1988), Bio/Technology 6:179–183; Wright et al. (1991) Bio/Technology 9:830–834; U.S. Pat. No. 4,873, 191 and; U.S. Pat. No. 5,322,775. Manipulation of mouse embryos is described in Hogan et al, "Manipulating the Mouse Embryo; A Laboratory Manual", Cold Spring Harbor Laboratory 1986.

Transgenic plant technology is also contemplated such as for example described in the following publications: Swain W.F. (1991) TIBTECH 9: 107–109; Ma J. K. C. et al (1994) Eur. J. Immunology 24: 131–138; Hiatt A. et al (1992) FEBS Letters 307:71–75; Hein M. B. et al (1991) Biotechnology Progress 7: 455–461; Duering K. (1990) Plant Molecular Biology 15: 281–294.

If desired, host genes can be inactivated or modified using standard procedures as outlined briefly below and as described for example in "Gene Targeting; A Practical Approach", IRL Press 1993. The target gene or portion of it is preferably cloned into a vector with a selection marker (such as Neo) inserted into the gene to disrupt its function. The vector is linearised then transformed (usually by electroporation) into embryonic stem (ES) cells (eg derived from a 129/Ola strain of mouse) and thereafter homologous recombination events take place in a proportion of the stem cells. The stem cells containing the gene disruption are expanded and injected into a blastocyst (such as for example from a C57BL/6J mouse) and implanted into a foster mother for development. Chimaeric offspring can be identified by coat colour markers. Chimeras are bred to ascertain the contribution of the ES cells to the germ line by mating to mice with genetic markers which allow a distinction to be made between ES derived and host blastocyst derived gametes. Half of the ES cell derived gametes will carry the gene modification. Offspring are screened (eg by Southern blotting) to identify those with a gene disruption (about 50% of progeny). These selected offspring will be heterozygous and therefore can be bred with another heterozygote and homozygous offspring selected thereafter (about 25% of progeny). Transgenic animals with a gene knockout can be crossed with transgenic animals produced by known techniques such as microinjection of DNA into pronuclei, sphaeroplast fusion (Jakobovits et al. (1993) Nature 362:255–258) or lipid mediated transfection (Lamb et al.

(1993) Nature Genetics 5 22–29) of ES cells to yield transgenic animals with an endogenous gene knockout and foreign gene replacement.

ES cells containing a targeted gene disruption can be further modified by transforming with the target gene sequence containing a specific alteration, which is preferably cloned into a vector and linearised prior to transformation. Following homologous recombination the altered gene is introduced into the genome. These embryonic stem cells can subsequently be used to create transgenics as described above.

The term "host cell" includes any procaryotic or eucaryotic cell suitable for expression technology such as for example bacteria, yeasts, plant cells and non-human mammalian zygotes, oocytes, blastocysts, embryonic stem cells and any other suitable cells for transgenic technology. If the context so permits the term "host cell" also includes a transgenic plant or non-human mammal developed from transformed non-human mammalian zygotes, oocytes, blastocysts, embryonic stem cells, plant cells and any other suitable cells for transgenic technology.

According to another aspect of the present invention there is provided a method of treatment of a human or animal in need of such treatment which comprises administration to a human or animal of a pharmaceutically effective amount of a conjugate as herein described.

According to another aspect of the present invention there is provided a method of targeting an effector moiety to cells displaying antigen CEA in a mammal in need of such targeting which comprises administration of a pharmaceutically effective amount of an conjugate of the invention as herein defined.

According to another aspect of the present invention there is provided the use of an antibody as hereinbefore described in a diagnostic method.

One diagnostic method is immunoassay. An immunoassay for in vitro testing based upon the novel antibody according to the invention may be designed in accordance with conventional immunological techniques in the art, utilising the antibody according to the invention in a labelled or unlabelled form and determining the complex formation of the antibody with CEA in the sample to be tested. In one case, the antibody may be labelled with a detectable label, such as radiolabel, a chemiluminescer, a fluorescer or an enzyme label. Alternatively the antibody is detected via a complex formed with a labelled substance or by non-labelling techniques, such as biosensor methods eg based upon surface plasmon resonance. The sample may, for example, be in the form of a body fluid, such as serum, or a tissue preparation (histochemical assay).

For in vivo diagnostic purposes, the antibody according to the invention is provided with a suitable externally detectable label, such as eg. a radiolabel or a heavy metal atom, and administered to a subject whereupon the possible localised accumulation of antibody in the body is determined.

For the in vitro diagnosis of cancer the anti-CEA antibody can be conjugated to either enzymes such as horse radish peroxidase and bacterial luciferase which can generate a signal which can be measured or to fluorescent markers or radioisotopes which can be detected and quantitated directly. In a standard immunoassay system such conjugates provide a means of measuring the presence or absence of CEA in body tissues and consequently provides a rapid and convenient test for the diagnosis of tumour disease. See general descriptions of the methodology involved in Enzyme immunoassay, E. T. Maggio, CRC Press and U.S. Pat. No. 3690 8334, U.S. 3,791,932, U.S. 3,817,837, U.S. 3,850,578, U.S. 3,853,987, U.S. 3,867,517, U.S. 3,901,654, U.S. 3,935,074, U.S. 3,984,533, U.S. 3,996,345 and U.S. 4,098,876.

For the in vivo diagnosis of cancer, the anti-CEA antibody can be conjugated to isotopes of elements such as yttrium, technetium or indium or heavy metal isotopes which can be detected by whole body imaging cameras (see Larson, S. M., 1987, Radiology, 165, 297–304.

For the therapy of cancer, preferred embodiments involve an anti-CEA antibody that can be conjugated to an effector moiety which can kill the cancer cells directly or especially via activation of a suitable prodrug in an ADEPT system. In ADEPT selective killing of tumour cells is achieved by conjugating the anti-CEA antibody to an enzyme which is capable of catalysing the conversion of a non-toxic dose of a prodrug into a potent toxic drug compound. Administration of the conjugate leads to localization of the enzyme activity at the tumour site. Subsequent administration of the prodrug leads to local production of the toxic drug and selective kill at the tumour site. This approach is described in WO 88/07378, U.S. Pat. No. 4,975,278, U.S. 5,405,990 and WO89/10140. Antibody 806.077 may also be used conjugated to a co-stimulatory molecule for tumour immunotherapy as described above.

Selective cell killing of tumour cells can also be achieved by conjugation of the anti-CEA antibody either directly or by chemical derivatization with macrocycle chelators containing high energy radioisotopes such as $^{90}Y$, $^{131}I$ and $^{111}In$. The anti-CEA antibody serves to localize the isotope to the tumour and the radiation emitted by the isotope destroys the DNA of the surrounding cells and kills the tumour.

Selective killing of tumour cells can also be achieved by conjugation of the anti-CEA antibody to cytotoxic and cytostatic drugs such as methotrexate, chlorambucil, adriamycin, daunorubicin and vincristine. These drugs have been used in the clinic for many years and the therapy they provide is often limited by non specific toxicity. Conjugation of these drugs to the CEA antibody enables these drugs to localize at the tumour site and thus increasing the dose of drug that can be delivered to the tumour without incurring unacceptable side effects from the action of such drugs on other tissues such as the bone marrow or nervous system. The effectiveness of the antibody is in many applications improved by reducing the size of the antibody binding structure and thereby improving the tissue penetration and other pharmacodynamic properties of the pharmaceutical composition. This can be achieved by removing the Fc region of the antibody molecule either enzymically or by genetic engineering methods to produce a recombinant Fab' or F(ab')$_2$ fragment.

Genetic engineering methods can also be used to further reduce the size of the anti-CEA antibody. The Fv which contain the CDRs can be engineered and expressed in isolation and chemically cross linked for instance by the use of disulphide bridges. Alternatively, both the light and heavy chain domains making up the Fv structure may be produced as a single polypeptide chain (SCFv) by fusing the Fv domains with a linker peptide sequence from the natural C-terminus of one domain to the N-terminus of the other domain (see PCT/US/87/02208 and U.S. Pat. No. 4,704,692). Alternatively, a single Fv domain may be expressed in isolation forming a single domain antibody or dAb as described by Ward et al Nature(1989) 341, 544. Another type of anti-CEA antibody contemplated is a V-min construct as disclosed in International Patent Application WO 94/12625 (inventors Slater & Timms). Abbreviations used herein include:

| | |
|---|---|
| ADEPT | antibody directed enzyme prodrug therapy |
| APC | antigen presenting cell |
| CDRs | complementarity determining regions |
| CEA | Carcinoma Embryonic Antigen |
| CL | constant domain of antibody light chain |
| CPB | carboxypeptidase B |
| CPG2 | carboxypeptidase G2 |
| DAB | substrate 3,3'-diaminobenzidine tetrahydrochloride |
| DEPC | diethylpyrocarbonate |
| DMEM | Dulbecco's modified Eagle's medium |
| ECACC | European Collection of Animal Cell Cultures |
| EIA | enzyme immunoassay |
| ELISA | enzyme linked immunosorbent assay |
| FCS | foetal calf serum |
| Fd | heavy chain of Fab, Fab' or F(ab')$_2$ optionally containing a hinge |
| HAMA | Human Anti Mouse Antibody |
| HCPB | human carboxypeptidase B, preferably pancreatic |
| hinge (of an IgG) | a short proline rich peptide which contains the cysteines that bridge the 2 heavy chains |
| HRPO | horse radish peroxidase |
| NCA | non-specific cross reacting antigen |
| NCIMB | National Collections of Industrial and Marine Bacteria |
| PBS | phosphate buffered saline |
| PCR | polymerase chain reaction |
| preproCPB | proCPB with an N-terminal leader sequence |
| proCPB | CPB with its N-terminal pro domain |
| SDS-PAGE | sodium dodecyl sulphate - polyacrylamide gel electrophoresis |
| TBS | Tris-buffered Saline |
| VH | variable region of the heavy antibody chain |
| VK | variable region of the light antibody chain |

The invention is illustrated by the following non-limiting Examples (supported by Reference Examples which follow the Examples) in which.

Figure 1:
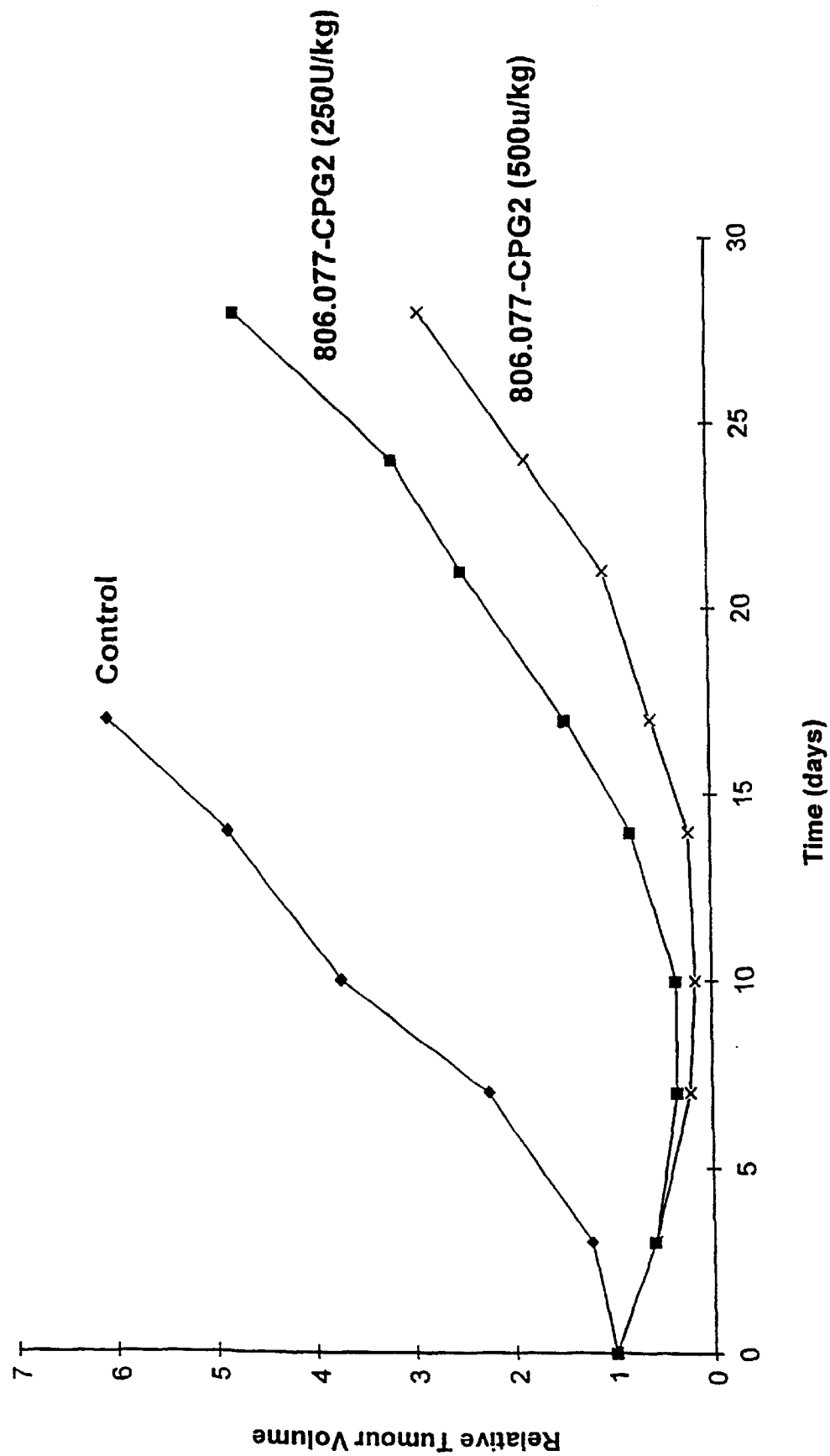
FIG. 1 shows anti-tumour activity of 806.077 antibody-CPG2 conjugate in an ADEPT model.

DNA is recovered and purified by use of GENECLEAN™ II kit (Stratech Scientific Ltd. or Bio 101 Inc.). The kit contains: 1) 6M sodium iodide; 2) a concentrated solution of sodium chloride, Tris and EDTA for making a sodium chloride/ethanol/water wash; 3) Glassmilk a 1.5 ml vial containing 1.25 ml of a suspension of a specially formulated silica matrix in water. This is a technique for DNA purification based on the method of Vogelstein and Gillespie published in Proceedings of the National Academy of Sciences USA (1979) Vol 76, p 615. Briefly, the kit procedure is as follows. To 1 volume of gel slice is added 3 volumes of sodium iodide solution from the kit. The agarose is melted by heating the mix at 55° C. for 10 min then Glassmilk (5–10 ml) is added, mixed well and left to stand for 10 min at ambient temperature. The glassmilk is spun down and washed 3 times with NEW WASH (0.5 ml) from the kit. The wash buffer is removed from the Glassmilk which is to dry in air. The DNA is eluted by incubating the dried Glassmilk with water (5–10 ml) at 55° C. for 5–10 min. The aqueous supernatant containing the eluted DNA is recovered by centrifugation. The elution step can be repeated and supernatants pooled;

Competent *E. coli* DH5α cells were obtained from Life Technologies Ltd (MAX efficiency DH5α competent cells);

Mini-preparations of double stranded plasmid DNA were made using the RPM™ DNA preparation kit from Bio101 Inc. (cat. No 2070-400) or a similar product—the kit contains alkaline lysis solution to liberate plasmid DNA from bacterial cells and glassmilk in a spinfilter to adsorb liberated DNA which is then eluted with sterile water or 10 mM Tris-HCl, 1 mM EDTA, pH 7.5;

Serum free medium is OPTIMEM™ I Reduced Serum Medium, GibcoBRL Cat. No. 31985;

LIPOFECTIN™ Reagent (GibcoBRL Cat. No. 18292-011) is a 1:1 (w/w) liposome formulation of the cationic lipid N-[1-(2,3-dioleyloxy)propyl]-n,n,n-trimethylammonium chloride (DOTMA) and dioleoyl phosphatidylethanolamine (DOPE) in membrane filtered water. It binds spontaneously with DNA to form a lipid-DNA complex—see Felgner et al. in Proc. Natl. Acad. Sci. USA (1987) 84, 7431;

G418 (sulphate) is GENETICIN™, GibcoBRL Cat. No 11811, an aminoglycoside antibiotic related to gentamicin used as a selecting agent in molecular genetic experiments;

AMPLITAQ™ available from Perkin-Elmer Cetus, is used as the source of thermostable DNA polymerase; and General molecular biology procedures can be followed from any of the methods described in "Molecular Cloning—A Laboratory Manual" Second Edition, Sambrook, Fritsch and Maniatis (Cold Spring Harbor Laboratory, 1989).

EXAMPLE 1

Discovery and Establishment of Hybridoma Cell Line 806.077

BALB/C mice, 8 to 10 weeks old, were immunised subcutaneously with a primary dose of CEA (10 μg) in phosphate buffered saline solution (0.1 ml) and Freund's Complete adjuvant (0.1 ml). Two weeks later and again 2 weeks later the animals were boosted with further doses of CEA (10 μg) in phosphate buffered saline (0.1 ml) mixed with Freund's Incomplete adjuvant (0.1 ml). Thirty two weeks later the animals were given a final intravenous immunisation of CEA (10 μg) in phosphate buffered saline and sacrificed three days later. The spleens were removed and prepared and fused with NS0 cells (available from the European Collection of Animal Cell Cultures under the accession No. 85110503) by standard methods (Kohler and Milstein, Nature (1975) 256, 495). The resulting cells were distributed into 96-well culture dishes and incubated for 2 weeks. The supernatants from the resulting hybridomas were screened by EIA (enzyme immunoassay). From a total of 1,824 wells generated from 5 fusions, 102 wells were positive against native CEA. In fusion 806, seventeen wells were found to be positive. The cells contained in these wells were cloned by limiting dilution, and the resulting clones tested by EIA. Lines from 10/17 original wells cloned successfully. One line, designated 806.077, has been deposited with the European Collection of Animal Cell Cultures under Accession No. 96022936. The table below provides a summary of the antibody generation programme that led to discovery of the 806.077 antibody hybridoma.

| Antigen | housing | rest weeks | number fusions | number Wells tested | number CEA* +ve by EIA | number finally selected |
|---|---|---|---|---|---|---|
| Untreated CEA | normal | 8–20 | 28 | 13,920 | 99 | 0 |
| desialated CEA | normal | 8–12 | 14 | 5,568 | 12* | 0 |

-continued

| Antigen | housing | rest weeks | number fusions | number Wells tested | number CEA* +ve by EIA | number finally selected |
|---|---|---|---|---|---|---|
| conjugated CEA | normal | 10–12 | 8 | 3,168 | 1 | 0 |
| Untreated CEA | isolator | >30 | 5 | 1,824 | 102 | 3 |

*tested against untreated CEA desialated immunisations produced lots of +ves when tested against the immunogen EXAMPLE 2
Preparation of 806.077 Antibody from Deposited Hybridoma Cell Line ECACC No. 96022936
2.1 Preparation from Serum Containing Medium A 1 ml cryopreserved ampoule was removed from storage in liquid nitrogen and rapidly thawed in a 37° C. water bath. The contents were aseptically transferred to a sterile 15 ml centrifuge tube. The cells were resuspended by dropwise addition of 10 ml of Dulbecco's modified Eagle's medium (DMEM) containing 10% (v/v) foetal calf serum (FCS) accompanied by gentle mixing. The suspension was centrifuged at 50×g for 10 min, the supernatant aseptically removed and the pellet resuspended in 5 ml of DMEM, 10% FCS and 1% L-glutamine in a 95% air 5% carbon dioxide pre-gassed 25 ml tissue culture flask. The flask was incubated at 36.5° C. in the dark.

After 3 days the flask was sub-cultured by passing the contents of the entire flask into a larger 75 ml flask diluting with DMEM, 10% FCS and 1% L-glutamine (final viable density=2–3×$10^5$ cells/ml). Further expansion to 162 ml flasks was performed in a similar manner.

Culture supernatants for purification were prepared in 500 ml roller cultures in 850 ml roller bottles. Cultures were seeded at 2×$10^5$ viable cells/ml in pre-gassed roller bottles, rotated at 3 rpm and incubated at 36.5° C. Cultures were grown to maturity and harvested typically 500–800 hours after inoculation when the cell viability was below 10% and IgG concentration had reached a maximum.
2.2 Treatment of Culture Harvests After harvest, roller bottle culture supernatants were clarified by centrifugation at 60×g for 30 minutes. Sodium azide (0.02% w/v) was added as a preservative to the clarified supernatant which was stored at 4° C. in the dark until purification.
2.3 Purification of 806.077 Antibody 806.077 Antibody hybridoma supernatant (3 l) was adjusted to pH 7.5 with dilute aqueous sodium hydroxide and filtered through a 0.45 cm filter (Millipore MILLIDISK™). The filtered antibody supernatant was loaded onto an affinity column of Protein G (for example Protein G Fast Flow SEPHAROSE™, Pharmacia product code 17.0618.03; 5 cm i.d×6.5 cm=130 ml;) equilibrated in phosphate buffered saline ("PBS"; 8 mM $Na_2HPO_4$, 1.5 mM $KH_2PO_4$, 150 mM NaCl, 2.5 mM KCl, pH 7.3, for example as available in tablet form for reconstitution from Oxoid) at 4° C. at a flow-rate of 4 ml/min. The column was washed with PBS (260 ml) at the same flow rate and the antibody eluted with 100 mM sodium citrate pH 2.6, collecting fractions and monitoring the eluate by UV absorption (280 nm). The UV absorbing fractions containing the antibody, were bulked, immediately adjusted to pH 7 and concentrated to about 2 mg/ml by ultrafiltration using a 30 kDa cut-off membrane (e.g. Amicon YM30). Dialysis, using a 6–8 kDa porosity cut-off membrane (e.g. SPECTRAPOR™ 1) membrane, into 50 mM tris-HCl pH 7.0 buffer yielded 110 mg 806.077 antibody, >95% pure by SDS-PAGE.

EXAMPLE 3
Selectivity of 806.077 Antibody

To assess selectivity, many human normal and tumour tissues have been screened for reactivity with the antibody 806.077, using sensitive three-stage indirect immunohistology on acetone-fixed, frozen cryostat sections.

Immunohistology was carried out on sections of human tissue obtained either at resection surgery or at post mortem. To preserve optimal morphology and antigenicity, tissues were obtained as fresh as possible, cut into small pieces (about 0.5 $cm^3$) and flash frozen in liquid nitrogen prior to storage at −80° C. Sections of tissue (6μ) were cut on a cryostat, mounted on polylysine coated slides (e.g. blue TECHMATE™ slides, Dako) and fixed in ice-cold acetone for 2 minutes before being wrapped in foil and stored at −80° C.

Slides were allowed to defrost at room temperature before being unwrapped from the foil immediately prior to use. Each section was outlined with a diamond marker, and to each section was added either 100 μl 806.077 antibody diluted to 2 μg/ml in Tris-buffered Saline (TBS), or 100 μl CEA/NCA reactive control (A5B7 antibody) at 2 μg/ml in TBS, or 100 μl MOPC isotype control (Sigma Chemical Company, St. Louis, U.S.A., Cat. No. M 9269) at 2 μg/ml in TBS, or relevant positive control such as LP34 (Dako). All subsequent incubations were carried out at room temperature for 30 minutes in a humidified chamber: all wash steps were in TBS with 2 changes. After incubation, the slides were washed and 100 μl of second antibody reagent, comprising 1/50 rabbit anti-mouse immunoglobulins conjugated to horse radish peroxidase (Dako Patts) and 1/5 normal human serum (Sigma) in TBS was added to each section.

The slides were again incubated and washed in TBS. A final detecting antibody, 100 μl swine anti-rabbit immunoglobulin conjugated to horse radish peroxidase (1150 dilution with 115 normal human serum in TBS), was added to each section, incubated and washed thoroughly. DAB substrate (3,3'-diaminobenzidine tetrahydrochloride) was prepared using 1 DAB tablet (Sigma) with hydrogen peroxide (17 μl) in TBS (17 ml), and added dropwise through a fast filter paper (e.g. Whatman Number 4). After 3 minutes incubation the excess DAB was tapped off the slides and the slides were washed in TBS. After counter staining with haematoxylin (e.g. Mayer's Haematoxylin, Shandon) sections were dehydrated in alcohol and xylene, and mounted in non-aqueous synthetic mountant (e.g. E-Z mountant, Shandon) before examination under a microscope.

The areas of antibody bonding were visualised by brown staining on the section. A scoring system was used to evaluate the degree of binding of 806.077 antibody to tissues:

+++ (strong) = antibody binding to >75% tumour cells
++ (moderate) = antibody binding to 50%–75% tumour cells
+ (weak) = antibody binding to 25%–50% tumour cells
+/− (minimal) = non-focal antibody binding to a small area of tumour cells
− = no staining Carcinoembryonic antigen (CEA) is a member of the immunoglobulin gene superfamily with one predicted variable-like domain region (N domain; 108 amino acids) and three sets of constant domain-like regions A1B1, A2B2 and A3B3; 92 amino acids for A domains and 86 amino acids for B domains (Hefta, 1992, Cancer Research 52:5647–5655. In addition, CEA possesses two signal peptides, one at the amino terminus and one at the carboxyl terminus. Both are removed during post-translational processing, the one at the carboxy terminus being replaced by a glycosylphosphatidylinositol (GPI) moiety. A large number of CEA-related proteins with varying homology to CEA have been reported (Thompson, 1991, J. of Clinical Laboratory Analysis, 5: 344–366). These include non-specific cross reacting antigens, NCA 1 and 2. These related proteins are expressed on a range of normal tissues including granulocytes and normal lung epithelium. The majority of anti-CEA monoclonal antibodies generated so far, cross react with one of these related proteins and thus react with a range of normal tissues and often react strongly with either granulocytes or lung epithelium.

Anti-CEA antibody, 806.077 was identified as being CEA selective, exhibiting no cross reactivity to granulocytes and only minimal staining to 4/14 normal lung tissues tested. 806.077 antibody was initially screened for tumour and NCA selectivity as a tissue culture supernatant. The screens were carried out using the supernatant neat and diluted at 1:10 and demonstrated equivalent binding of the antibody to colon tumours when compared to A5B7, but much reduced binding to normal lung and spleen tissues when compared to the same antibody. The antibody was affinity purified (as described in Example 2) and the screens repeated and extended to include further tumours and tissue types.

The antibody was titrated against a panel of colo-rectal tumour sections and this screen demonstrated the optimum screening concentration of 806.077 antibody to be 2 µg/ml. All subsequent screens were carried out using the antibody at this concentration. The results of these screens were as follows. The reactivity of 806.077 antibody was compared against A5B7 (also screened at 2 µg/ml) against the following tumours/normal tissues:

806.077 Antibody Tumour Reactivity:
Colon tumours (n=17).
Moderate to strong reactivity (++/+++equivalent to A5B7) was seen to all 17 tumours tested.
Breast tumours (n=6).
Moderate/weak staining (+/++), 2/6 tumours; minimal staining(+/−), 2/6 tumours.
NSCLC tumours (n=6).
Strong staining (+++), 2/6 tumours; moderate staining (++), 1/6 and weak staining (+), 2/6 tumours.
Gastric tumours (n=2).
Strong staining (+++), ½ tumours; weak staining (+) ½ tumours.
Ovary tumours (n=3) and prostate tumours (n=3).
No staining was seen to any of these tumours.
In all cases, equivalent reactivity was seen with A5B7.
Normal tissue reactivity:
Lung (NCA reactivity) (n=14).
Weak staining (+), 4/14 lung tissues; no staining (−) 10/14 tissues.
A5B7 bound moderately (++), 1/14 lung tissues; weakly (+), 10/14 tissues and minimally (+/−), 1/14 tissues.
Spleen (granulocyte/NCA reactivity) (n=6).
No staining was seen to any of the spleen tissues tested.
A5B7 bound moderately (++), 1/6 tissues and weakly (+), 5/6 tissues
Post mortem normal tissues (n=13).
Moderate/weak reactivity (++/+) was seen only to oesophagus, skin, colon and pancreas tissues (CEA expressing normal tissues). Similar binding was seen with A5B7. in addition to the positive tissues, colon, skin, oesophagus and pancreas, the negative tissues were: cerebellum, mid-brain, cerebrum, smooth muscle, liver, kidney, aorta, stomach, heart.

EXAMPLE 4

Generation of 806.077 Antibody F(ab') Fragment

Ficin (10 mg) was suspended in a solution of 50 mM cysteine (3 ml; BDH 37218) and 50 mM tris-HCl pH 7.0 and incubated at 37° C. for 30 minutes. Excess cysteine was removed by size exclusion chromatography (Sephadex™ G-25 column, 1.5 cm×25 cm; Pharmacia) in 50 mM tris-HCl pH 7.0 buffer. The reduced ficin concentration was determined by monitoring UV absorbance at A280 nm (assuming that a 1 mg/ml solution has an absorbance reading of 2 in a 1 cm cell) and was found to be 1.65 mg/ml.

A solution of 806.077 antibody (100 mg) in 50 mM tris-HCl buffer pH 7.0 (50 ml) and freshly reduced ficin (5 mg; 3 ml of the above solution) was digested at 37° C. over 20 hours. The digest was then diluted with an equal volume of PBS and loaded onto a Protein G affinity column (Pharmacia SEPHAROSE™ Fast Flow, 5.0 cm i.d×6.5 cm=125 ml; previously equilibrated with 50 mM tris-HCl pH 7.0 buffer at 4° C.), at a constant flow-rate of 3 ml/min. The column was washed with 50 mM sodium acetate pH 4.0 (250 ml) to remove low M.W. fragments, followed by 50 mM sodium citrate pH 2.8 to elute the $F(ab')_2$, monitoring the UV adsorbance of the eluate at A280 nm. The $F(ab')_2$ containing eluate was adjusted to pH 7 and buffer exchanged into 100 mM sodium phosphate/100 mM sodium chloride/1 mM EDTA pH 7.2 by dialysis and concentrated to 8 mg/ml by membrane filtration using a 10 kDa cut-off (e.g. Amicon™ YM10) assuming that a 1 mg/ml solution has an absorbance reading at 280 nm of 1.4 in a 1 cm cell. A 65% yield of 42 mg 95% pure $F(ab')_2$ was obtained.

EXAMPLE 5

Preparation of 806.077 Antibody $F(ab')_2$— Carboxypeptidase G2 Conjugate

The linker for 806.077 antibody $F(ab')_2$ derivatisation was SATA (S-acetyl thioglycollic acid N-hydroxysuccinimide ester, Sigma, product code A 9043) The linker for carboxypeptidase G2 (CPG2) derivatisation was SMPB [4-p-maleimidophenyl] butyric acid N-hydroxysuccinimide ester, Sigma, product code M6139]

5.1 F(ab'), Derivatisation:

To a solution of the $F(ab')_2$ fragment (40 mg, prepared as described in Example 4) in 100 mM phosphate/100 mM NaCl/1 mM EDTA pH 7.2 (buffer A; 5 ml) was mixed with SATA (0.28 mg) in DMSO (28 µl). After 40 minutes at room temperature the resulting solution was applied to a desalting column (SEPHADEX™ G-25, 1.5 cm i.d×50 cm=100 ml; equilibrated in buffer A at 4° C.) at a flow-rate of 1.2 ml/min. to remove excess reagents. The eluate was monitored by UV absorption at A280 nm. The SATA derivatised $F(ab')_2$ was pooled and mixed with 10% v/v 500 mM hydroxylamine HCl/500 mM sodium phosphate/30 mM EDTA pH 8.0 for 60 minutes at room temperature to deacetylate the derivatised $F(ab')_2$. The protein concentration was determined by UV absorption at 280 nm assuming that a 1 mg/ml solution has an absorbance reading of 1.4 in a 1 cm cell. The solution was diluted to about 1 mg/ml with buffer A. The linker loading was determined by Eliman's -SH assay and found to be 1.8–2.0 linkers/mole $F(ab')_2$.

5.2 CPG2 Derivatisation:

Large scale purification of CPG2 from Pseudomonas RS-16 was described in Sherwood et al. (1985), Eur, J. Biochem., 148, 447–453. Preparation of $F(ab')_2$ and IgG antibodies coupled to CPG enzyme may be effected by known means and has been described for example in PCT WO 89/10140. CPG may be obtained from Centre for Applied Microbiology and Research, Porton Down, Salisbury, Wiltshire SP4 0JG, United Kingdom. CPG2 may also be obtained by recombinant techniques. The nucleotide coding sequence for CPG2 has been published by Minton, N. P. et al., Gene, (1984) 31, 31–38. Expression of the coding sequence has been reported in *E.coli* (Chambers. S. P. et al., Appl. Microbiol, Biotechnol. (1988), 29, 572–578) and in *Saccharomyces cerevisiae* (Clarke, L. E. et al., J. Gen Microbiol, (1985) 131, 897–904). Total gene synthesis has been described by M. Edwards in Am. Biotech. Lab (1987), 5, 3844. Expression of heterologous proteins in *E.coli* has been reviewed by F. A. O. Marston in DNA Cloning Vol. III, Practical Approach Series, IRL Press (Editor D M Glover), 1987, 59–88. Expression of proteins in yeast has been reviewed in Methods in Enzymology Volume 194, Academic Press 1991, Edited by C. Guthrie and G R Fink.

CPG enzyme is available from Sigma Chemical Company, Fancy Road, Poole, Dorset, U.K. CPG enzyme was described in: Goldman. P. and Levy, C. C., PNAS USA, 58: 1299–1306 (1967) and in: Levy, C. C. and Goldman P., J. Biol. Chem., 242: 2933–2938 (1967). Carboxypeptidase G3 enzyme has been described in Yasuda, N. et al., Biosci. Biotech. Biochem., 56: 1536–1540 (1992). Carboxypeptidase G2 enzyme has been described in European Patent 121 352.

CPG2 (50 mg; recombinant enzyme from *E. coli*) was dialysed into 100 mM sodium phosphate/100 mM sodium chloride pH 7.2 (=buffer B) and diluted to 8 mg/ml, assuming that a 1 mg/ml solution has an absorbance reading at 280 nm of 0.6 in a 1 cm cell.

SMPB(Sigma) was dissolved in DMSO at 10 mg/ml. CPG2 (50 mg in buffer B at 8 mg/ml) was mixed with the SMPB solution (0.108 ml; 1.08 mg), and reacted at room temperature for 120 minutes. Excess reagents were removed on a desalting column (Sephadex G-25, 1.5 cm i.d×50 cm=100 ml; equilibrated in buffer B at 4° C.) at 1.2 ml/min. Derivatised CPG2 was pooled and the concentration determined by V A280 nm, assuming that a 1 mg/ml solution has an absorbance reading at 280 nm of 0.6 in a 1 cm cell. The solution was diluted to a CPG2 concentration of about 1 mg/ml. The linker loading was determined by a 'reverse' Ellman's assay, by adding a known amount of 2-mercaptoethanol to the maleimido-derivatised CPG2 and assaying unreacted —SH. A linker loading of 2.0–2.4 linkers/mole CPG2 was found.

5.3 Conjugation:

Equal weights of the deacetylated derivatised F(ab')$_2$ and derivatised CPG2 were mixed under nitrogen and the mixture (about 80 ml, at a total protein concentration of about 1 mg/ml) left at room temperature for 20 h. The reaction was terminated by the addition of 10% v/v 100 mM aqueous glycine. The crude conjugation mixture was buffer exchanged by dialysis into a low salt buffer (50 mM sodium acetate pH 6.0) and applied to a dye-ligand affinity column (where the dye binds to CPG2 e.g. ACL Mimetic Green 1, 2.5 cm i.d×10 cm=50 ml) at 4° C. equilibrated in the same buffer, to remove unreacted derivatised F(ab')$_2$. The conjugate and derivatised CPG2 were eluted with 50 mM acetate/500 mM NaCl pH 6.0, at a flow rate of 2.0 ml/min monitoring the elution by UV (A280 nm).

The crude conjugate, still containing derivatised CPG2, was concentrated using a 10 kDa cut-off ultrafiltration device (e.g. Amicon YM10™) to about 12 ml, at 5 mg/ml total protein concentration and 10% v/v 10 mM zinc sulphate (Sigma Z 0251) in water was added to replenish zinc lost to the CPG2 in the process. Further chromatography by size exclusion (e.g. SEPHACRYL S-300HR™ Pharmacia, 2.5 cm i.d×25 cm=500 ml) at 4° C. in 50 mM sodium acetate/150 mM sodium chloride pH 6.0 at a flow-rate of 1 ml/min., collecting fractions and monitoring by UV A280 nm, resulted in the fractionation of the conjugate and its separation from unreacted derivatised CPG2, as determined by SDS-PAGE of column fractions.

The peak containing conjugate (with ratios of F(ab')$_2$: CPG2 of 1:2, 1:1 and 2:1) was pooled and concentrated by ultrafiltration to 1.3 mg/ml, the protein concentration being determined by monitoring UV adsorbance at A280 nm (assuming 1 mg/ml has an absorbance of 1.0). Purity of the conjugate was determined by SDS PAGE and found to contain a total of 12 mg conjugate with the composition 65% 1:1 ratio conjugate, 20% 1:2 or 2:1 ratio conjugate with <5% free derivatised F(ab')$_2$ and <5% free derivatised CPG2.

EXAMPLE 6

Anti-Tumour Activity of 806.077 Antibody F(ab')$_2$-CPG2 Conjugate in Combination with a Prodrug.

The anti-tumour activity of the 806.077 antibody F(ab')$_2$-CPG2 conjugate prepared as described in Example 5 was evaluated in combination with the prodrug N(4-[N,N-bis(2-chloroethyl)amino]-phenoxycarbonyl)-L-glutamic acid (called "PGP" in this example, is described in Example 1 in U.S. Pat. No. 5,405,990 and Blakey et al., Br. J. Cancer 72, 1083–88, 1995) in a human colorectal tumour xenograft model.

Groups of 8–10 female athymic nude mice were injected s.c. with 1×10$^7$ LoVo colorectal tumour cells (ECACC no 87060101). When the tumours were 4–5 mm in diameter either 806.077 antibody F(ab')$_2$-CPG2 conjugate (250 U CPG2 enzyme activity Kg$^{-1}$) or phosphate buffered saline (170 mM NaCl, 3.4 mM KCl, 12 mM Na$_2$HPO$_4$, 1.8 mM KH$_2$PO$_4$, pH 7.2) was injected intravenously (i.v). Seventy-two hours later PGP prodrug was injected i.p. (3 doses of 40 mg/Kg at 1 h intervals). The length of the tumours in two directions was then measured three times a week and the tumour volume calculated using the formula:

$$\text{Volume} = \pi/6 \times D^2 d$$

where D is the larger diameter and d is the smaller diameter of the tumour. Tumour volume was expressed relative to the tumour volume at the time of initiation of the prodrug arm of the therapy. The anti-tumour activity was compared with control groups given PBS instead of either conjugate or prodrug. Anti-tumour activity was expressed both as a growth delay defined as the time it takes treated tumours to increase their volume by 4-fold minus the time it takes control tumours to increase their volume 4-fold and as a T/C value defined as the volume of the treated tumour divided by the volume of the control tumour 14 days after prodrug administration. Statistical significance of the anti-tumour effects was judged using the analysis of variance (one-way) test.

The anti-tumour activity of 806.077 antibody F(ab')$_2$-CPG2 conjugate in combination with PGP prodrug are shown in FIG. 1 and the anti-tumour data is summarised below. Anti-tumour activity of 806.077 antibody F(ab')2-CPG2 conjugate in combination with PGP prodrug in LoVo tumour xenografts.

| Conjugate | Dose (U/kg) | T/C (%) | Growth delay (days) | Significance (p) |
|---|---|---|---|---|
| 806.077 F(ab')$_2$-CPG2 | 250 | 16.5 | 14 | <0.01 |
|  | 500 | 4.7 | 22 | <0.01 |

The results demonstrate that the 806.077 antibody F(ab')$_2$-CPG2 conjugate in combination with the PGP prodrug produce tumour regressions and prolonged growth delays which were statistically significant compared with control groups.

EXAMPLE 7
Cloning and Sequencing of the Variable Regions of 806.077 Antibody Heavy and Light Chain Genes

7.1 Preparation of Cytoplasmic RNA

There are several procedures for the isolation of polyA+ mRNA from eukaryotic cells (Sambrook J., Fritsch E. F., Maniatis T., Molecular Cloning: A Laboratory Manual, Cold Spring Harbor Laboratory Press, Second Edition, 1989, Chapter 8, p3 herein referred to as "Maniatis"). In this particular case cytoplasmic RNA was prepared as described by Favoloro et al., Methods in Enzymology 65, 718–749, from a frozen hybridoma cell pellet containing 1×10$^9$ cells which had been stored at −80° C.

The cells were resuspended in 5 ml ice-cold lysis buffer (140 mM NaCl, 1.5 mM MgCl$_2$, 10 mM Tris-HCl pH 8.6 and 0.5% NP40 (a polyglycol ether nonionic detergent; Nonylphenoxy Polyethoxy Ethanol, Sigma Cat. No. 127087-87-0)) containing 400 u of a ribonuclease inhibitor (RNAguard; Pharmacia Cat. No. 27-0815-01) and vortexed for 10 s. This solution was overlayed on an equal volume of ice cold lysis buffer containing 24% (w/v) sucrose and 1% NP-40 and stored on ice for 5 min. The preparation was then centrifuged at 4000 rpm for 30 min at 4° C. in a bench top centrifuge (Sorval RT6000B) after which, the upper cytoplasmic phase was removed to an equal volume of 2×PK buffer (200 mM Tris (pH7.5), 25 mM EDTA, 300 mM NaCl and 2% (w/v) SDS). Proteinase K (Sigma, Cat No. P2308) was added to a final concentration of 200 μg/ml and the mixture incubated at 37° C. for 30 min.

The preparation was extracted with an equal volume of phenol/chloroform, the aqueous phase removed and 2.5 vol ethanol added and mixed. This solution was then stored at −20° C. overnight. RNA was collected by centrifugation (4000 rpm, 30 min at 4° C. in a bench top centrifuge, Sorval RT6000B), the supernatant decanted and the pellet dried in a vacuum dessicator after which it was dissolved in 250 μl diethylpyrocarbonate (DEPC)-treated water (prepared as described in Maniatis, referenced above). The RNA content was measured by spectrophotometry and the concentration calculated assuming an absorbance at 260 nm of 1=40 μg/ml.

7.2 Preparation of First Strand Variable Region cDNA

A number of methods for the synthesis of cDNA are reviewed in Maniatis (Chapter 8). The oligonucleotide primers used were mainly based on those proposed by Marks et al. J. Mol. Biol (1991) 222, 581–597. The cDNA in this case was prepared as described below. RNA (5 mg) was mixed in a microcentrifuge tube with 10 μl 5× reverse transcriptase buffer [250 mM Tris (pH8.3), 40 mM MgCl$_2$ and 50 mM DTT], 1 μl forward primer (25 μM), 10 μl 1.25 mM dNTPs, 5 μl 10 mM DTT, 0.5 μl RNAguard (Pharmacia) to which DEPC-treated H2O was added to obtain a volume of 50 μl. The reaction mix was heated to 70° C. for 10 min and then cooled slowly to 37° C., after which 100 u (0.5 μl) M-MLV reverse transcriptase (Pharmacia Cat. No. 27-0925-01) were added and the reaction incubated at 37° C. for 1 h. The forward primer used for the generation of the light chain cDNA was oligonucleotide CK2FOR (SEQ ID NO: 1) which is designed to hybridise to the CK constant region of murine kappa light chain genes. For the heavy chain cDNA the forward primer CG1FOR (SEQ ID NO: 2) was used which hybridises to the CH1 constant domain of murine IgG 1.

7.3 Amino Acid Sequencing

The heavy and light chains of the 806.077 antibodies were isolated by SDS-PAGE and Western blotting and submitted for N-terminal amino acid sequencing. The results showed that the N-terminus of the light chain was chemically blocked, however, sequence data was obtained for the first 34 N-terminal residues of the heavy chain (SEQ ID NO: 3). On the basis of this amino acid sequence a specific DNA back primer was designed for 806.077 heavy chain variable region PCR. This primer was called SP1back (SEQ ID NO: 7).

7.4 Isolation of Antibody Gene Fragments by PCR

Isolation of 806.077 heavy and light chain variable region genes was performed using the cDNA prepared as described above as template. General reaction conditions were as follows.

To 5 μl of the cDNA reaction was added 5 μl dNTPs (2.5 mM), 5 μl 10× Enzyme buffer (500 mM KCl, 100 mM Tris (pH8.3), 15 mM MgCl$_2$ and 0.1% gelatin), 1 μl of 25 pM/μl back primer, 1 μl of 25 pM/μl forward primer, 0.5 μl thermostable DNA polymerase and DEPC-treated water to obtain a volume of 50 μl. The PCR conditions were set for 25 cycles at 94° C. for 90 s; 55° C. for 60 s; 72° C. for 120 s, ending the last cycle with a further 72° C. for 10 min incubation.

Using the general reaction conditions, the forward primer used for the generation of the light chain cDNA was oligonucleotide CK2FOR (SEQ ID NO: 1) and the for the heavy chain cDNA oligonucleotide CG1FOR (SEQ ID NO: 2). A number of reactions using a variety of different back primers were performed for both the heavy and light chains to obtain desired specific PCR products.

In the case of the 806.077 light chain, on analysis a specific PCR product was obtained using the back primers VK1back (SEQ ID NO: 4) and VK4back (SEQ ID NO: 5). Similarly specific PCR products were obtained for the heavy chain using VH1back (SEQ ID NO: 6) and SP1back primers (SEQ ID NO: 7). Reaction products were analysed on a 2% agarose gel. Products of the expected size, were excised and the DNA purified.

7.5 Cloning of the PCR Products into Bluescript KS+ Vector

For each antibody fragment, both the 5' region (back primer) oligonucleotide and the 3' region (forward primers) introduced a restriction site. The discrete PCR products were for both the VH and VK PCR reactions were therefore able to be cloned into the Bluescript vector KS+ (Stratagene Cloning Systems) via the appropriate enzyme restriction sites using standard DNA manipulation methods (e.g. PCR products VH1back/CG1For was cloned via PstI/HindIII and VK4back/CK2For via SacI/HindIII). DNA was prepared from the clones obtained and rigorous sequencing of at least 12 clones of each construct performed using automated fluorescent sequencing equipment (Applied Biosystems). The sequences were reviewed, compared and aligned using suitable computer software. Consensus sequences for both the VH and VK genes were obtained and subsequently translated to their corresponding amino acid sequence.

The DNA and amino acid sequences obtained for the 806.077 light chain variable (VK) region are described in SEQ ID NO: 8 and SEQ ID NO: 9 respectively. The DNA and amino acid sequences obtained for the 806.077 heavy chain variable (VH) region are described in SEQ ID NO: 10 and SEQ ID NO: 11 respectively. A clone containing the light chain was designated VK4, and a clone containing the heavy chain sequnece was designated VH14A.

EXAMPLE 8

Construction of Chimaeric Light Chain and Heavy Chain Fd Genes

The heavy and light chain genes which had been cloned into Bluescript (VK4 and VH14A in Example 7) were isolated by PCR using primers which allowed specific amplification of only the variable region the appropriate genes but also introduced new unique enzyme restriction sites. These restriction sites enabled the variable region gene fragments to be cloned in frame with DNA fragments coding for both the appropriate antibody signal sequences and human constant regions. The signal and constant region sequences for the light and heavy chain Fd had each been previously cloned into pNG3 and pNG4, derivatives of the pSG5 Eukaryotic plasmid expression vector.

The vector pNG3 was prepared as follows. Plasmid pSG5 (Stratagene, Cat. No. 216201) was digested with SalI and XbaI to remove the existing SV40 promoter and polylinker sequence. A new polylinker was introduced by use of oligonucleotides SEQ NOS: 34 and 35 which were hybridised and cloned into the SalI and XbaI cut pSG5 plasmid to give plasmid pNG1. The pNG1 plasmid was cut with BglII and HindIII and the BglII-HindIII CMV promoter fragment from pcDNA3 (Invitrogen, Cat. No. V790-20) cloned into this site to give plasmid pNG2. Finally, the polyA region from pSG5 was isolated by PCR as described in Example 7, section 7.4 but using oligonucleotide sequences SEQ ID NOS: 36 and 37 with plasmid pSG5. The PCR product was cut with XmaI and BamHI, purified by electrophoresis on a 2% agarose gel, isolated (e.g. with GENECLEAN, see example 7) then ligated into the XmaI-BamHI cut pNG2 plasmid to give pNG3.

The pNG4 vector was prepared as follows. The pNG3 vector was further modified such that the SacI restriction enzyme recognition site in the cloned CMV promoter fragment was corrupted by changing the DNA sequence. This was achieved by the use of a two step PCR mutagenesis reaction using the pNG3 vector as a template. The PCR used-two complementary oligonucleotide primers (SEQ ID NOS: 38 and 39) to mutate the Sac I recognition sequence and 2 flanking primers (SEQ ID NOS: 40 and 41) for product amplification. Two Primer pairs (SEQ ID NOS: 38 and 41) and (SEQ ID NOS: 39 and 40) were used in a standard PCR reaction (as described in Example 7, section 7.4) to obtain the initial 2 PCR products, which were isolated by electrophoresis on 2% agarose gels. Equimolar amounts of each product were mixed and reamplified using the flanking primers (SEQ ID NOS: 40 and 41) under the standard PCR reaction conditions to splice together and amplify the final PCR product. This product was subsequently digested with the restriction enzymes NcoI and HindIII and cloned into the appropriately restricted and prepared pNG3 vector such that the mutated (SacI site minus) fragment replaced the original pNG3 NcoI-Hind III (SacI site plus) fragment. This new vector was named pNG4.

A clone of the 806.077 murine light chain in the Bluescript KS+vector (VK4) was taken and amplified using the oligonucleotide primers 077VK-UP (SEQ ID NO: 12) and 077VK-DOWN (SEQ ID NO: 13). Similarly a 806.077 heavy chain clone (VH14A) was amplified using 077VH-UP (SEQ ID NO: 14) and 077VH-DOWN (SEQ ID NO: 15). The PCR was performed as follows: To 100 ng of plasmid DNA was added 5 $\mu$l dNTPs (2.5 mM), 5 $\mu$l 10×Enzyme buffer (see above), 1 $\mu$l of 25 pM/$\mu$l back primer, 1 $\mu$l of 25 pM/$\mu$l forward primer, 0.5 $\mu$l thermostable DNA polymerase and DEPC-treated water to obtain a volume of 50 $\mu$l. The PCR conditions were set for 15 cycles at 94° C. for 90 s; 55° C. for 60 s; 72° C. for 120 s, ending the last cycle with a further 72° C. for 10 min incubation. The products were analysed on a 2% agarose gel. The DNA was purified and the DNA fragment digested with the relevant restriction enymes in preparation for subsequent vector cloning.

For secretion of antibody light chain, a double stranded DNA cassette which contained both the information for a Kozak recognition sequence and a light chain signal sequence was designed. The cassette consisted of two individual oligonucleotides (SEQ ID NOS: 42 and 43) which were hybridised and subsequently cloned between cloned between the HindIII and SacII restriction site of the pNG3 plasmid (which had been appropriately restricted and isolated using standard methodology) to create the vector pNG3-Vkss. The DNA sequence of SEQ ID NO: 46, which contains the sequence for the human light chain kappa constant region, was digested with XmaI and XhoI and inserted between the XhoI and XmaI cut pNG-Vkss plasmid to give the vector pNG3-Vkss-HuCk (NCIMB no. 40798). Furthermore, a neomycin resistance gene expression cassette was cloned into pNG3-Vkss-HuCk (from the pSG5 plasmid variant pSG5-Neo vector, supplied from S. Green, Zeneca Pharmaceuticals; alternative sources include vectors such as pMC1neo, Stratagene cat. no. 213201). The neomycin resistance gene expression cassette was cloned as an XbaI fragment and cloned into the XbaI site of the pNG3-Vkss-HuCk and the orientation was checked using restriction enzyme digestion. This gave rise to the plasmid pNG3-Vkss-HuCk-Neo (NCIMB 40799). The light chain gene sequence described above was inserted, in frame, by cloning directly between the SacII and XhoI sites of the pNG3-Vkss HuCk-neo vector. The PCR fragment obtained for the light chain gene was digested with SacII and XhoI restriction enzymes and cloned into the similarly restricted expression vector containing the VK signal and HuCK constant region coding sequences. The chimaeric 806.077 light chain sequence created is shown in SEQ ID NOS: 16 and 17.

Similarly, for secretion of antibody heavy chain, a double stranded DNA cassette which contained both the information for a Kozak recognition sequence and a heavy chain signal sequence was designed. The cassette consisted of two individual oligonucleotides (SEQ ID NOS: 44 and 45) which were hybridised and subsequently cloned between cloned between the HindIII and EcoRI restriction site of the pNG4 plasmid (which had been appropriately restricted and isolated using standard methodology) to create the vector pNG4-VHss. Heavy chain gene sequences could thus be inserted. in frame, by cloning directly between the EcoRI and SacI sites of the pNG4-VHss vector. The DNA sequence of SEQ ID NO: 47, which contains the coding sequence for human heavy chain IgG2CH1' constant region (SEQ ID NOS: 22 and 23) was digested with SacI and XmaI and cloned into pNG4-VHss cut with Sac and XmaI to give the vector pNG4-VHss-HuIgG2CH1' (NCIMB no. 40797). The PCR fragment obtained for the heavy chain gene was digested with EcoRI and SacI restriction enzymes and cloned into the similarly restricted expression vector pNG4-VHss-HuIgG2CH1' containing the VH signal and HuIgG2 CH1' constant region coding sequences. The chimaeric 806.077 HuIgG2 Fd chain sequence created is shown in SEQ ID NOS: 18 and 19.

In some instances it may be preferable to use other classes of chimaeric heavy chain Fd constructs. To this end, variants of the heavy chain vector are made containing HuIgG1CH1' (SEQ ID NOS: 20 and 21) or HuIgG3CH1' (SEQ ID NOS: 24 and 25) which are substituted for the HuIgG2CH1' (SEQ ID NOS: 22 and 23) gene. The sequences shown in SEQ ID NOS: 46 and 47 are prepared by a variety of methods including those described by Edwards (1987) Am. Biotech. Lab. 5, 38–44, Jayaraman et al. (1991) Proc. Natl. Acad. Sci. USA 88, 40844088, Foguet and Lubbert (1992) Biotechniques 13, 674–675 and Pierce (1994) Biotechniques 16, 708. Preferably, the sequences shown in SEQ ID NOS: 46 and 47 are prepared by a PCR method similar to that described by Jayaraman et al. (1991) Proc. Natl. Acad. Sci. USA 88, 40844088.

Once the individual heavy and light chain sequences were constructed a heavy chain Fd gene expression cassette (including both promoter and gene was excised as a BgIII/SalI fragment and cloned between into the BamHI/SalI sites of the light chain vector to produce a co-expression vector construct. This construct was transfected into NSO myeloma cells (ECACC No. 85110503) via standard techniques of electroporation and transfectants selected for the property of G418 resistance, a trait which is carried as a selectable marker on the expression plasmid construct.

Alternatively the complete heavy chain Fd and light chain genes may simply be excised from their respective vectors as HindIII/XmaI fragments and subsequently cloned into other expression vector systems of choice.

EXAMPLE 9
Hybridization Test of Nucleic Acid Variations of Specific Nucleic Acid Sequences
9.1 Hybridisation Test A method for detecting variant nucleic acids containing sequences related to specific 806.077 antibody sequences is described. These variant nucleic acids may be present in a variety of forms such as the DNA from bacterial colonies or the DNA/RNA from eukaryotic cells fixed on to a membrane as described above in the screening of a cDNA library or as fragments of purified nucleic acid separated by gel electrophoresis and then transferred to a suitable membrane as for the techniques of Northern (Maniatis et al, Chapter 7, p39) or Southern (Maniatis, chapter 9, p31) hybridisation.
9.2 Hybridisation Probe Hybridisation probes may be generated from any fragment of DNA or RNA encoding the specific 806.077 antibody nucleic sequence of interest, more specifically from the variable region, particularly the region encoding CDR3 of this region. A synthetic oligonucleotide or its complementary sequence can be used as a specific probe for the CDR3 encoding region.

A hybridisation probe can be generated from a synthetic oligonucleotide by addition of a radioactive 5' phospate group from $[\gamma$-$^{32}$P]ATP by the action of T4 polynucleotide kinase. 20 pmoles of the oligonucleotide are added to a 20 μl reaction containing 100 mM Tris, pH7.5, 10 mM MgCl$_2$, 0.1 mM spermidine, 20 mM dithiothreitol (DTT), 7.55 μM ATP, 55 μCi $[\gamma$-$^{32}$P]ATP and 2.5 u T4 polynucleotide kinase (Pharmacia Biotechnology Ltd, Uppsala, Sweden). The reaction is incubated for 30 minutes at 37° C. and then for 10 minutes at 70° C. prior to use in hybridisation. Methods for the generation of hybridisation probes from oligonucleotides (chapter 11) or from DNA and RNA fragments (chapter 10) are given in Maniatis. A number of proprietary kits are also available for these procedures.

9.3 Hybridisation Conditions

Filters containing the nucleic acid are pre-hybridised in 100 ml of a solution containing 6×SSC, 0.1% SDS and 0.25% dried skimmed milk (Marvel™) at 65° C. for a minimum of 1 hour in a suitable enclosed vessel. A proprietary hybridisation apparatus such as model HB-1 (Techne Ltd) provides reproducible conditions for the experiment.

The pre-hybridisation solution is then replaced by 10 ml of a probe solution containing 6×SSC, 0.1% SDS, 0.25% dried skimmed milk (e.g. Marvel™) and the oligonucleotide probe generated above. The filters are incubated in this solution for 5 minutes at 65° C. before allowing the temperature to fall gradually to below 30° C. The probe solution is then discarded and the filters washed in 100 ml 6×SSC, 0.1% SDS at room temperature for 5 minutes. Further washes are then made in fresh batches of the same solution at 30° C. and then in 10° C. increments up to 60° C. for 5 minutes per wash.

After washing, the filters are dried and used to expose an X-ray film such as Hyperfilm™ MP (Amersham International) at −70° C. in a light-tight film cassette using a fast tungstate intensifying screen to enhance the photographic image. The film is exposed for a suitable period (normally overnight) before developing to reveal the photographic image of the radio-active areas on the filters. Related nucleic acid sequences are identified by the presence of a photographic image compared to totally unrelated sequences which should not produce an image. Generally, related sequences will appear positive at the highest wash temperature (60° C.). However, related sequences may only show positive at the lower wash temperatures (50, 40 or 30° C.).

These results will also depend upon the nature of the probe used. Longer nucleic acid fragment probes will need to be hybridised for longer periods at high temperature but may remain bound to related sequences at higher wash temperatures and/or at lower salt concentrations. Shorter, mixed or degenerate oligonucleotide probes may require less stringent washing conditions such as lower temperatures and/or higher Na+concentrations. A discussion of the considerations for hybridisation protocols is provided in Maniatis (chapter 11).

EXAMPLE 10
Pharmaceutical Compositions

The following illustrates representative pharmaceutical dosage forms containing 806.077 antibody which may be used for therapy in combination with a suitable prodrug.
Injectable Solution for ADEPT A sterile aqueous solution, for injection, containing per ml of solution:

| | |
|---|---|
| 806.077 antibody - CPG2 conjugate | 1.0 mg |
| Sodium acetate trihydrate | 6.8 mg |
| Sodium chloride | 7.2 mg |
| Tween 20 | 0.05 mg |

A typical dose of conjugate for adult humans is 30 mg followed 3 days later by three 1 g doses of prodrug administered at hourly intervals. Suitable CPG2 conjugates are any one of those conjugates described in Examples 105 and 106. Conjugates with HCPB may replace the CPG2 conjugate in the table. Suitable HCPB conjugates are any one of those conjugates described in Examples 48–101.
Injectable Solution for Tumour Immunotherapy A sterile aqueous solution, for injection, containing per ml of solution:

| | |
|---|---|
| 806.077 antibody - B7 conjugate | 1.0 mg |
| Sodium acetate trihydrate | 6.8 mg |
| Sodium chloride | 7.2 mg |
| Tween 20 | 0.05 mg |

A typical dose of conjugate for adult humans is 30 mg. A suitable conjugate is described in Example 104.

EXAMPLE 11
Construction of Initial 806.077 Humanised Antibody Heavy and Light Chain Variable Region Genes Firstly an overview of the humanisation strategy is set out in the following text. The purpose of antibody humanisation is to combine the binding site of a non-human antibody into the supporting framework of a human antibody while maintaining the characteristic antigen binding affinity and specificity properties of the parent antibody. The feasibility of such antibody engineering is a consequence of the close sequence and structural homology of immunoglobulins from different mammalian species.

In its most basic form the approach involes the transfer of the six hypervariable regions or complementarity determing regions (CDRs) from one antibody Fv region to another, as first described in Jones etal Nature (1986) 321 522–525. However, experience has shown that in addition to the CDRs it is often necessary that amino acids in the antibody framework also need to be transferred for the process to be successful since such residues sometimes appear to contact and influence the conformation of the CDR loops.

In the case of the 806.077 antibody an "Initial" humanised version of the antibody was made which comprises the six murine CDRs and a number of framework residue substitutions. This construct was used as a template from which further variants (Examples 1247) were made by introducing additional "murine" residue substitutions. The rest of this Example describes the Initial humanised construct in detail.

The human antibody heavy chain variable region NEWM (Poljak, R. J et al (1974) PNAS 71 3440–3444) and the light chain kappa variable region REI (Palm, W and Hilschmann, N. Z. (1975) Physiol. Chem. 356 167–191 were chosen to form the acceptor human antibody framework. Numerous examples of successful humanisations-using this Fv framework have been described in the literature and the 3 dimensional structure of these two protein domains has been solved. Based on comparison of the murine 806.077 heavy and light chain variable region protein sequences with their closest related Kabat murine subgroup concensus sequences (and the individual sequence members) and the human NEWM and REI protein sequences, individual DNA sequences were designed to encode for the Initial humanised antibody which incorporated the murine CDRs and any additional framework substitutions considered to be of importance.

The murine 806.077 CDR sequences incorporated are described in SEQ ID NOs: 26; 27 and 28 for the light chain variable region and are found at positions 24–34 (CDR1), 50–56 (CDR2) and 89–97 (CDR3) repectively. The CDRs incorporated in the heavy chain variable region are described in SEQ ID NOs: 29,31 and 32 being at positions 31–35 (CDR1), 50–65 (CDR2), 95–102 (CDR3) respectively (using Kabat nomenclature). In the heavy chain variable region the additional changes V24A; S27F; T28N; F29I; S30K;.V71A; A92H; R93V (Kabat nomenclature) were made to the NEWM framework and in the light chain variable region no additional framework changes were made.

Individual synthetic DNA sequences were designed to encode for the initial version of the 806.077 humanised antibody heavy (806.077HuVH1) and light chain (806.077HuVK1) variable regions in which the CDRs and any additional framework residue changes were incorporated. The antibody variable gene sequences shown in SEQ ID NOS: 48 and 53 may be prepared by a variety of methods including those described by Edwards (1987) Am. Biotech. Lab. 5, 38–44, Jayaraman et al. (1991) Proc. Natl. Acad. Sci. USA 88, 40844088, Foguet and Lubbert (1992) Biotechniques 1, 674–675 and Pierce (1994) Biotechniques 16, 708. Preferably, the DNA sequences shown in SEQ ID NOS: 48 and 53 are prepared by a PCR method similar to that described by Jayaraman et al. (1991) Proc. Natl. Acad. Sci. USA 88, 4084–4088.

The humanised 806.077 antibody variable light chain gene sequence (SEQ ID NO: 49 and 50) was inserted, in frame, by cloning into the pNG3-Vkss-HuCK-Neo (NCIMB no. 40799) expression vector. To achieve this, the synthetic PCR DNA fragment encoding the humanised variable light chain gene (SEQ ID NO: 48) was digested with SacII and XhoI restriction enzymes and cloned into the similarly restricted pNG3-Vkss-HuCK-Neo vector which contained the VK signal sequence and HuCK constant region coding sequences. The DNA and protein sequence of completed humanised 806.077 light chain sequence (806.077HuVK1-HuCK) produced, together with its signal sequence, are shown in SEQ ID NOS: 51 and 52 respectively and the vector named pNG3-Vkss-806.077HuVK1-HuCK-Neo.

Similarly, for the humanised antibody heavy chain, the humanised variable heavy chain gene sequence SEQ ID NO: 54 and 55 was inserted, in frame, by cloning directly into the pNG4-VHss-HuIgG2CH1' (NCIMB no. 40797) expression vector. To achieve this, the synthetic PCR fragment obtained for the humanised heavy chain gene (SEQ ID NOS: 53) was digested with EcoRI and SacI restriction enzymes and cloned into the similarly restricted pNG4-VHss-HuIgG2CH1' vector which contained the VH signal sequence and HuIgG2 CH1' constant region coding sequences. The DNA and protein sequence of completed humanised 806.077 Fd heavy chain sequence (806.077HuVH1-HuIgG2 Fd) produced, together with its signal sequence, are shown in SEQ ID NOS: 56 and 57 respectively and the vector named pNG4-VHss-806.077HuVH1-HuIgG2 CH1'.

The Initial humanised antibody construct was produced by constructing a co-expression plasmid containing both 806.077 HuVK1 light chain and 806.077 HuVH1 heavy chain variable region antibody genes. The plasmid pNG3-Vkss-806.077HuVK1-HuCK-Neo vector, which contains the humanised light chain variable region HuVK1 (SEQ ID NOS: 49 and 50) was digested using the restriction enzymes BamHI and SalI and the vector run on a 1% agarose gel, the vector band was excised and purified. The plasmid pNG4-VHss-806.077HuVH1-HuIgG2 CH1' (which contains the humanised 806.077HuVH1 heavy chain variable region (SEQ ID NOS: 56 and 57)) was digested using the restriction enzymes BglII and SalI, the reaction run on a 2% agarose and the fragment band excised and purified. The DNA fragment recovered was subsequently ligated into the prepared pNG3-Vkss-806.077HuVK1-HuCK-Neo vector to produce clones of the desired HuVH1/HuVK1 co-expression vector.

These constructs were transfected into NSO myeloma cells (ECACC No. 85110503) via standard techniques of electroporation and transfectants selected for the property of G41 8 antibiotic resistance. The clones obtained were tested for both antibody expression in the anti-human antibody Fd ELISA and CEA binding ELISA assays described below.

For the CEA ELISA each well of a 96 well immunoplate (NUNC MAXISORB™) was coated with 50 ng CEA in 50 mM carbonate/bicarbonate coating buffer pH9.6 (buffer capsules—Sigma C3041) and incubated at 4° C. overnight. The plate was washed three times with PBS+0.05% Tween 20 and then blocked 150 μl per well of 1% BSA in PBS +0.05% Tween 20 for 1 hour at room temperature. The plate was washed as previously described, 100 μl of test sample added per well and incubated at room temperature for 2 hours. Again the plate was washed three times with PBS+ 0.05% Tween 20, 100 μl per well of a 11500 dilution of HRPO-labelled goat anti-human kappa antibody (Sigma A 7164) was added, in 1% BSA in PBS-Tween 20 and incubated at room temperature on a rocking platform for at least 1 hour. The plate was washed as before and then once more with PBS. To detect binding add 100 μl per well developing solution (one capsule of phosphate-citrate buffer—Sigma P4922-dissolved in 100 mls $H_2O$ to which is added one 30 mg tablet o-phenylenediamine dihydrochloride—Sigma P8412) and incubated for up to 15 minutes. The reaction was stopped by adding 75 μl 2M $H_2SO_4$, and absorbance read at 490 nm.

In the anti-human antibody Fd ELISA, each well of a 96 well immunoplate was coated with 1.2 μg sheep anti-human Fd antibody (Binding Site PC075) in 50 mM carbonate/bicarbonate coating buffer pH9.6 (buffer capsules—Sigma C3041) and incubated at 4° C. overnight. The plate was washed three times with PBS+0.05% Tween 20 and then blocked with 150 μl per well of 1% BSA in PBS+0.05% Tween 20 for 1 hour at room temperature. The plate was washed as previously described, 100 μl of test sample added per well and incubated at room temperature for 2 hours. Again the plate was washed three times with PBS+0.05% Tween 20, 1 0011 per well of HRPO-labelled goat anti-human kappa antibody (Sigma A 7164) was added in 1% BSA in PBS-Tween 20 and incubated at room temperature on a rocking platform for at least 1 hour. Wash plate as before and then once more with PBS. To detect binding, developing solution etc was added as described above for the CEA binding assay.

The clones found to show the best expression and CEA binding levels were selected for further expansion into 24 well plates and re-tested. The best clone according to these assay criteria was selected and expanded such that a one liter production was undertaken, which was seeded using a 1:10 dilution of a confluently grown culture (i.e. 100 mls into 900 mls of fresh culture medium) and the grown for a further 14 days. The human F(ab')$_2$ antibody fragment was then purified from the culture supernatant as described in Example 102.

EXAMPLES 12–38

Further Combinations of Humanised Heavy and Light Chain Variable Region Gene Variants: Construction of 806.077 Humanised Heavy and Light Variable Region Variants.

The Initial humanised 806.077 variable region genes were also used for the subsequent construction of further gene constructs which contained additional murine framework residues. Modifications of the gene sequences were achieved (in the majority of cases) by cassette mutagenesis. In this technique part of the original gene was removed via restriction with two appropriate unique enzymes from the complete plasmid vector and then replaced by a double stranded DNA cassette (consisting of two complementary oligonucleotides hybridised together to form a DNA fragment with the appropriate cohesive ends) by direct ligation into the prepared plasmid thus reconstituting the gene but now containing desired DNA changes. Further combinations of mutations within either the heavy or light chain could be also be produced by simple DNA fragment exchanges between the appropriate variants by utilising the available unique restriction enzyme sites. Three further variants of the humanised light chain variable region were produced in addition to the original sequence HuVK1 (SEQ ID NO: 49 and 50) and these were called HuVK2, HuVK3 and HuVK4 repectively. The light chain variable region variant HuVK2 was a modification of the original HuVK1 coding sequence in order to produce the amino acid change M4L (Kabat nomenclature), with the gene (SEQ ID NO: 49) being mutated by cassette mutagenesis. The plasmid pNG3-Vkss-806.077HuVK1-HuCK-Neo (which contains the complete humanised light chain (SEQ ID NOS: 49 and 50) was digested using the restriction enzymes SacII and NheI. The digest was then loaded on a 2% agarose gel and the excised fragment separated from the remaining vector. The vector DNA was then excised from the gel, recovered and stored at −20° C .until required. Two oligonucleotides (containing the desired base changes) were designed and synthesised (SEQ ID NO: 58 and 59). These two oligonucleotides were hybridised by adding 200 pmoles of each oligonucleotide into a total of 30 μl of $H_2O$, heating to 95° C. and allowing the solution to cool slowly to 30° C. 100 pmoles of the annealed DNA product was then ligated directly into the previously prepared vector. This DNA "cassette" exchange produced the desired HuVK2 DNA and protein sequence (SEQ ID NO: 60 and 61) already in place in the expression vector pNG3-Vkss-806.077HuVK2-HuCK-Neo.

Similarly, HuVK3 with the amino acid changes D1Q; Q3V; M4L (Kabat nomenclature) was constructed using synthetic oligonucleotides (SEQ ID NO: 62 and 63) to produce the desired HuVK3 DNA and protein sequence (SEQ ID NO: 64 and 65) again already in place in the expression vector pNG3-Vkss-806.077HuVK3-HuCK-Neo. The light chain variable region variant HuVK4 was produced by a different technique, as there were not unique restriction enzyme sites available close to the mutation site. HuVK4, with the amino acid change L47W, was produced by a PCR mutagenesis technique. The vector pNG3-806.077HuVK1-HuVK-Neo was used as the template for two PCR reactions (94° C., 90 sec; 55° C., 60 sec; 72° C., 120 sec for 15 cycles, all buffers, etc., as previously described). Reaction A used the synthetic oligonucleotide sequence primers SEQ ID NOS: 66 and 67 and reaction B the synthetic oligonucleotide sequence primers SEQ ID NOS: 68 and 69. The products of these PCR reactions (A and B) were fragments of length 535 base pairs and 205 base pairs respectively. These reaction products were run on a 2% agarose gel and separated from any background products. Bands of the expected size were excised from the gel and recovered. Mixtures of varying amounts of the products A and B were made and PCR reactions performed using the synthetic oligonucleotides SEQ ID NOS: 66 and 68. The resulting product (ca.700 base pairs) was digested with the restriction enzymes SacII and XhoI and the cleavage products separated on a 2% agarose gel. The band of the expected 310 base pairs size was excised from the gel and recovered. This fragment was then ligated into the vector pNG3-806.077HuVK1-HuVK-Neo vector (which had been previously cut with the restriction enzymes SacII/XhoI and subsequently isolated) and thus created the desired HuVK4 DNA and protein sequence (SEQ ID NO: 70 and 71) within the expression vector pNG3-Vkss-806.077HuVK4-HuCK-Neo.

Six further variants of the humanised heavy chain variable region were produced in addition to the original HuVH1 sequence (SEQ ID NO: 54 and 55) and these were called HuVH2 to HuVK7 respectively. The heavy chain variable region variant HuVH2 was a modification of the original HuVH1 coding sequence in order to produce the amino acid change G49A (Kabat nomenclature), with the gene (SEQ ID NO: 54) being mutated by cassette mutagenesis. The plasmid pNG4-VHss-806.077HuVH1-HuIgG2 CH1' (which contains the complete humanised, IgG2 heavy chain Fd (SEQ ID NOS: 56 and 57) was digested using the restriction enzymes StuI and NotI. The digest was then loaded on a 2% agarose gel and the excised fragment separated from the remaining vector. The vector DNA was then excised from the gel, recovered and stored at −20° C. until required. Two oligonucleotides were designed, synthesised (SEQ ID NO: 72 and 73), hybridised and the product ligated directly into the previously prepared vector. This DNA "cassette" exchange produced the desired HuVH2 DNA and protein sequence (SEQ ID NO: 74 and 75) already in place in the expression vector pNG4-VHss-806.077HuVH2-HuIgG2 CH1'.

Similarly, HuVH3 with the amino acid changes T73S; F78A (Kabat nomenclature) was constructed using synthetic oligonucleotides (SEQ ID NO: 76 and 77), however. in this case, the vector pNG4-VHss-806.077HuVH1-HuIgG2 CH1' was digested using the restriction enzymes NotI and SacII. The synthetic DNA cassette was ligated directly into the previously prepared vector to produce the desired HuVH3 DNA and protein sequence (SEQ ID NO: 78 and 79) in the expression vector pNG4-VHss-806.077HuVH3-HuIgG2 CH1'.

HuVH4 with the amino acid changes G49A; T73S; and F78A (Kabat nomenclature) combines the HuVH2 (SEQ ID NO: 74 and 75) and HuVH3 (SEQ ID NO: 78 and 79) variants. This was achieved by digesting the pNG4-VHss-806.077HuVH3-HuIgG2 CH1' vector with the enzymes NotI and NheI and isolating the ca. 200 base pairs NotI/NheI restriction fragment after separation on a 2% agarose gel. The fragment was recovered and subsequently ligated into the pNG4-VHss-806.077HuVH2-HuIgG2 CH1' vector (which had been digested with the same Not I and NheI restriction enzymes and the vector fragment purified). The resulting clones contained the desired HuVH4 DNA and protein sequence ((SEQ ID NO: 80 and 81) in the expression vector pNG4-VHss-806.077HuVH4-HuIgG2 CH1'.

HuVH5 with the amino acid changes V67A (Kabat nomenclature) was constructed using synthetic oligonucleotides (SEQ ID NO: 82 and 83). Again, the vector pNG4-VHss-806.077HuVH1-HuIgG2 CH1' was digested using the restriction enzymes NotI and SacII. The synthetic DNA cassette was ligated directly into the previously prepared vector to produce the desired HuVH5 DNA and protein sequence (SEQ ID NO: 84 and 85) in the expression vector pNG4-VHss-806.077HuVH5-HuIgG2 CH1'.

HuVH6 with the amino acid changes V67A;T73S and F78A (Kabat nomenclature) was constructed using synthetic oligonucleotides (SEQ ID NO: 86 and 87) and for this mutant the vector pNG4-VHss-806.077HuVH1-HuIgG2 CH1' was digested using the restriction enzymes NotI and SacII. The synthetic DNA cassette was ligated directly into the previously prepared vector to produce the desired HuVH6 DNA and protein sequence (SEQ ID NO: 88 and 89) in the expression vector pNG4-VHss-806.077HuVH6-HuIgG2 CH1'.

HuVH7 with the amino acid changes G49A; V69A; T73S; and F78A (Kabat nomenclature) combines the HuVH2 (SEQ ID NO: 74 and 75) and HuVH6 (SEQ ID NO: 88 and 89) variants. This was achieved by digesting the pNG4-VHss-806.077HuVH6-HuIgG2 CH1' vector with the enzymes NotI and NheI and isolating the ca. 200 base pairs NotI/NheI restriction fragment after separation on a 2% agarose gel. The fragment was recovered and ligated into the pNG4-VHss-806.077HuVH2-HuIgG2 CH1' vector (which had been digested with the same Not I and NheI restriction enzymes and the vector fragment purified). The resulting clones contained the desired HuVH7 DNA and protein sequence (SEQ ID NO: 90 and 91) in the expression vector pNG4-VHss-806.077HuVH7-HuIgG2 CH1'.

Combinations of such humanised heavy and light chain variable gene variants were made by excising the heavy chain Fd gene variant expression cassette (including both promoter and gene excised as a BglII/SalI fragment) and cloning this fragment into the BamHI/SalI sites of the light chain variant vector to produce a co-expression vector construct. A listing of the possible combinantions of variants based on the humanised heavy and light chain variants previously described is shown in the table below.

TABLE

Combinations of humanised heavy and light chain variable region variants.

| Example No. | Heavy chain variable region | SEQ ID NOS: | Light chain variable region | SEQ ID NOS: | Co-expression Plasmid Vector |
|---|---|---|---|---|---|
| 11 | HuVH1 | 54 and 55 | HuVK1 | 49 and 50 | pNG 806HuVH1/HuVK1/HuIgG2 |
| 12 | HuVH1 | 54 and 55 | HuVK2 | 60 and 61 | pNG 806HuVH1/HuVK2/HuIgG2 |
| 13 | HuVH1 | 54 and 55 | HuVK3 | 64 and 65 | pNG 806HuVH1/HuVK3/HuIgG2 |
| 14 | HuVH1 | 54 and 55 | HuVK4 | 70 and 71 | pNG 806HuVH1/HuVK4/HuIgG2 |
| 15 | HuVH2 | 74 and 75 | HuVK1 | 49 and 50 | pNG 806HuVH2(HuVK1/HuIgG2 |
| 16 | HuVH2 | 74 and 75 | HuVK2 | 60 and 61 | pNG 806HuVH2IHuVK2/HuIgG2 |
| 17 | HuVH2 | 74 and 75 | HuVK3 | 64 and 65 | pNG 806HuVH2/HuVK3/HuIgG2 |
| 18 | HuVH2 | 74 and 75 | HuVK4 | 70 and 71 | pNG 806HuVH2(HuVK4/HuIgG2 |
| 19 | HuVH3 | 78 and 79 | HuVK1 | 49 and 50 | pNG 806HuVH3/HuVK1/HuIgG2 |
| 20 | HuVH3 | 78 and 79 | HuVK2 | 60 and 61 | pNG 806HuVH3/HuVK2/HuIgG2 |
| 21 | HuVH3 | 78 and 79 | HuVK3 | 64 and 65 | pNG 806HuVH3/HuVK3/HuIgG2 |
| 22 | HuVH3 | 78 and 79 | HuVK4 | 70 and 71 | pNG 806HuVH3/HuVK4/Hu1gG2 |
| 23 | HuVH4 | 80 and 81 | HuVK1 | 49 and 50 | pNG 806HuVH4/HUVK1/HuIgG2 |
| 24 | HuVH4 | 80 and 81 | HuVK2 | 60 and 61 | pNG 806HuVH4/HuVK2/HuIgG2 |
| 25 | HuVH4 | 80 and 81 | HuVK3 | 64 and 65 | pNG 806HuVH4/HuVK3/HuIgG2 |
| 26 | HuVH4 | 80 and 81 | HuVK4 | 70 and 71 | pNG 806HuVH4/HuVK4/HuIgG2 |

TABLE-continued

Combinations of humanised heavy and light chain variable region variants.

| Example No. | Heavy chain variable region | SEQ ID NOS: | Light chain variable region | SEQ ID NOS: | Co-expression Plasmid Vector |
|---|---|---|---|---|---|
| 27 | HuVH5 | 84 and 85 | HuVK1 | 49 and 50 | pNG 806RuVH5/HuVK1/HuIgG2 |
| 28 | HuVH5 | 84 and 85 | HuVK2 | 60 and 61 | pNG 806HuVH5/HuVK2/HuIgG2 |
| 29 | HuVH5 | 84 and 85 | HuVK3 | 64 and 65 | pNG 806HuVH5/HuVK3/HuIgG2 |
| 30 | HuVH5 | 84 and 85 | HuVK4 | 70 and 71 | pNG 806HuVH5/HuVK4/HuIgG2 |
| 31 | HuVH6 | 88 and 89 | HuVK1 | 49 and 50 | pNG 806HuVH6/HuVK1/HuIgG2 |
| 32 | HuVH6 | 88 and 89 | HuVK2 | 60 and 61 | pNG 806HuVH6/HuVK2/HuIgG2 |
| 33 | HuVH6 | 88 and 89 | HuVK3 | 64 and 65 | pNG 806HuVH6/HuVK3/HuIgG2 |
| 34 | HuVH6 | 88 and 89 | HuVK4 | 70 and 71 | pNG 806HuVH6/HuVK4/HuIgG2 |
| 35 | HuVH7 | 90 and 91 | HuVK1 | 49 and 50 | pNG 806RuVH7/HuVK1/HuIgG2 |
| 36 | HuVH7 | 90 and 91 | HuVK2 | 60 and 61 | pNG 806HuVH7/HuVK2/HuIgG2 |
| 37 | HuVH7 | 90 and 91 | HuVK3 | 64 and 65 | pNG 806HuVH7/HuVK3/HuIgG2 |
| 38 | HuVH7 | 90 and 91 | HuVK4 | 70 and 71 | pNG 806HuVH7/HuVK4/HuIgG2 |

Analogously with Example 11, Example 14 was produced by constructing a co-expression plasmid containing both the 806.077 HuVK4 light chain and the 806.077 HuVH1 heavy chain variable region antibody genes. In this case the plasmid the pNG3-Vkss-806.077HuVK4-HuCK-Neo vector, which contains the humanised light chain variable region HuVK1 (SEQ ID NOS: 70 and 71) was digested using the restriction enzymes BamHI and SalI and the vector run on an 1% agarose gel and the vector band purified. The plasmid pNG4-VHss-806.077HuVH1-HuIgG2 CH1' (which contains the humanised 806;077 HuVH1 heavy chain variable region (SEQ ID NOS: 56 and 57) was digested using the restriction enzymes BglII and SalI, the reaction run on an 2% agarose and the fragment band excised and purified. The DNA fragment recovered was ligated into the prepared pNG3-Vkss-806.077HuVK4-HuCK-Neo vector to produce clones of the desired HuVH1/HuVK4 co-expression vector.

As described in Example 11, these constructs were transfected into NSO myeloma cells (ECACC No. 85110503) via standard techniques of electroporation and transfectants selected for the property of G418 resistance. The clones obtained were tested for both antibody expression in anti-human antibody Fd ELISA and CEA binding ELISA assays. Clones found to show the best expression and CEA binding levels were selected, expanded and product expressed. Human F(ab')$_2$ antibody fragment was then purified from the culture supernatant as described in Example 102.

EXAMPLE 39–47
Expression of Humanised F(ab')$_2$ Fragments With Various Classes of Human Heavy Chain Constant Regions Other classes of chimaeric heavy chain Fd constructs may be used. Accordingly, additional variants of the heavy chain vectors have been made which contain either HuIgG1CH1' (SEQ ID NOS: 20 and 21) or HuIgG3CH1' (SEQ ID NOS: 24 and 115), the constant regions of which are substituted for the HuIgG2CH1' gene (SEQ ID NOS: 22 and 23). The vectors created were pNG4-VHss-HuIgG1 CH1' and pNG4-VHss-HuIgG3 CH1' respectively. The heavy. chain antibody variable region in question can be excised from the appropriate pNG4-VHss-"VH variable region"-HuIgG2 CH1' plasmid by digestion with EcoRI and SacI restriction enzymes and cloned into the similarly restricted pNG4-VHss-HuIgG1CH1' or pNG4-VHss-HuIgG3 CH1' vector and thus produce a completed heavy chain Fd sequence. As described above, once the individual heavy and light chain sequences are constructed, a heavy chain Fd gene expression cassette (including both promoter and gene can be excised by restriction digestion and the fragment cloned between into the appropriate sites of the light chain vector to produce the final co-expression vector. The table below describes Examples 39–47 in which various heavy and light chain variable regions have been combined with a number of different classes of human heavy chain constant regions.

In Example 44, the vector pNG4-VHss-HuIgG3 CH1' was digested with the restriction enzymes EcoRI and SacI restriction enzymes and the vector fragment isolated as previously described. The HuVH1 heavy chain antibody variable region (SEQ ID NOS: 54 and 55) was excised from the pNG4-VHss-806.077HuVH1-HuIgG2 CH1' plasmid by digestion with EcoRI and SacI restriction enzymes and the fragment cloned into the similarly restricted pNG4-VHss-HuIgG3 CH1' vector to produce a completed humanised IgG3 heavy chain Fd sequence (SEQ ID NOS: 94 and 95) in the completed vector pNG4-VHss-806.077HuVH1-HuIgG3 CH1'. The heavy chain Fd gene expression cassette (including both promoter and gene) was excised as a BglII/SalI fragment and cloned into the BamHI/SalI sites of the light chain vector pNG3-Vkss-806.077HuVK1-HuCK-Neo (containing the HuVK1-HuCK humanised light chain SEQ ID NOS: 51 and 52) which had been digested using the restriction enzymes BamHI and SalI, run on an 1% agarose, the vector band purified. This produced a co-expression vector (pNG 806HuVH1/HuVK3/HuIgG3) from which the humanised 806.077HuVH1/HuVK1-HuIgG3/Kappa.Fd antibody fragment could be expressed.

TABLE

| Example No. | Humanised heavy chain | SEQ ID NOS | Humanised light chain | SEQ ID NOS | Co-expression Plasmid Vector |
|---|---|---|---|---|---|
| 39 | HuVH1-HuIgG1 | 92 and 93 | HuVK1-HuCK | 51 and 52 | Png 806HuVH1/HuVK1/HuIgG1 |

TABLE-continued

| Example No. | Humanised heavy chain | SEQ ID NOS | Humanised light chain | SEQ ID NOS | Co-expression Plasmid Vector |
|---|---|---|---|---|---|
| 40 | HuVH1-HuIgG2 | 56 and 57 | HuVK1-HuCK | 51 and 52 | pNG 806HuVH1/HuVK1/HuIgG2 |
| 41 | HuVH1-HuIgG3 | 94 and 95 | HuVK1-HuCK | 51 and 52 | pNG 806HuVH1/HuVK1/HuIgG3 |
| 42 | HuVH1-HuIgG1 | 92 and 93 | HuVK3-HuCK | 96 and 97 | pNG 806HuVH1/HuVK3/HuIgG1 |
| 43 | HuVH1-HuIgG2 | 56 and 57 | HuVK3-HuCK | 96 and 97 | pNG 806HuVH1/HuVK3/HuIgG2 |
| 44 | HuVH1-HuIgG3 | 94 and 95 | HuVK3-HuCK | 96 and 97 | pNG 806HuVH1/HuVK3/HuIgG3 |
| 45 | HuVH1-HuIgG1 | 92 and 93 | HuVK4-HuCK | 98 and 99 | pNG 806HuVH1/HuVK4/HuIgG1 |
| 46 | HuVH1-HuIgG2 | 56 and 57 | HuVK4-HuCK | 98 and 99 | pNG 806HuVH1/HuVK4/HuIgG2 |
| 47 | HuVH1-HuIgG3 | 94 and 95 | HuVK4-HuCK | 98 and 99 | pNG 806HuVH1/HuVK4/HuIgG3 |

In Example 47, the vector pNG4-VHss-HuIgG3 CH1' was digested with EcoRI and SacI restriction enzymes and the vector fragment isolated. The HuVH1 heavy chain antibody variable region (SEQ ID NOS: 54 and 55) was excised from the pNG4-VHss-HuVH1-HuIgG2 CH1' plasmid by digestion with EcoRI and SacI restriction enzymes and the fragment cloned into the similarly restricted pNG4-VHss-HuIgG3 CH1' vector. This produces a completed humanised IgG3 heavy chain Fd sequence (SEQ ID NOS: 94 and 95) in the completed vector pNG4-VHss-806.077HuVH1-HuIgG3 CH1'. The heavy chain Fd gene expression cassette (including both promoter and gene) was excised as a BglII/SalI fragment and cloned into the BamHI/SalI sites of the light chain vector pNG3-Vkss-806.077HuVK4-HuCK-Neo vector, (containing HuVK4-HuCK humanised light chain SEQ ID NOS: 98 and 99 ) which had been digested using the restriction enzymes BamHI and SalI, run on an 1% agarose, the vector band purified. This produced a co-expression vector construct pNG 806HuVH1/HuVK4/HuIgG3 from which the humanised HuVH1/HuVK1-HuIgG3/Kappa.Fd antibody fragment could be expressed.

The other Examples shown in the table above were all produced in a similar manner to that described in the Examples 44 and 47. However, in the case of the constructs containing human IgG1, the final co-expression vector construction was made by cloning the heavy chain Fd gene expression cassette (including both promoter and gene) excised as a BglII/BamHI fragment (because there is an internal SalI restriction site in the HuIgG1 CH1' constant region gene) and cloned into the BamHI site of the appropriately prepared light chain vector. In this case the orientation of the heavy chain cassette must be checked. This was achieved by restriction digestion (e.g. with the restriction enzyme Hind III) and agarose gel electrophoresis analysis in which the resulting fragment sizes were viewed relative to comparable fragments from a similarly digested HuIgG2 version (Examples 11–38). When the fragmentation patterns matched for both constructs we could be sure that the heavy chain cassette was in the correct orientation.

As previously described in Example 1, these constructs were transfected into NSO myeloma cells (ECACC No. 85110503) via standard techniques of electroporation and transfectants selected for the property of G418 resistance. The clones obtained were tested for both antibody expression in the anti-human antibody Fd ELISA and CEA binding ELISA assays and the clones found to show the best expression and CEA binding levels were selected, expanded and grown for gene expression. As before, the human F(ab')$_2$ antibody fragment was then purified from the culture supernatant as described in Example 102.

EXAMPLE 48

Preparation of Humanised 806.077 F(ab')$_2$-[A248S,G251T, D253K]HCPB Fusion Protein This Example describes the preparation of a gene encoding a humanised Fd heavy chain fragment of 806.077 linked to [A248S,G251T,D253K]HCPB and its co-expression with a gene encoding a humanised light chain of 806.077 and a gene encoding the pro domain of human carboxypeptidase B to give the F(ab')$_2$ protein with a molecule of [A248S, G251T,D253K]HCPB at the C-terminus of each of the heavy chain fragments. The constant and hinge regions of of the humanised Fd heavy chain fragment are derived from the human IgG3 antibody isotype. The expressed protein is also referred to as antibody-enzyme fusion protein.

(a) Preparation of a Gene Encoding Humanised Fd Heavy Chain Fragment of 806.077 Linked to [A248S, G251 T, D253K]HCPB and its Cloning into pEE6

A gene encoding humanised 806.077 Fd linked to [A248S,G251T,D253K]HCPB was generated by PCR from pZEN 1921 (Reference Example 2). A first PCR was set up with template pZEN1921 (2 ng) and oligonucleotides SEQ ID NO: 100 and SEQ ID NO: 101 (100 pM of each) in buffer (100 µl) containing 10 mM Tris-HCl (pH8.3), 50 mM KCL, 1.5 mM MgCl$_2$, 0.125 mM each of dATP, dCTP, dGTP and dTTP. The reaction was incubated at 94° C. for 5 min then thermostable DNA polymerase (2.5 u, 0.5 µl) was added and the mixture overlaid with mineral oil (100 µl) and the reaction mixture incubated at 94° C. for 1 min, 53° C. for 1 min and 72° C. for 2.5 min for 25 cycles, plus 10 min at 72° C. The PCR product of 536 base pairs was isolated by electrophoresis on a 1% agarose (Agarose type 1, Sigma A-6013) gel followed by excision of the band from the gel and isolation of the DNA fragment.

A second PCR was set up with template IgG3-pBSIIKS+ (8.7 ng, described in Reference Example 4) and oligonucleotides SEQ ID NO: 102 and SEQ ID NO: 103 and the 954 base pairs fragment isolated as described above. The products from the 2 PCRs were combined (either at 0.2, 1.0 or 5.0 ng/µl) in PCR buffer as described above. The mixture was incubated for at 94° C. for 5 min then 10 cycles at 94° C. for 1 min and 63° C. for 4 min. Oligos SEQ ID NOS: 101 and 102 (100 pM of each) in PCR buffer (50 µl) were added. After incubation at 94° C. for 3 min, the mixture was further incubated at 94° C. for 1.5 min, 53° C. for 2 min and 72° C. for 2 min for 25 cycles plus 10 min at 72° C. In this process, the G base at position 508 in SEQ ID NO: 115 was changed to an A base.

The PCR product of 1434 base pairs was isolated by electrophoresis on a 1% agarose gel, purified and digested with NheI (20 u) and XbaI (80 u) (New England Biolabs Inc.,) in a total volume of 100 µl containing 10 mM Tris HCl (pH7.9), 50 mM NaCl, 10 mM $MgCl_2$, 1 mM DTT and BSA (100 g/ml) for 4 h at 37° C. The resulting fragment was again isolated by electrophoresis on a 1% agarose gel and purified. In a similar digestion, vector pNG4-VHss-806.077huVH1-HuIgG2CH1' (10 µg; Example 11) was cut with NheI and XbaI then calf intestinal alkaline phosphatase (1 µl; New England Biolabs, 10 u/µl) was added to the digested plasmid to remove 5' phosphate groups and incubation continued at 37° C. for a further 30 minutes. Phosphatase activity was destroyed by incubation at 70° C. for 10 minutes. The NheI-XbaI cut plasmid was purified from an agarose gel. The NheI-XbaI digested PCR product from above (about 500 ng) was ligated with the above cut plasmid DNA (about 200 ng) in 20 µl of a solution containing 50 mM Tris-HCl (pH7.8), 10 mM $MgCl_2$, 10 mM DTT, 1 mM ATP, 50 µg/ml BSA and 400 u T4 DNA ligase (New England Biolabs, Inc) at 25° C. for 4 h. A 1 µl aliquot of the reaction was used to transform 20 µl of competent E. coli DH5α cells. Transformed cells were plated onto L-agar plus 100 g/ml ampicillin. Potential clones containing the gene for humanised 806.077 Fd-[A248S,G251T,D253K]HCPB were identified by PCR. Each clone was subjected to PCR as described above with oligonucleotides SEQ ID NOS: 104 and 105. A sample (10 µl) of the PCR reaction was analysed by electrophoresis on a 1% agarose gel. Clones containing the required gene were identified by the presence of a 512 base pairs PCR product. Clones producing the 512 base pairs band were used for DNA minipreps. The DNA samples were checked by digestion with HindIII and XbaI for the presence of 3751 base pairs and 1862 base pairs fragments. Clones containing these fragments on digestion of the DNA with HindIII and XbaI were used for large scale plasmid DNA preparation and the sequence of the insert confirmed by DNA sequence analysis. The sequence of the expected insert is shown in SEQ ID NO: 112 Of the clones examined above, 2 contained the expected sequence but with a single base mutation. Clone 54 (also designated pMF195) had an T base at position 605 in SEQ ID NO: 112 in place of the A base, whereas clone 68 (also designated pMF198) had a C base at position 1825 instead of the expected T base. The sequence shown in SEQ ID NO: 112 was prepared from pMF195 and and pMF198 by digesting both (10 µg of each) with XmaI (10 u) and XbaI (100 u) (New England Biolabs) in buffer (100 µl) containing 20 mM Tris acetate (pH7.9) 50 mM potassium acetate. 10 mM Mg acetate. 1 mM DTT and BSA (100 µg/ml). The 215 base pairs fragment from pMF195 and the vector fragment from pMF198 (following treatment with alkaline phosphatase) were isolated from a 1% agarose gel and ligated together as described previously. The ligation mix was used to transform competent DH5α. cells. The transformed cells were plated onto L agar plus ampicillin and resulting colonies screened by digestion of the DNA with XmaI and XbaI for the presence of 5400 base pairs and 215 base pairs fragments. Positive clones were used for large scale plasmid DNA preparation and the sequence of the insert confirmed by DNA sequence analysis. The plasmid containing the 806.077 Fd-[A248S,G251T,D253K]HCPB gene from clone number 102 was named pMF213. The HindIII-XbaI fragment from pMF213 was cloned into pEE6 [this is a derivative of pEE6.hCMV—Stephens and Cockett (1989) Nucleic Acids Research 17, 7110—in which a HindIII site upstream of the hCMV promoter has been converted to a BglII site] in DH5α (screened by PCR with oligonucleotides SEQ ID NOS: 106 and 107 for a 2228 base pairs insert) to give pMF221.

(b) Preparation of a Co-Expression Vector for Expression of Antibody-Enzyme Fusion Protein To generate vectors capable of expressing the antibody-enzyme fusion protein in eukaryotic cells, the GS-System™ (Celltech Biologics) was used (WO 87/04462, WO 89/01036, WO 86/05807 and WO 89/10404). The procedure requires cloning the humanised antibody light chain gene into the HindIII-XmaI region of vector pEE14. This vector is described by Bebbington in METHODS: A Companion to methods in Enzymology (1991) 2, 136–145. To construct the expression vector, plasmids pEE14 and pNG3-VKss-806.077HuVK4-HuCK-Neo (Example 14) were digested with HinIII and XmaI as described above. The appropriate vector (from pEE14) and insert (732 base pairs from pNG3-VKss-806.077HuVK4-HuCK-Neo) from each digest were isolated from a 1% agarose gel and ligated together and used to transform competent DH5α cells. The transformed cells were were plated onto L agar plus ampicillin (100 µg/ml). Colonies were screened by restriction analysis of isloated DNA for the presence of a 732 base pairs fragment on digestion of the DNA with HindIII and XmaI. Clones producing a 732 base pairs restriction fragment were used for large scale plasmid DNA preparation and the sequence of the insert confirmed by DNA sequence analysis. The plasmid containing the humanised light chain sequence of SEQ ID NO: 70 in pEE14 was named pEE14-806.077HuVK4-HuCK.

To make the co-expression vector, pMF221 (10 µg) was cut with BglII (20 u) and SalI (40 U) in buffer (100 µl) containing 10 mM Tris-HCl (pH 7.9). 150 mM NaCl, 10 mM $MgCl_2$, 1 mM DTT and BSA (100 µg/ml) and the 4560 base pairs fragment isolated by agarose gel electrophoresis and purified. Similarly, pEE14-806.077HuVK4-HuCK was cut with BamHI (40 u) and SalI (40 u) and the 9.95 kb vector fragment isolated and ligated to the BglII-SalI fragment from pMF221 and cloned into DH5α. Colonies were screened by PCR with 2 sets of oligonucleotides (SEQ ID NOS: 104 and 105, and SEQ ID NOS: 108 and 109). Clones giving PCR products of 185 base pairs and 525 base pairs respectively were characterised by DNA sequencing. A clone with the correct sequence was named pMF228—light chain/Fd-mutant HCPB co-expression vector in DH5α. The humanised Fd-mutant HCPB sequence is shown in SEQ ID NO: 113. Residues 1 to 19 are the signal sequence, residues 20 to 242 are the humanised variable and IgG3 CH1 region, residues 243 to 306 are the IgG3 hinge region and residues 307 to 613 are the mutant HCPB sequence with the changes at residues 248, 251 and 253 from the human HCPB sequence. The changes in the HCPB sequence occur in SEQ ID NO: 113 at postions 554 (Ser), 557 (Thr) and 559 (Lys) respectively.

(c) Preparation of a Vector for Expression of the Pro Domain of ProHCPB

A second eukaryotic expression plasmid, pEE12 containing a gene for the prepro sequence, for secretion of the pro domain with an additional C-terminal leucine residue (termed pro-L), of preproHCPB was prepared as described in Reference Example 17 of International Patent Application Number WO 96/20011. Plasmid pMF161 was prepared by PCR from pMF18 as described for the unmodified prepro sequence, but using oligonucleotides SEQ ID NOS: 110 and 111. The 359 base pairs fragment was cloned into pBluescript to give pMF141 and subsequently into pEE12 to give pMF161. The protein sequence of pro-L is shown in SEQ ID NO: 114.

(d) Expression of Antibody-Enzyme Fusion Protein in Eukaryotic Cells

For expression in eukaryotic cells, vectors containing genes capable of expressing the antibody enzyme-fusion protein (pMF228) and the pro-L sequence (pMF161) were co-transfected into COS-7 cells. COS cells are an African green monkey kidney cell line, CV-1, transformed with an origin-defective SV40 virus and have been widely used for short-term transient expression of a variety of proteins because of their capacity to replicate circular plasmids containing an SV40 origin of replication to very high copy number. There are two widely available COS cell clones, COS-1 and COS-7. The basic methodology for transfection of COS cells is described by Bebbington in Methods: A Companion to Methods in Enzymology (1991) 2, p. 141. For expression of HCPB, the plasmid vectors pMF48 and pMF67 (2 $\mu$g of each) were used to transfect the COS-7 cells ($2\times10^5$) in a six-well culture plate in 2 ml Dulbecco's Modified Eagle's Medium (DMEM) containing 10% heat inactivated foetal calf serum (FCS) by a method known as lipofection—cationic lipid-mediated delivery of polynucleotides [Felgner et al. in Methods: A Companion to Methods in Enzymology (1993) 5, 67–75]. The cells were incubated at 37° C. in a $CO_2$ incubator for 20 h. The mix of plasmid DNA in serum-free medium (200 $\mu$l) was mixed gently with LIPOFECTIN™ reagent (12 $\mu$l) and incubated at ambient temperature for 15 min. The cells were washed with serum-free medium (2 ml). Serum-free medium (600 $\mu$l) was added to the DNA/LIPOFECTIN™ and the mix overlaid onto the cells which were incubated at 37° C. for 6 h in a $CO_2$ incubator. The DNA containing medium was replaced with normal DMEM containing 10% FCS and the cells incubated as before for 72 h. Cell supernatants (diluted 1:10 with 0.025M Tris-HCl pH7.5; 125 $\mu$l) were analysed for activity against Hipp-Glu (5 h assay, in a total volume of 250 $\mu$l) essentially as described in Example 103. The diluted supernatant resulted in 18.4% hydrolysis of the Hipp-Glu substrate.

Alternatively, the unmodified pro domain (from plasmid pMF67 described in Reference Example 17 of International Patent Application Number WO 96/20011) can be used in place of the pro-L expression plasmid in the above experiment.

Large scale expression of proteins from COS cells is described by Ridder et al. (1995) in GENE 166, 273–276 and by Blasey et al. (1996) in CRYOTECHNOLOGY 18, 183–192.

For stable expression in CHO cells, the procedures described by Bebbington in METHODS: A Companion to Methods in Enzymology (1991) 2, 136–145 using GS selection with 25 $\mu$M and 50 $\mu$M MSX are followed. Alternatively, lipofection, essentially as described above for transfection of COS cells may also be used to transfect CHO cells. The cells are transfected with a mixture of plasmids pMF228 and pMF161 or pMF228 and pMF67. Supernatants from surviving colonies are screened by CEA ELISA (described in Example 11) and Western analysis (described below) for the presence of a 70kDa band corresponding to the required antibody enzyme fusion protein. Supernatants, suitably diluted, are also screened for enzyme activity as described in Example 103. Colonies expressing the desired antibody enzyme fusion protein are cultured at the required scale (see for Example the publication by M E Reff (1993) in Current Opinion in Biotechnology 4, 573–576 and references cited therein) and fusion protein purified from cell culture supernatant by one or more of the methods described in Example 102. (e) Western analysis Western blot analysis was performed as described as follows. Aliquots (20 $\mu$l) of each supernatant sample were mixed with an equal volume of sample buffer (62.5 mM Tris, pH6.8, 1% SDS, 10% sucrose and 0.05% bromophenol blue) with and without reductant. The samples were incubated at 65° C. for 10 minutes before electrophoresis on a 8–18% acrylamide gradient gel (EXCEL™ gel system from Pharmacia Biotechnology Products) in a MULTIPHOR™ II apparatus (LKB Produkter AB) according to the manufacturer's instructions. After electrophoresis, the separated proteins were transfered to a membrane (HYBOND™ C-Super, Amersham International) using a NOVABLOU™ apparatus (LKB Produkter AB) according to protocols provided by the manufacturer. After blotting, the membrane was air dried.

The presence of antibody fragments was detected by the use of an anti-human kappa antibody (Sigma A7164, goat anti-human Kappa light chain peroxidase conjugate) used at 1:2500 dilution. The presence of human antibody fragments was visualised using a chemiluminescence system (ECL™ detection system, Amersham International).

EXAMPLES 49–74

Preparation of other Humanised 806.077 F(ab')$_2$-Mutant HCPB Fusion Proteins

These Examples describe preparation of genes encoding humanised Fd heavy chain fragments of 806.077 linked to a mutant HCPB (D253K; G251T,D253K; A248S,G251T,D253K) and their co-expression with a gene encoding a humanised light chain of 806.077 and a gene encoding the pro domain of human carboxypeptidase B to give the F(ab')$_2$ protein with a molecule of mutant HCPB at the C-terminus of each of the heavy chain fragments. The constant and hinge regions of of the humanised Fd heavy chain fragment are derived from the human IgG1 or IgG2 or IgG3 antibody isotype. The expressed proteins are also referred to as antibody-enzyme fusion proteins.

The procedures described in Example 48 are repeated with the appropriate sequences derived from the table shown below. Oligonucleotides for PCR constructions and clone screening are readily derived from the appropriate sequences.

To change the mutant HCPB sequence, the PCR template, plasmid pZEN1921, in part (a) of Example 48 is replaced with pZEN1860 for [G251T,D253K]HCPB (described in Reference Example 1) or pICI1713 for [D253K]HCPB (described in International Patent Application Number WO 96/20011).

To change the antibody heavy chain constant and hinge region, the PCR template, vector IgG3-pBSIIKS+, in part (a) of Example 48 is replaced with pNG4-VHss-HulgG1CH1' (described in Examples 39–47) or pNG4-VHss-HulgG2CH1' (NCIMB No.40797).

To change the humanised antibody light chain sequence, the vector pEE14-806.077HuVK4-HuCK in part (b) of Example 48 is replaced with pEE14-806.077HuVK1-HuCK or pEE14-806.077HuVK3-HuCK. The vectors pEE14-806.077HuVK1-HuCK and pEE14-806.077HuVK3-HuCK are prepared as described for pEE14-806.077HuVK4-HuCK in part (b) of Example 48 but using the 732 base pairs HindIII-XmaI fragment from pNG-VHss-806.077HuVK1-Neo and pNG-VHss-806.077HuVK3-Neo respectively (described in Examples 12–38) in place of the HindIII-XmaI fragment from pNG-VHss-806.077HuVK4-Neo.

Antibody-enzyme fusion protein variants for each Example are shown in the table below.

TABLE

| Example No. | Humanised Heavy chain | Humanised Light chain | Mutant HCPB Enzyme |
|---|---|---|---|
| 49 | HuVH1-HuIgG3 | HuVK4-HuCK | [D253K]HCPB |
| 50 | HuVH1-HuIgG3 | HuVK4-HuCK | [G251T,D253K]HCPB |
| 51 | HuVH1-HuIgG3 | HuVK1-HuCK | [A248S,G251T,D253K]HCPB |
| 52 | HuVH1-HuIgG3 | HuVK1-HuCK | [D253K]HCPB |
| 53 | HuVH1-HuIgG3 | HuVK1-HuCK | [G251T,D253K]HCPB |
| 54 | HuVH1-HuIgG3 | HuVK3-HuCK | [A248S,G251T,D253K]HCPB |
| 55 | HuVH1-HuIgG3 | HuVK3-HuCK | [D253K]HCPB |
| 56 | HuVH1-HuIgG3 | HuVK3-HuCK | [G251T1D253K]HCPB |
| 57 | HuVH1-HuIgG1 | HuVK4-HuCK | [A248S,G251T,D253K]HCPB |
| 58 | HuVH1-HuIgG1 | HuVK4-HuCK | [D253K]HCPB |
| 59 | HuVH1-HuIgG1 | HuVK4-HuCK | [G251T,D253K]HCPB |
| 60 | HuVH1-HuIgG1 | HuVK1-HuCK | [A248S,G251T,D253K]HCPB |
| 61 | HuVH1-HuIgG1 | HuVK1-HuCK | [D253K]HCPB |
| 62 | HuVH1-HuIgG1 | HuVK1-HuCK | [G251T,D253K]HCPB |
| 63 | HuVH1-HuIgG1 | HuVK3-HuCK | [A248S,G251T,D253K]HCPB |
| 64 | HuVH1-HuIgG1 | HuVK3-HuCK | [D253K]HCPB |
| 65 | HuVH1-HuIgG1 | HuVK3-HuCK | [G251T,D253K]HCPB |
| 66 | HuVH1-HuIgG2 | HuVK4-HuCK | [A248S,G251T,D253K]HCPB |
| 67 | HuVH1-HuIgG2 | HuVK4-HuCK | [D253K]HCPB |
| 68 | HuVH1-HuIgG2 | HuVK4-HuCK | [G251T,D253K]HCPB |
| 69 | HuVH1-HuIgG2 | HuVK1-HuCK | [A248S,G251T,D253K]HCPB |
| 70 | HuVH1-HuIgG2 | HuVK1-HuCK | [D253K]HCPB |
| 71 | HuVH1-HuIgG2 | HuVK1-HuCK | [G251T,D253K]HCPB |
| 72 | HuVH1-HuIgG2 | HuVK3-HuCK | [A248S,G251T,D253]HCPB |
| 73 | HuVH1-HuIgG2 | HuVK3-HuCK | [D253K]HCPB |
| 74 | HuVH1-HuIgG2 | HuVK3-HuCK | [G251T,D253K]HCPB |

EXAMPLE 75
Preparation of [A248S,G251T,D253K]HCPB-(Humanised 806.077)F(ab')$_2$ Fusion Protein This Example describes the preparation of a gene encoding pro-[A248S,G25 1T,D253K]HCPB linked to a humanised (version 1 VH with Human IgG3) Fd heavy fragment of antibody 806.077, and its co-expression with a gene encoding a humanised light chain (version 4 VK with CK) of the 806.077 antibody. This gives the F(ab')$_2$ protein with a molecule of the pro-[A248S,G25 1 T,D253K]HCPB at the N-terminus of each of the heavy chain fragments. The enzyme is activated by the enzymatic removal of the pro domain using trypsin.

Standard molecular biology techniques, such as restriction enzyme digestion, ligation, kinase reactions, dephosphorylation, polymerase chain reaction (PCR), bacterial transformations, gel electrophoresis, buffer preparation and DNA generation, purification and isolation, were carried out as described by Maniatis et al., (1989) Molecular Cloning, A Laboratory Manual; Second edition: Cold Spring Harbor Laboratory, Cold Spring Harbor, N.Y., or following the recommended procedures of manufacturers of specific products. In most cases enzymes were purchased from New England BioLabs, but other suppliers, and equivalent procedures may be used. Oligonucleotide sequences were prepared in an Applied Biosystems 380A DNA synthesiser from 5'dimethoxytrityl base-protected nucleoside-2-cyanoethyl-N,N'-di-isopropyl-phosphoramidites and protected nucleoside linked to controlled-pore glass supports on a 0.2 $\mu$mol scale, according to the protocols supplied by Applied Biosystems Inc.

Mutants of HCPB, native HCPB and HCPB fusion proteins were assayed for their ability to convert hippuryl-L-glutamic acid or hippuryl-L-arginine acid to hippuric acid using an HPLC based assay as described in Example 103 or International Patent Application Number WO 96/20011 Example 20.

Immunoassay techniques were carried out using methods based on those described by Tijssen, (1985) Practice and Theory of Enzyme Immunoassays, Laboratory Techniques in Biochemistry and Molecular Biology Volume 15, Elsevier Science Publishers, Amsterdam, or following the recommended procedures of manufacturers of specific products.

To generate plasmids capable of expressing the antibody-enzyme fusion protein in eukaryotic cells the GS-System (Celltech Biologics) was used (details in International Patent Application Numbers WO 87/04462, WO 89/01036, WO 86/05807 and WO 89/10404) with the two plasmids pEE6 (a derivative of pEE6.hCMV in which the HindIII restriction site upstream of the hCMV promoter has been converted to a BglII site {Stephens and Cockett, 1989, Nucleic Acids Research, 17, 71 10}) and pEE12 (a derivative of pSV2.GS with a number of restriction sites removed {Bebbington et al, 1992, Bio/Technology, 10. 169}).

a) Cloning Pre-Pro-HCPB up to Restriction Enzyme XmaI Cut Site (Position 1048 in SEQ ID NO: 124)

Double stranded DNA of plasmid pMF18 (as described in International Patent application Number WO 96/20011 Reference Example 19), a construct consisting of pre-pro-HCPB cloned into vector pBluescript II KS+(Stratagene), was prepared using standard DNA technology (Qiagen plasmid kit or similar), and restriction digested with HindIII and XmaI enzymes, being very careful to ensure complete digestion. Restriction enzyme HindIII cuts the pMF18 plasmid just prior to the start of the pre-sequence of the HCPB gene, and XmaI cuts at the codon for amino acid 240 (proline) of the mature protein, the HindIII to XmaI DNA piece is referred to as the pre-pro-HCPB fragment. DNA of the correct size, containing the pre-pro-HCPB fragment (about 1061 base pairs) was purified.

Double stranded DNA of plasmid vector pUC19 (New England BioLabs) was prepared, restriction digested with HindIII and XmaI, and purified (about 2651 base pairs) in a similar manner to the pre-pro-HCPB fragment. Ligation mixes were prepared to clone the HCPB gene fragment into the pUC19 vector, using a molar ratio of about 1 vector to 2.5 insert, and a final DNA concentration of about 2.5 ng/ml, in the presence of T4 DNA ligase. 1 mM ATP and enzyme buffer. Following the ligation reaction the DNA mixture was used to transform E.coli strain DH5α. Cell aliquots were plated on L-agar nutrient media containing 100 μg/ml ampicillin as selection for plasmid vector, and incubated overnight at 37° C. A number of colonies were picked and used for mini-preparations of double stranded plasmid DNA. These DNA samples were analysed by restriction enzyme digestion, and a construct of the correct configuration identified. This plasmid containing the pre-pro-HCPB fragment up to the XmaI site in the mature gene is known as pCF003.

b) Cloning [A248S,G251T,D253K]HCPB from Position G241+Linker and 5 Amino Acids of VH To separate the HCPB from the Fd sequence a neutral peptide linker consisting of (Glycine-Glycine-Glycine-Serine)$_3$ was introduced into the sequence during the PCR. In order to generate the fragment of the mutant [A248S, G251T,D253K]HCPB sequence (as documented in Reference Example 2) and add the peptide linker and the first 5 amino acids of the humanised 806.077 VH, a PCR was set up using 100 pMols of primers CME 00971 and CME 00972 (SEQ ID NOs: 122 and 123) in the presence of approximately 5 ng of pZen1921 DNA, dNTPs to a final concentration of 200 μM, Taq polymerase reaction buffer, and 2.5 U of Taq polymerase in a final volume of 100 μl. The mixture was heated at 94° C. for 10 minutes prior to addition to the Taq enzyme, and the PCR incubation was carried out using 30 cycles of 94° C. for 1.5 minutes, 55° C. for 2 minutes, and 72° C. for 2 minutes, followed by a single incubation of 72° C. for 10 minutes at the end of the reaction. The PCR product containing the [A248S,G25 1 T,D253K]HCPB fragment (about 298 base pairs) was analysed for DNA of the correct size by agarose gel electrophoresis and found to contain predominantly a band of the correct size. The remainder of the product from the reaction mix was purified and separated from excess reagents using a microconcentrator column (Centricon™ 100, Amicon), followed by DNA isolation by ethanol/sodium acetate precipitation, centrifugation, vacuum drying and re-suspension in distilled water. The isolated DNA was restriction digested with enzymes XmaI and EcoRI, and a band of the correct size (about 271 base pairs) purified.

Double stranded DNA of plasmid pCF003 (described above) prepared using standard DNA technology (Qiagen plasmid kits or similar), was restriction digested with XmaI and EcoRI enzymes, and a band of the correct size (about 2696 base pairs) purified.

Ligation mixes were prepared to clone the mutant HCPB gene fragment into the vector, using a molar ratio of about 1 vector to 2.5 insert (1 pCF003 to 2.5 [A248S,G251T, D253K]HCPB fragment PCR product), and a final DNA concentration of about 2.5 ng/ml, in the presence of T4 DNA ligase, 1 mM ATP and enzyme buffer. Following the ligation reaction the DNA mixture was used to transform *E.coli* strain DH5α. Cell aliquots were plated on L-agar nutrient media containing 100 μg/ml ampicillin as selection for plasmid vector, and incubated overnight at 37° C. About 200 colonies were picked and plated onto duplicate sterile nitrocellulose filters (Schleicher and Schull), pre-wet on plates of L-agar nutrient media containing 100 μg/ml ampicillin as selection for plasmid vector, and incubated overnight at 37° C. One duplicate plate was stored at 4° C., and acted as a source of live cells for the colonies, the other plate was treated to denature and fix the DNA from the individual colonies to the nitro-cellulose. The nitro-cellulose filter was removed from the agar plate and placed in succession onto filter papers (Whatman) soaked in: 1.10% SDS for 2 minutes; 2. 0.5M NaOH, 1.5M NaCl for 7 minutes; 3. 0.5M NaOH, 1.5M NaCl for 4 minutes; 4. 0.5M NaOH, 1.5M NaCl for 2 minutes; 5. 0.5M Tris pH7.4, 1.5M NaCl for 2 minutes; and 6. 2×SSC (standard saline citrate) for 2 minutes. The filter was then placed on a filter paper (Whatman) soaked in 10×SSC and the denatured DNA was crossed linked to the nitro-cellulose by ultra violet light treatment (Spectrolinker XL-1500 UV crosslinker). The filters were allowed to air dry at room temperature, and were then pre-hybridised at 60° C. for one hour in a solution of 6×SSC with gentle agitation (for example using a Techne HB-1D hybridizer). Note pre-hybridisation blocks non-specific DNA binding sites on the filters.

In order to determine which colonies contain DNA inserts of interest the DNA cross-linked to the nitro-cellulose filter was hybridised with a radio-labelled $^{32}$P-DNA probe prepared from the [A248S,G251T,D253K]HCPB purified PCR DNA fragment (see above). About 50 ng of DNA was labelled with 50 μCi of $^{32}$P-dCTP (>300 μCi/mMol) using T7 DNA polymerase in a total volume of 50 μl (Pharmacia T7 Quickprime kit), and the reaction allowed to proceed for 15 minutes at 37° C. The labelled probe was heated to 95° C. for 2 minutes, to denature the double stranded DNA, immediately added to 10 ml of 6×SSC at 60° C., and this solution was used to replace the pre-hybridisation solution on the filters. Incubation with gentle agitation was continued for about 3 hours at 60° C. After this time the hybridisation solution was drained off, and the filters were washed twice at 60° C. in 2×SSC for 15 minutes each time. Filters were then gently blotted dry, covered with cling film (Saran™ wrap or similar), and exposed against X-ray film (for example Kodak X-OMAT-ARS™) overnight at room temperature. Following development of the film, colonies containing inserts of interest were identified as those which gave the strongest exposure (darkest spots) on the X-ray film. In this series of experiments about 15% of the colonies gave positive hybridisation. From this 12 colonies were chosen for further screening. These colonies were picked from the duplicate filter, streaked and maintained on L-agar nutrient media containing 100 μg/ml ampicillin, and grown in L-broth nutrient media containing 100 μg/ml ampicillin.

The selected colonies were used for mini-preparations of double stranded plasmid DNA. These DNA samples were analysed by restriction enzyme digestion, and constructs of the correct configuration identified. In order to ensure that no changes to the DNA sequence had been introduced during the PCR a number of clones with correct restriction mapping were taken for DNA preparation using standard technology (Qiagen plasmid kits or similar), and the inserts sequenced using several separate oligonucleotide primers. A construct of the correct sequence was identified, and this plasmid containing the pre-pro-[A248S,G251T,D253K]HCPB-linker-humanised 806.077 VH gene up to the PstI site (at amino acid 5)(position 1301 in SEQ ID NO: 124) is termed pCF004.

c. Cloning Humanised 806.077 Fd

Double stranded DNA of plasmid pNG4-VHss-HuVH1-806.077-IgG3CH1', a construct consisting of the humanised 806.077 version 1 VH with human IgG3 CH1 and hinge region cloned into vector pNG4 (see Example 44), was prepared using standard DNA technology (Qiagen plasmid kit or similar), and restriction digested with PstI and XmaI enzymes. DNA of the correct size, containing the humanised 806.077 Fd fragment (about 854 base pairs) was purified. Double stranded DNA of plasmid vector pUC19 (New England BioLabs) was prepared, restriction digested with PstI and XmaI, and purified (about 2659 base pairs) in a similar manner to the humanised 806.077 Fd fragment.

Aliquots of both restricted and purified DNA samples were checked for purity and concentration estimation using agarose gel electrophoresis compared with known standards. From these estimates ligation mixes were prepared to clone the humanised 806.077 Fd gene fragment into the pUC19 vector, using a molar ratio of about 1 vector to 2.5 insert, and a final DNA concentration of about 2.5 ng/ml, in the presence of T4 DNA ligase, 1 mM ATP and enzyme buffer.

Following the ligation reaction the DNA mixture was used to transform *E.coli* strain DH5α. Cell aliquots were plated on L-agar nutrient media containing 100 μg/ml ampicillin as selection for plasmid vector, and incubated overnight at 37° C. A number of colonies were picked and used for mini-preparations of double stranded plasmid DNA. These DNA samples were analysed by restriction enzyme digestion, and a construct of the correct configuration identified. This plasmid containing the humanised 806.077 Fd fragment from the PstI site to the XmaI site is known as pCF005.

d) Cloning Humanised 806.077 Fd into Pre-Pro-[A248S, G251T,D253K]HCPB-Linker Construct Double stranded DNA of plasmid pCF005 (as documented above), was prepared using standard DNA technology (Qiagen plasmid kit or similar), and restriction digested with PstI and EcoRI enzymes. DNA of the correct size, containing the humanised 806.077 Fd fragment (about 870 base pairs) was purified. Double stranded DNA of plasmid vector pCF004 (as documented above) was prepared, restriction digested with PstI and EcoRI, and purified (about 3950 base pairs) in a similar manner to the humanised 806.077 Fd fragment. Ligation mixes were prepared to clone the humanised 806.077 Fd gene fragment into the pCF004 vector, using a molar ratio of about 1 vector to 2.5 insert, and a final DNA concentration of about 2.5 ng/μl, in the presence of T4 DNA ligase, 1 mM ATP and enzyme buffer.

Following the ligation reaction, the DNA mixture was used to transform *E.coli* strain DH5α. Cell aliquots were plated on L-agar nutrient media containing 100 μg/ml ampicillin as selection for plasmid vector, and incubated overnight at 37° C. A number of colonies were picked and used for mini-preparations of double stranded plasmid DNA. These DNA samples were analysed by restriction enzyme digestion, and a construct of the correct configuration identified. This plasmid containing the pre-pro-[A248S,G251T, D253K]HCPB-Linker-Fd(humanised 806.077) in pUC19 is known as pCF006.

e) Cloning Pre-Pro-[A248S,G251 T,D253K]HCPB-Linker-(Humanised 806.077)Fd into pEE6 hCMV Vector Double stranded DNA of plasmid pCF006 (as documented above), was prepared using standard DNA technology (Qiagen plasmid kit or similar), and restriction digested with HindIII and EcoRI enzymes. DNA of the correct size, containing the fusion protein (about 2185 base pairs) was purified.

Double stranded DNA of plasmid vector pEE6 (as documented above) was prepared, restriction digested with HindIII and EcoRI, and purified (about 4775 base pairs) in a similar manner to the fusion protein. Ligation mixes were prepared to clone the humanised 806.077 Fd fusion protein into the pEE6 vector, using a molar ratio of about 1 vector to 2.5 insert, and a final DNA concentration of about 2.5 ng/μl, in the presence of T4 DNA ligase, 1 mM ATP and enzyme buffer. Following the ligation reaction the DNA mixture was used to transform *E.coli* strain DH5α. Cell aliquots were plated on L-agar nutrient media containing 100 μg/ml ampicillin as selection for plasmid vector, and incubated overnight at 37° C. A number of colonies were picked and used for mini-preparations of double stranded plasmid DNA. These DNA samples were analysed by restriction enzyme digestion, and a construct of the correct configuration identified. This plasmid containing the pre-pro-[A248S,G251T,D253K]HCPB-Linker-Fd(humanised 806.077) in pEE6 is known as pCF007.

f) Cloning Humanised 806.077 Light Chain Version 4 into pEE12 Vector

Double stranded DNA of plasmid pNG3-VKss-806.077-HuVK4-HuCK-Neo. a construct consisting of the humanised 806.077 version HuVK4 with human CK cloned into vector pNG3 (see Examples 12–38), was prepared using standard DNA technology (Qiagen plasmid kit or similar), and restriction digested with HindIII and EcoRI enzymes. DNA of the correct size, containing the humanised 806.077 light chain (about 2022 base pairs) was purified. Double stranded DNA of plasmid vector pEE12 was prepared, restriction digested with HindIII and EcoRI, and purified (about 7085 base pairs) in a similar manner to the humanised 806.077 light chain. Ligation mixes were prepared to clone the humanised 806.077 light chain into the pEE12 vector, using a molar ratio of about 1 vector to 2.5 insert, and a final DNA concentration of about 2.5 ng/μl, in the presence of T4 DNA ligase, 1 mM ATP and enzyme buffer. Following the ligation reaction the DNA mixture was used to transform *E.coli* strain DH5α. Cell aliquots were plated on L-agar nutrient media containing 100 μg/ml ampicillin as selection for plasmid vector, and incubated overnight at 37° C. A number of colonies were picked and used for mini-preparations of double stranded plasmid DNA. These DNA samples were analysed by restriction enzyme digestion, and a construct of the correct configuration identified. This plasmid containing the humanised 806.077 light chain version 4 is known as pCF008/4.

g) Cloning CMVp-Pre-Pro-[A248S, G251 T, D253K]HCPB-Linker-Humanised 806. 077)Fd into pCF008/4.

Figure 2:
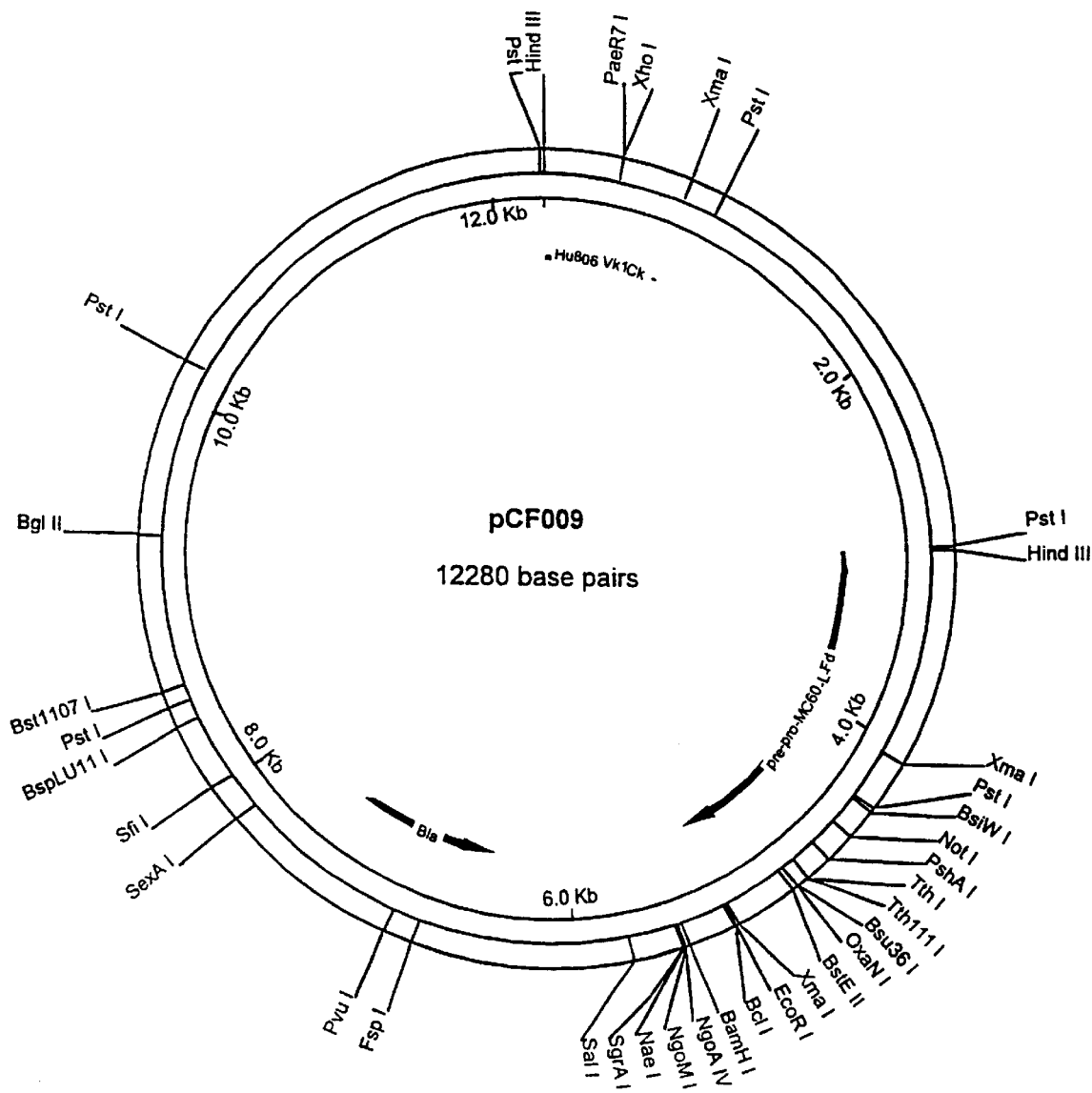
FIG. 2 shows a plasmid map of pCF009.

Double stranded DNA of plasmid pCF007 (as documented above), was prepared using standard DNA technology (Qiagen plasmid kit or similar), and restriction digested with BglII and SalI enzymes. Restriction enzyme BglII cuts the pCF007 plasmid prior to the start of the CMV MIE leader, promoter and gene for the fusion protein. Restriction enzyme SalI cuts about 520 base pairs after the stop codons of the mature protein. DNA of the correct size, containing the fusion protein (about 4844 base pairs) was purified. Double stranded DNA of plasmid vector pCF008/4 was prepared, restriction digested with BamHI and SalI, and purified (about 7436 base pairs) in a similar manner to the fusion protein. Ligation mixes were prepared to clone the [A248S,G251T,D253K]HCPB-linker-(humanised 806.077) Fd fusion gene into the pCF008/4 vector, using a molar ratio of about 1 vector to 2.5 insert, and a final DNA concentration of about 2.5 ng/μl, in the presence of T4 DNA ligase, 1 mM ATP and enzyme buffer. Following the ligation reaction the DNA mixture was used to transform *E.coli* strain DH5α. Cell aliquots were plated on L-agar nutrient media containing 100 μg/ml ampicillin as selection for plasmid vector, and incubated overnight at 37° C. A number of colonies were picked and used for mini-preparations of double stranded plasmid DNA. These DNA samples were analysed by restriction enzyme digestion, and a construct of the correct configuration identified. This plasmid containing genes for pro-[A248S,G251T,D253K]HCPB-Linker-F(ab')$_2$ (humanised 806.077 antibody) in the GS expression vector pEE12 is known as pCF009 and a plasmid map is shown in FIG. 2. The DNA and amino acid sequences of the light chain HuVK4 are shown in SEQ ID NOs: 70 and 71. The DNA sequence of the pre-pro-[A248S,G251T,D253K] HCPB-linker-Fd(Humanised 806.077) is shown in SEQ ID NO: 124 and the corresponding amino acid sequence in SEQ ID NO: 125.

h) Expression of Pro-[Mutant]HCPB-Linker-F(ab')$_2$ (Humanised 806.077) from Mouse Myeloma Cells.

The following method has been used for myeloma expression of all (D253K and G251T,D253K and A248S,G251T, D253K) mutant pro-HCPB enzyme fusion proteins. The preferred mouse myeloma cell line is NS0 (Galfre and Milstein, 1981, Methods in Enzymol., 73, 346), and is available form the European Collection of Animal Cell Cultures, PHLS CAMR, Porton Down, Salisbury, Wiltshire, SP4 0JG (ECACC catalogue number 85110503). These cells were grown in Dulbecco's Modified Eagle Medium (DMEM; Gibco/BRL) containing 10% heat inactivated foetal calf serum (FCS).

For expression of pro-[A248S,G251T,D253K]HCPB-linker-F(ab')$_2$(humanised 806.077) two plasmids were used, pCF009 (described above) and pRc/RSV (from Invitrogen, Cat no. V780-20) which contains the neomycin resistance gene for selection of G418 resistant stable cell lines. About 5 μg of each plasmid (from 0.5 to 10 μg) were used to transfect approximately 8×10⁶ NS0 cells by the method of lipofection (Felgner et al., in Methods: A Companion to Methods in Enzymology, 1993, 5, 67–75) which involves the cationic lipid mediated delivery of polynucleotides into eukaryotic cells. The cells were harvested by centrifugation, washed with serum free medium (30 ml), resuspended in 800 μl of medium and kept at 37° C. in a tissue culture flask until the DNA was added. Serum-free medium (450 μl) was mixed gently with LIPOFECTIN™ reagent (5041) and incubated at room temperature for 30 to 45 minutes. This mixture was added to 500 μl of medium containing the plasmid DNA mixture (in less than 100 μl) and left at room temperature for 15 minutes. Serum free medium (600 μl) was added to the plasmid DNA-LIPOFECTIN™ mixture, and the complex added to the cells which were incubated for about 5 hours at 37° C. in a CO$_2$ incubator. The DNA containing medium was then replaced with normal DMEM medium (8 ml) containing 10% FCS and the cells incubated overnight. The medium was then again replaced with normal DMEM medium (8 ml) containing 10% FCS and the cells incubated as previously without selection for 24 hours. At the end of this period the medium was changed to DMEM containing 10% FCS and G418 selection (1.5 mg/ml), and the cells diluted (between 1 in 4 and 1 in 20) (approximately 0.5 to 1.5×10⁶ cells per plate) in the same medium into micro-titre wells (150 μl per well; 2 or more plates per dilution). The micro-titre plates were incubated for at least two weeks at 37° C. in a CO$_2$ incubator and then checked regularly for viable clone formation.

Media from wells containing single viable clones was taken for testing and replaced with fresh media (containing G418). The removed media was tested for antibody binding to CEA in an ELISA (in the same manner as described in International Patent application Number WO 96/2001 1 Reference Example 5 part 1, except that the secondary antibody solution was changed from anti-mouse to anti-human (goat anti-human Kappa light chain peroxidase conjugate, Sigma A7164). Positive samples for the CEA ELISA were also tested for [A248S,G251T,D253K]HCPB enzyme activity (as described above) following activation (removal of the pro domain from the fusion protein) by trypsin (700 μg/ml in 50 mM Tris-HCl and 150 mM NaCl pH 7.6 at 4° C. for 1 hour, the reaction being stopped by the addition of a five fold excess of soy bean trypsin inhibitor). A number of clones were identified which produced media that was positive for both 806.077 antibody binding to CEA and [A248S,G251T,D253K]HCPB enzyme activity. These were further tested by non-reducing Western blot analysis (in the same manner as described in International Patent Application Number WO 96/20011 Reference Example 5 part j, except that the antibody solution is changed from anti-mouse to anti-human (goat anti-human Kappa light chain peroxidase conjugate, Sigma A7164) to identify clones which produce predominately F(ab')$_2$(806.077) fusion protein. These clones were then expanded, tested for stable generation of the fusion protein over a number of generations, and the highest producers bulked up and stored frozen in liquid nitrogen using standard technology.

Amplification, high-level expression and fermentation of fusion proteins from NS0 myeloma cells was performed in a similar manner to that described by Bebbington et al. (1992) in Bio/Technology 10, 169–175. Fusion protein was purified, and the pro-sequence removed as described in Example 102.

EXAMPLES 76 TO 101

Cloning and Expression of Other Variants of Pro-HCPB-Linker-(Humanised 806.077)Fd+(Humanised 806.077) Light Chain The method for the generation of fusion proteins with other mutants of HPCB was similar to that detailed in Example 75 (above), with the exception that in part b. of Example 75 there was a substitution of [D253K]HCPB or [G251T,D253K]HCPB for [A248S,G251T,D253K]HCPB and the plasmid DNA used in the PCR reaction was pICI1713 (as described in International Patent application Number WO 96/20011, Example 15) or pZEN1860 (Reference Example 1) respectively. After cloning, identification, and sequence confirmation the resulting plasmid containing pre-pro-[D253K]HCPB-linker or pre-pro-[G251T,D253K]HCPB-linker and humanised 806.077 VH gene up to the PstI site (at amino acid 5) in the pUC19 vector back ground was used in place of pCF004 in the subsequent cloning reactions.

The method for generation of fusion proteins with other CH1 domains was similar to that detailed in Example 75 (above), with the exception that in part c. of Example 75 there was a substitution of plasmids containing either humanised 806.077 VH version 1 with human IgG1 or IgG2 CH1 and hinge regions in place of 806.077-HuVH1-IgG3CH1' (SEQ ID NOs: 96 and 56 respectively). After cloning, identification, and sequence confirmation the resulting plasmid containing the IgG1 or IgG2 sequence was used in place of pCF005 in the subsequent cloning reactions.

The method for generation of fusion proteins with other variants of the humanised 806.077 light chain was similar to that detailed in Example 75 (above), with the exception that in part f. of Example 75 there was a substitution of plasmids containing either humanised 806.077 Lc version 1 or version 3 in place of 806.077-HuVK4-HuCK (SEQ ID NOs: 51 and 96 respectively). After cloning, identification, and sequence confirmation the resulting plasmid containing the alternative light chain sequence was used in place of pCF008/4 in the subsequent cloning reactions. The fusion protein variants for each Example (76 to 101) are shown in the following table.

TABLE

| Example No. | Humanised Heavy chain | Humanised Light chain | Mutant HCPB Enzyme |
|---|---|---|---|
| 76 | HuVH1-HuIgG3 | HuVK4-HuCK | [D253K]HCPB |
| 77 | HuVH1-HuIgG3 | HuVK4-HuCK | [G25IT,D253K]HCPB |
| 78 | HuVH1-HuIgG3 | HuVK1-HuCK | [A248S,G251T,D253K]HCPB |
| 79 | HuVH1-HuIgG3 | HuVK1-HuCK | [D253K]HCPB |
| 80 | HuVH1-HuIgG3 | HuVK1-HuCK | [G251T,D253K]HCPB |
| 81 | HuVH1-HuIgG3 | HuVK3-HuCK | [A248S,G251T,D253K]HCPB |
| 82 | HuVH1-HuIgG3 | HuVK3-HuCK | [D253K]HCPB |
| 83 | HuVH1-HuIgG3 | HuVK3-HuCK | [G251T,D253K]HCPB |
| 84 | HuVH1-HuIgG1 | HuVK4-HuCK | [A248S,G251T,D253K]HCPB |
| 85 | HuVH1-HuIgG1 | HuVK4-HuCK | [D253K]HCPB |
| 86 | HuVH1-HuIgG1 | HuVK4-HuCK | [G251T,D253K]HCPB |
| 87 | HuVH1-HuIgG1 | HuVK1-HuCK | [A248S,G251T,D253K]HCPB |
| 88 | HuVH1-HuIgG1 | HuVK1-HuCK | [D253K]HCPB |
| 89 | HuVH1-HuIgG1 | HuVK1-HuCK | [G25IT,D253K]HCPB |
| 90 | HuVH1-HuIgG1 | HuVK3-HuCK | [A248S,G251T,D253K]HCPB |
| 91 | HuVH1-HuIgG1 | HuVK3-HuCK | [D253K]HCPB |
| 92 | HuVH1-HuIgG1 | HuVK3-HuCK | [G251T,D253K]HCPB |
| 93 | HuVH1-HuIgG2 | HuVK4-HuCK | [A248S,G251T,D253K]HGPB |
| 94 | HuVH1-HuIgG2 | HuVK4-HuCK | [D253K]HCPB |
| 95 | HuVH1-HuIgG2 | HuVK4-HuCK | [G251T,D253K]HCPB |
| 96 | HuVH1-HuIgG2 | HuVK1-HuCK | [A248S,G251T,D253K]HCPB |
| 97 | HuVH1-HuIgG2 | HuVK1-HuCK | [D253K]HCPB |
| 98 | HuVH1-HuIgG2 | HuVK1-HuCK | [G25IT,D253K]HCPB |
| 99 | HuVH1-HuIgG2 | HuVK3-HuCK | [A248S,G251T,D253K]HCPB |
| 100 | HuVH1-HuIgG2 | HuVK3-HuCK | [D253K]HCPB |
| 101 | HuVH1-HuIgG2 | HuVK3-HuCK | [G251T,D253K]HCPB |

EXAMPLE 102

Purification of Proteins Containing 806.077 Antibody Sequences

Purification or enrichment of recombinant F(ab')$_2$ or antibody-enzyme fusion proteins may be achieved from myeloma cell, CHO cell or COS cell supernatants by several methods, used either singly or together. Purification of murine 806.077 F(ab')$_2$, chimeric 806.077 F(ab')$_2$ constructs and fully humanised 806.077 F(ab')$_2$ constructs, and antibody-enzyme fusion protein constructs incorporating these F(ab')$_2$ constructs were achieved by one or more of several different methods, affinity chromatography or anion exchange chromatography, or protein A/protein G chromatography. These techniques can also be applied to purification of 806.077 antibody—B7 fusions (see Example 104).

a) Antigen Affinity Chromatography

Carcinoembryonic antigen (CEA), to which the parent murine 806.077 antibody was raised, was immobilised on a column (using Pharmacia products). In brief, immobilisation was via a stable ester bond to Sepharose™ High Performance medium, NHS-activated prepacked in columns (HiTrap™); coupling of the CEA to the activated matrix was performed following the standard instructions provided with the product.

Preparation of a 1 ml Affinity Column.

CEA stock solution (8 mg/ml) was first diluted with coupling buffer (0.2M sodium hydrogen carbonate, 0.5M sodium chloride; pH8.3) to a final concentration of 0.5 mg/ml. A new column was washed with 6 ml of ice-cold 1 mM HCl at a flow rate not exceeding 1 ml/min. Immediately after, the CEA ligand (1 ml at 0.5 mg/ml) was injected onto the column. The column was sealed at both ends and left to stand for 30 minutes at room temperature. Excess active groups that had not coupled to the ligand were deactivated and any non-specifically bound ligand was washed out of the column by three rounds of alternating high and low pH washes. The buffers used were 0.5M ethanolamine, 0.5M sodium chloride (pH8.3) and 0.1M sodium acetate, 0.5M sodium chloride (pH 4.0). In each round of washes 6 ml of each buffer was washed over the column matrix. Finally, the column was washed into storage buffer (0.05M Na$_2$HPO$_4$, 0.1% NaN$_3$, pH7.0).

Purification Procedure

The cell culture supernatant containing the desired F(ab')$_2$ or fusion construct e.g. chimeric 806.077 F(ab')$_2$, humanised 806.077 F(ab')$_2$, or antibody-enzyme fusion protein was diluted 1:1 with phosphate buffered saline (pH 7.2) and passed over the 1 ml affinity column at a flow rate of 1 m/min. The column had previously been equilibrated with phosphate buffered saline (pH7.2; 50 mM sodium phoshate, 150 mM sodium chloride). The column was washed with 10 column volumes of phosphate buffered saline after the cell supernatant had passed over it. Bound F(ab')$_2$ was eluted with 5 column volumes of 100 mM sodium citrate (pH3.0), with 1 ml fractions of the eluant being collected. Detection of the eluted F(ab')$_2$ was achieved by Western blot analysis using a suitable antibody peroxidase conjugate (an anti-human Kappa Light chain-peroxidase conjugate in the case of the fully humanised F(ab')$_2$, Sigma A-7164) and developing with hydrogen peroxide and 4-chloro-1-naphthol. Appropriate fractions were pooled and concentrated, using a centrifugal concentrator (Centricon™ 30), where necessary.

b) Anion Exchange Chromatography

Cell culture supernatant containing the required F(ab')$_2$ or fusion construct e.g. chimeric 806.077 F(ab')$_2$, humanised 806.077 F(ab')$_2$, or antibody-enzyme fusion protein was diafiltered into 50 mM Tris (using a stirred cell with a 10,000 molecular weight cut-off membrane) until the ionic strength of the solution was equivilant to the column equilibration buffer. The 40 ml aliquot of the diafiltered supernatant was loaded on to a suitable column (Pharmacia Mono Q™ 10/10 HR) at 2 ml/min. The column was previously equilibrated with 50 mM Tris (pH8.0). Once the supernatant had passed over the column, the column was washed back to baseline with the equilibration buffer. Bound material on the column was then eluted with a 0–50% buffer B (50 mM Tris, 1M sodium chloride pH8.0 ) over 15 column volumes. Elution fractions were collected (4 ml per fraction) and those containing the F(ab')$_2$ were identified by Western blot analysis using a suitable antibody peroxidase conjugate (an anti-human Kappa Light chain -peroxidase conjugate in the case of the fully humanised F(ab')$_2$, Sigma A-7164) and developing with hydrogen peroxide and 4-chloro-1-naphthol. Appropriate fractions were pooled and concentrated using a centrifugal concentrator (Centricon™ 30), where necessary.

c) Protein A and Protein G Purification

The cell culture supernatant containing the desired F(ab')$_2$ or fusion construct (e.g. 806.077 F(ab')$_2$, chimeric 806.077 IgG$_1$ or IgG$_2$ or IgG$_3$; pro-HCPB-linker-806.077 F(ab')$_2$ ,806.077 F(ab')$_2$-HCPB) was diluted 1:1 with phosphate buffered saline before being loaded on to a column previously equilibrated in phosphate buffered saline (pH7.2). The column was washed with phosphate buffered saline, back to baseline, before the bound F(ab')$_2$ or fusion protein was eluted with 100 mM sodium citrate (pH 3.0) in the case of the F(ab')$_2$ and 50 mM glycine, 100 mM sodium chloride (pH10.8) in the case of the fusion proteins. Elution fractions were collected and neutralised by the addition of 125 µl 2M Tris per 1 ml of elution volume. Those fractions containing the F(ab')$_2$ were pooled and concentrated where necessary using a centrifugal concentrator.

d) Pro-Sequence Cleavage.

For fusion proteins containing a covalently linked pro-sequence e.g.(Pro-HCPB-linker-806.077 F(ab')$_2$) the pro sequence was cleaved by incubation the fusion with trypsin. This procedure at a milligram (of fusion) scale involved the following. Trypsin was mixed with the fusion protein in a ratio of 1:1000 (trypsin:fusion). The mixture was incubated for 24 hours at room temperature (around 22° C.), after which the cleavage of the pro sequence was complete. The fusion protein was separated from the pro sequence by recirculating the mixture in one of the generic chromatography purification or enrichment protocols.

EXAMPLE 103

Assay of Activity of Antibody-Enzyme Fusion Proteins Containing Mutant Human CPB Against Hipp-Glu Prodrug Analogues Cell culture supernatants or purified antibody-enzyme fusion proteins containing mutants of human CPB (D253K; G252T,D253K; A248S,G251T,D253K: Examples 48–101) are assayed for their ability to convert hippuryl-L-glutamic acid (Hipp-Glu; Reference Example 9 in International Patent Application Number WO 96/20011)) to hippuric acid using a HPLC based assay.

The reaction mixture (250 µl) contains either 4 µg of purified fusion protein or cell culture supernatant (used either neat or diluted with 0.025M Tris-HCl pH7.5; 125 µl) and 0.5 mM Hipp-Glu in 0.025 M Tris-HCL, pH 7.5. Samples are incubated for 5 hr at 37° C. The reactions are terminated by the addition of 250 µl of 30% methanol, 70% phosphate buffer (50 mM; pH 6.5), 0.2% trifluoroacetic acid and the amount of hippuric acid generated is quantified by HPLC (using a Hewlett Packard 1090 Series 11 with diode array system).

Samples (50 µl) are injected onto a column (25 cm; HICHROM™ Hi-RPB) and separated using a mobile phase of 15% methanol, 85% phosphate buffer (50 mM; pH 6.5) at a flow rate of 1 ml/min. The amount of product (hippuric acid) produced is determined from calibration curves generated with known amounts of hippuric acid (Sigma-H6375). Results are expressed as the percentage conversion of substrate into product at 37° C. at times ranging from 30 min-24 h depending on rate of conversion.

For antibody-enzyme fusion proteins with an N-terminal proCPB, the pro domain is first removed by treatment with trypsin (700 µg/ml) in 50 mM Tris-HCl (pH7.6), 150 mM NaCl at 4° C. for 1 h.

EXAMPLE 104

Preparation of a Human B7.1-Humanised 806.077 F(ab')$_2$ Fusion Protein (hB7-806)

As in Reference Example 3, a fusion protein consisting of the signal sequence and extracellular domain of human B7.1 fused directly to the 5' coding region of the humanised 806.077 antibody Fd chain is constructed using PCR techniques. A HindIII-NheI fragment is created containing the natural signal sequence and extracellular domain of human B7.1 fused to the VH region of a humanised 806.077 antibody heavy chain. This is cloned into a suitable vector, for example pNG4-V$_H$ss-HuIgG2CH1' or pNG4-V$_H$ss-HuIgG3CH1' (see Examples 39–47) (replacing bases 1423 in Seq.ID NO: 18), to create a human B7.1-humanised 806.077 Fd fusion gene. Co-expression of this fusion with a humanised 806.077 L chain (a suitable vector containing the VK4 version of humanised 806.077 light chain is pCF008/4; see Example 75) is then achieved after construction of a co-expression vector using expression systems such as those described herein. Such a vector is used to transfect NSO myeloma cells and colonies selected on the presence of CEA binding activity in the culture supernatant. Other humanised sequences are described in Examples 39–47.

The hB7-806 fusion protein is expressed from a suitable cell line and purified using protein-A column as described in Reference Example 3 or one of the methods described in Example 102. It should be noted that purification methods other than protein-A columns are preferred for humanised 806.077 antibody fragments and fusion proteins thereof. The fusion protein can be tested for both antigen and receptor binding properties and T-cell co-stimulatory activity when bound to LS174T cells using assays set out in Reference Example 3.

EXAMPLE 105

Preparation of Chimeric and Humanised 806.077 F(ab')$_2$-CPG2 Conjugates

The procedure described in Example 5 was repeated with the murine F(ab')$_2$ protein replaced by one of the chimeric versions described in Example 8 or one of the humanised versions described in Examples 39–47.

EXAMPLE 106

Preparation of Humanised 806.077 Fab-CPG2 Enzyme Fusion Protein.

Humanised 806.077 antibody and bacterial CPG2 enzyme fusion protein constructs are constructed using PCR methodology similar to that described for the construction of HuVK4 in Examples 12–38, in which specifically designed primers are used in a PCR reaction to amplify the antibody and enzyme gene components (such that the resulting DNA products contain overlapping complementary sequence) which are then joined via a further "splicing/joining" PCR reaction to make the complete antibody-enzyme fusion gene. The fusion protein is created by joining the 3' end of Fd humanised 806.077 antibody heavy chain gene to the 5' end of the CPG2 structural coding gene to create a Fab-CPG2 fusion protein coding gene. In such a construct, the humanised 806.077 antibody heavy chain gene component may be terminated after residue K236 for the HuVH1-HuIgG1 Fd heavy chain (SEQ ID NO: 93), after residue Val 237 for the HuVH1-HuIgG2 Fd heavy chain (SEQ ID NO: 57) or after residue Val 237 heavy chain in the HuVH1-HuIgG3 Fd heavy chain (SEQ ID NO: 95) (thus, in each case, excluding any sequence pertaining to the hinge region)

and may be joined to the first CPG2 residue positioned C-terminal to the signal sequence cleavage site (Minton et al (1984) Gene 31, 31–38). However, in order to obtain optimal antibody binding and enzymatic properties, it is also envisaged that it may be desirable to incorporate additional residues at the junction between the two constituent components.

The fusion gene is then cloned into a suitable vector, for example pNG4-VHss-HuIgG2CH1' (NCIMB no. 40797), after the appropriate restiction enzyme digestion, isolation of the vector and fusion gene DNA fragment have been made thus replacing the original antibody gene with that of the fusion protein. Co-expression of the fusion with a humanised 806.077 light chain is then achieved after construction of a co-expression vector in a manner analogous to that described in Example 11. The co-expression vector is used to transfect NSO myeloma cells and colonies selected on the presence of CEA and Fd binding activity in the culture supernatant as previously described. The fusion protein can be purified using a Protein-A column and shown to have both antigen and enzymatic properties using standard test methodology.

EXAMPLE 107
Further Combination of Humanised Heavy and Light Chain Variable Regions Based on Light Chain Sequence VK4

The procedures described in Examples 12–38 are repeated with the humanised light chain variable sequence of VK4 (SEQ ID NO: 71) replaced by the modified sequence in which the tyrosine residue (Tyr) at position 35 of SEQ ID NO: 71 is replaced by a phenylalanine residue.(Phe).

EXAMPLE 108
Further Combination of Humanised Heavy and Light Chain Variable Regions Based on Light Chain Sequence VK4

The procedures described in Examples 12–38 are repeated with the humanised light chain variable sequence of VK4 (SEQ ID NO: 71) replaced by the modified sequence in which the phenylalanine residue (Phe at position 72 of SEQ ID NO: 71 is replaced by a leucine residue (Leu).

EXAMPLE 109
Further Combination of Humanised Heavy and Light Chain Variable Regions Based on Light Chain Sequence VK4

The procedures described in Examples 12–38 are repeated with the humanised light chain variable sequence of VK4 (SEQ ID NO: 71) replaced by the modified sequence in which the tyrosine residue (Tyr) at position 35 and the phenylalanine residue (Phe) at position 72 of SEQ ID NO: 71 are replaced by a phenylalanine residue (Phe) and a leucine residue (Leu) respectively.

EXAMPLE 110
Combination of Humanised Heavy Chain Variable Regions and a Chimeric Light Chain Sequence The procedures described in Examples 12–38 are repeated with the humanised light chain variable sequence of replaced by the chimeric sequence of SEQ ID NO: 17 described in Example 8.

EXAMPLE 111–113
Expression of Humanised F(ab')2 Fragments with a Modified Light Chain VK4 Variable Sequence The procedures described in Examples 39–47 are repeated with the variable light chain sequence described in Example 107 used to make a replacement for the humanised light chain sequence of SEQ ID NO: 99 in which the tyrosine residue (Tyr) at position 57 of SEQ ID NO: 99 is replaced by a phenylalanine residue (Phe).

Example 111 is the combination of HuVH1-HuIgG1 and the modified SEQ ID NO: 99 described above.

Example 112 is the combination of HuVH1-HuIgG2 and the modified SEQ ID NO: 99 described above.

Example 113 is the combination of HuVH1-HuIgG3 and the modified SEQ ID NO: 99 described above.

EXAMPLE 114–116
Expression of Humanised F(ab')$_2$ Fragments with a Modified Light Chain VK4 Variable Sequence The procedures described in Examples 39–47 are repeated with the variable light chain sequence described in Example 108 used to make a replacement for the humanised light chain sequence of SEQ ID NO: 99 in which the phenylalanine residue (Phe) at position 94 of SEQ ID NO: 99 is replaced by a leucine residue (Leu).

Example 114 is the combination of HuVH1-HuIgG1 and the modified SEQ ID NO: 99 described above.

Example 115 is the combination of HuVH1-HuIgG2 and the modified SEQ ID NO: 99 described above.

Example 116 is the combination of HuVH1-HuIgG3 and the modified SEQ ID NO: 99 described above.

EXAMPLE 117–119
Expression of Humanised F(ab')$_2$ Fragments with a Modified Light Chain VK4 Variable Sequence The procedures described in Examples 39–47 are repeated with the variable light chain sequence described in Example 109 used to make a replacement for the humanised light chain sequence of SEQ ID NO: 99 in which the tyrosine residue (Tyr) at position 57 and the phenylalanine residue (Phe) at position 94 of SEQ ID NO: 99 is replaced by a phenylalanine residue (Phe) and leucine residue (Leu) respectively.

Example 117 is the combination of HuVH1-HuIgG1 and the modified SEQ ID NO: 99 described above.

Example 118 is the combination of HuVH1-HuIgG2 and the modified SEQ ID NO: 99 described above.

Example 119 is the combination of HuVH1-HuIgG3 and the 99 modified SEQ ID NO: described above.

EXAMPLE 120–122
Expression of Humanised F(ab')$_2$ Fragments with a Chimeric Light Chain Sequence The procedures described in Examples 39–47 are repeated with the chimeric light chain sequence described in Example 110 replacing the humanised light chain sequences used in Examples 39–47.

Example 120 is the combination of HuVH1-HuIgG1 and the chimeric light chain sequence described above.

Example 121 is the combination of HuVH1-HuIgG2 and the chimeric light chain sequence described above.

Example 122 is the combination of HuVH1-HuIgG3 and the chimeric light chain sequence described above.

EXAMPLE 123
Preparation of Humanised Fusion Protein Based on Modified Light Chain VK4 Sequence The procedures described in Example 48 are repeated but with plasmid pEE14-806.077HuVK4-HuCK replaced by a plasmid containing the modified VK4 sequence of Examples 107 and 111 to 113.

EXAMPLE 124
Preparation of Humanised Fusion Protein Based on Modified Light Chain VK4 Sequence The procedures described in Example 48 are repeated but with plasmid pEE14-806.077HuVK4-HuCK replaced by a plasmid containing the modified VK4 sequence of Examples 108 and 114 to 116.

EXAMPLE 125
Preparation of Humanised Fusion Protein Based on Modified Light Chain VK4 Sequence The procedures described in Example 48 are repeated but with plasmid pEE14-806.077HuVK4-HuCK replaced by a plasmid containing the modified VK4 sequence of Examples 109 and 117 to 119.

EXAMPLE 126
Preparation of Humanised Fusion Protein Based on a Chimeric Light Chain VK4 Sequence The procedures described in Example 48 are repeated but with plasmid pEE14-806.077HuVK4-HuCK replaced by a plasmid containing the chimeric light chain sequence of Examples 110 and 120 to 122.

EXAMPLE 127
Preparation of Humanised Fusion Protein Based on Modified Light Chain VK4 Sequence The procedures described in Example 75 are repeated but with plasmid pCF008/4 replaced by a plasmid containing the modified VK4 sequence of Examples 107 and 111 to 113.

EXAMPLE 128
Preparation of Humanised Fusion Protein Based on Modified Light Chain VK4 Sequence The procedures described in Example 75 are repeated but with plasmid pCF008/4 replaced by a plasmid containing the modified VK4 sequence of Examples 108 and 114 to 116.

EXAMPLE 129
Preparation of Humanised Fusion Protein Based on Modified Light Chain VK4 Sequence The procedures described in Example 75 are repeated but with plasmid pCF008/4 replaced by a plasmid containing the modified VK4 sequence of Examples 109 and 117 to 119.

EXAMPLE 130
Preparation of Humanised Fusion Protein Based on a Chimeric Light Chain VK4 Sequence The procedures described in Example 75 are repeated but with plasmid pCF008/4 replaced by a plasmid containing the chimeric light chain sequence of Examples 110 and 120 to 122.

REFERENCE EXAMPLE 1
Preparation of Gene Sequence for [G251T,D253K]HCPB

The method of cloning [G251T,D253K]HCPB in *E.coli* was very similar to the method described in International Patent application Number WO 96/2001 1, Example 15. Again pICI266 was used as the cloning vector, but the starting material for PCR site directed mutagenesis was the [D253K]HCPB gene in plasmid p1CI1713 (as described in International Patent Application Number WO 96/20011 Example 15). However, in this case site directed mutagenesis was used during the PCR amplification of the gene to change the codon at amino acid position 251 in the mature gene from Glycine to Threonine (GGC to ACT), the G251T change. Also during the generation of this mutation a number of other mutations were generated at the same (G251) site by using a mixture of oligonucleotides with codon changes at G251. Individual mutant genes were identified following transformation and hybridisation by sequencing across the mutation site, prior to complete gene sequencing. In this example only the oligonucleotide for introducing the G251T mutation will be considered. Two PCR mixtures were prepared, in a manner similar to that described in International Patent application Number WO 96/20011 Example 15. In the first reaction primers were CAN 00402 (SEQ ID NO: 116) and CAN 00734 (SEQ ID NO: 117). In the second reaction primers were CAN 00284 (SEQ ID NO: 118) and CAN 01076 (SEQ ID NO: 119). In both reactions the starting DNA was pICI1713.

Aliquots of the two PCR reactions were analysed for DNA of the correct size (about 750 and 250 base pairs) and estimation of concentration by agarose gel electrophoresis, and found to contain predominantly bands of the correct size. Another PCR was then set up using each of the first two PCR products, with the two end primers {CAN 00402 (SEQ ID NO: 116) and CAN 00284 (SEQ ID NO: 118)}. An aliquot of the PCR product was analysed for DNA of the correct size (about 1000 base pairs) by agarose gel electrophoresis and found to contain predominantly a band of the correct size. The remainder of the product from the reaction mix was purified, the isolated DNA restriction digested with enzymes NcoI and EcoRI, and a band of the correct size (about 1000 base pairs) purified in a similar manner to that described in international Patent application Number WO 96/20011 Example 16.

pICI266 double stranded DNA was restriction digested with NcoI and EcoRI enzymes, and DNA of the correct size (about 5600 base pairs) was purified. Aliquots of both restricted and purified vector and insert DNA samples were checked for purity and concentration estimation using agarose gel electrophoresis compared with known standards. From these estimates ligation mixes were prepared to clone the HCPB gene into the pICI266 vector in a similar manner to that described in International Patent application Number WO 96/20011 Example 16.

Following the ligation reaction the DNA mixture was used to transform *E.coli* strain DH5α. colonies were picked and tested by hybridisation. A number of the clones were then taken for plasmid DNA preparation. and were sequenced over the region of PCR mutation in order to identify clones with the G251T change in a manner similar to that described in International Patent application Number WO 96/2001 1 Example 16. From the sequencing results a clone containing a plasmid with the required [G25T:D253K] HCPB gene sequence was selected, and the plasmid called pZEN1860.

REFERENCE EXAMPLE 2
Preparation of Gene Sequence for [A248S,G251T,D253K] HCPB The method of cloning [A248S,G251T,D253K]HCPB in *E.coli* was very similar to the method described in Reference Example 1. The starting material for the PCR site directed mutagenesis was the [G251T,D253K]HCPB gene in plasmid pZEN1860 (described in Reference Example 1) in place of pICI1713. However, in this case site directed mutagenesis was used during the PCR amplification of the gene to change the codon at amino acid position 248 in the mature gene from alanine to serine (GCT to TTC), the A248S change. Two PCR mixtures were prepared, in a manner similar to that described in Reference Examples 1. In the first reaction primers were CAN 00402 (SEQ ID NO: 116) and CAN 00720 (SEQ ID NO: 120). In the second reaction primers were CAN 00284 (SEQ ID NO: 118) and CAN 00726 (SEQ ID NO: 121). In both reactions the starting DNA was pZEN1860.

Methods of PCR, cloning, expression and identification were the same as for Reference Example 1. From the sequencing results a clone containing a plasmid with the required [A248S,G251T,D253K]HCPB gene sequence was selected, and the plasmid called pZEN1921.

REFERENCE EXAMPLE 3

Preparation and Characterisation of a Human B7.1-Murine A5B7 F(ab')₂ Fusion Protein (AB7)

Methods for the preparation, purification and characterisation of recombinant murine A5B7 F(ab')₂ antibody have been published (WO 96120011, Reference Example 5). The cDNA sequence for human B7.1 antigen (also called CD80) has been isolated and described (Freeman G. J et al, Journal of Immunology, 1989, 143, 2714–2722). In this Example "A17" refers to human B7.1-murine A5B7 F(ab')₂ fusion protein and "A5B7" refers to the anti-CEA antibody termed A5B7.

Using a PCR based strategy we isolated the natural signal sequence and extracellular domain of human B7.1 (encoding amino-acids 1–242) from cDNA prepared from cultured Raji cells (ATCC No. CCL 86) and fused it directly upstream from the mature 5' coding sequence of the murine A5B7 Fd fragment. This involved isolation of the B7.1 sequence with PCR primers 187/96 and 204/96 (SEQ ID NOS: 126 and 127) and a partial A5B7 Fd sequence with PCR primers 203/96 and 205/96 (SEQ ID NOS: 128 and 129). After purification of the PCR products they were mixed in approximately equimolar amounts and fused by PCR with primers 187/96 and 205/96. The resulting PCR product was purified, digested with HindIII and BstEII (New England Biolabs (UK) Ltd., Wilbury Way, Hitchin, SG4 0TY) and cloned into the HindIII-BstEII region of pAF1 using standard procedures to create the full length human B7.1-murine A5B7 Fd fusion. This fusion gene (SEQ ID NO: 130–131) was cloned as a EcoRI-HindIII fragment into the GS-system expression vector pEE6 (Celltech Biologics, Bath Road, Slough, SL1 4EN) according to the protocols described in WO 96/20011, Reference Example 5, to generate vector pAB7.1.

A BglII-SalI fragment containing the B7.1-A5B7 Fd expression cassette was then cloned between the BglII and SalI sites of the vector pAF6 previously described to generate a vector (pAB7.2) capable of co-expressing the fusion protein and the A5B7 L chain. The vector pAB7.2 was then used to transform NS0 myeloma cells and colonies selected on their ability to grow in the absence of glutamine. Cell lines expressing the fusion protein were identified by determination of CEA binding activity in the culture supernatant using the ELISA described. A cell line expressing suitable levels of fusion protein (1D4) was selected for purification and characterisation of the AB7 fusion protein.

Purification and Characterisation of the AB7 Fusion Protein

The secreted recombinant B7.1(35-242)-A5B7 F(ab)₂, AB7, material was purified from culture supernatant using a Protein-A agarose matrix such as for example Protein-A Sepharose 4 fast flow as manufactured by Pharmacia (Pharmacia Biotech, 23 Grosvenor Rd, St Albans, Herts, AL1 3AW). The matrix was washed with 2×8 matrix volumes of binding buffer (3M NaCl, 1.5M Glycine, pH 8.9). The culture supernatant containing AB7 was diluted 1:1 with the binding buffer. The washed matrix was added to the diluted culture supernatant (1 ml settled volume of matrix per 40 ml of diluted supernatant) and incubated at 4° C. for 2 hrs with moderate shaking. The matrix was spun down by centrifugation and approx. 75% of the supernatant carefully poured off. The matrix was then resuspended in the residual supernatant and the resulting slurry packed into a column. The column was washed with 5–6 column volumes of 150 mM NaCl, 10 mM NaH₂PO₄, pH7.4. The buffer was then changed to 100 mM NaCitrate pH2.8 and elution fractions collected. These fractions were titrated to approximately pH7.0 by the addition of 2M Tris buffer pH.8.5. The elution fractions were analysed by non-reducing SDS-PAGE and the peak AB7 fraction(s) retained as the product.

N-Terminal Sequencing

A sample of AB7 was run on reducing SDS-PAGE and blotted onto PVDF (polyvinylidene difluoride) membrane (equipment, gels, blotting membrane and methods from NOVEX, 4202 Sorrento Valley Blvd, San Diego, Calif. 92121, USA.). The protein bands were stained with Coomassie blue and the band at approximately 70 kDa (i.e. B7.1-Fd fusion) was N-terminally sequenced (Applied Biosystems, 494 Protein Sequencer (Perkin Elmer, ABI division, Kelvin close, Birchwood Science Park North, Warrington, WA3 7PB.) The sequence obtained matched the expected sequence for mature B7 (ie. after leader sequence cleavage from amino-acid 35 in SEQ.ID NO: 131, Val Ile His Val etc.).

BIAcore Analysis

Figure 3:
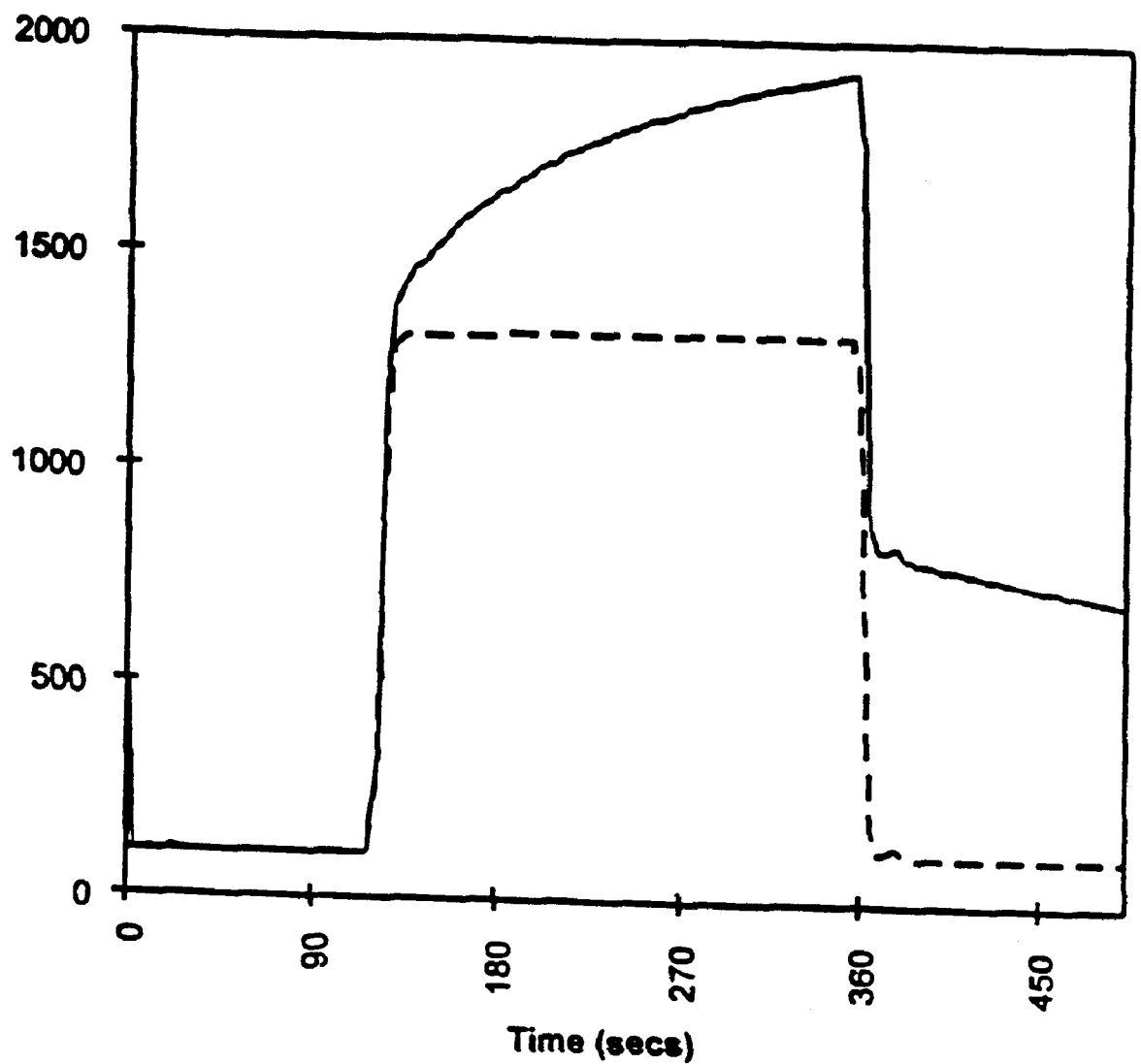
FIG. 3 shows BIAcore data showing antibody-B7.1 fusion protein binding to immobilised CTLA4-Ig in which the solid line represents test binding and the dotted line is a blank control; and unless otherwise stated.

AB7 was analysed using BIAcore surface plasmon resonance equipment made by Biacore (23 Grosvenor Rd, St. Albans, Herts., AL1 3AW, UK.) according to methods for BIAcore analysis of the CD80/CTLA-4 interaction taken from Greene J L, Leytze G M, Emswiler J, Peach R. Bajorath J, Cosand W, and Linsley P S. (1996) J. Biol. Chem. 271, 26762–26771. Samples of the purified AB7 product were injected over both a CTLA4-Ig amine coupled surface and a blank (control) amine coupled surface. Binding could clearly be seen to the CTLA4-Ig surface compared to the control surface (see FIG. 3). Binding could also be demonstrated between CTLA4-Ig and AB7 when the CTLA4-Ig was injected over an amine coupled AB7 surface.

Combined with the data from the anti-CEA ELISA these data confirm that the purified AB7 fusion protein has the biological properties of both component parts, namely antigen and receptor binding activities.

Co-Stimulatory Activity of the AB7 Fusion Protein

The ability of the AB7 fusion protein to provide a co-stimulatory signal to T cells when bound to CEA expressing tumour cells was tested using an adaptation of a co-stimulation assay format previously described (Jenkins et al. (1991) J. Immunol. 147:2461). CEA expressing LS174T colo-rectal tumour cells (fixed using 0.5% paraformaldehyde for 5 minutes at room temperature) were incubated with 10 μg/ml of the AB7 fusion protein (2 hours rotating at 4° C. in RPMI 1640 medium (Gibco. Life Technologies, Paisley, Scotland), containing 0.5% human serum (Sigma AB, Sigma Chemical Co, Dorset, UK.). The cells were washed twice prior to use and binding of the fusion protein confirmed using a fluoroscein isothiocyanate (FITC)—conjugated goat-anti-mouse Ig (Becton-Dickinson UK Ltd, Oxford) and flow cytometry (Facscan, Becton Dickinson). To allow the use of unprimed human T cells in the assay, the T cell receptor (TCR) stimulus was provided by an anti T cell receptor antibody (anti-CD3 antibody, OKT-3 Orthoclinical Diagnostics, Amersham, UK) previously coated onto the wells of a 96 well plate. OKT-3 was immobilised by incubating purified antibody (2 μg/ml in bicarbonate coating buffer, pH 9.6 (preformed capsule, Sigma)) overnight at 4° C. in 96 well flat bottomed microtitre plates (Costar Corporation, Cambridge, Mass., USA), which were then washed three to four times with PBS. Purified peripheral T cells (from negatively depleted (i.e. pulling out-components other than T cells) from donor human blood using magnetic beads (Dynabeads, Dynal A. S, Oslo, Norway) were added to the wells at 2×10⁵/well in 50 μl of RPMI 1640 medium containing 5% human serum. The fusion protein bound LS174T cells were added to the wells at 5×10⁴/well in 50 μl of RPMI 1640 medium plus 5% human serum. Finally the volume in all wells was made up to 200 μl using RPMI 1640 medium plus 5% human serum. Cultures were pulsed with 1.25 μCi of [³H] thymidine (Amersham International) after 48 hours and harvested 16 hours later with a semi-automated cell harvester (TomTec harvester, Wallac UK.). The incorporation of [³H] thymidine into DNA was quantitated using liquid scintillation counting (Betaplate Scint and Betaplate counter, Wallac UK.). Data from a typical costimulation assay is displayed in the Table below.

TABLE

Co-stimulation data

|  | αCD3 coated onto wells @ 2 μg/ml (cpm) |
|---|---|
| T cells alone | 3582 |
| T cells + αCD28 | 28178 |
| T cells + LS174T | 12303 |
| T cells + LS174T + αCD28 | 25759 |
| T cells + LS174T/fusion protein | 41755 |

αCD3 = anti-CD3 antibody; αCD28 = anti-CD28 antibody

Unprimed T-cells require both T-cell receptor and co-stimulatory signals. In the assay the T-cell receptor signal is provided by αCD3 antibody. Providing co-stimulation via αCD28 (Becton-Dickinson used at 0.6 μg/ml) stimulates uptake of [³H] thymidine over 8 fold compared to αCD3 alone. The presence of tumour cells has no significant effect on this stimulation. Providing the co-stimulatory signal by AB7 fusion protein bound to tumour cells stimulates uptake of [³H] thymidine by more than 3 fold over that given by tumour cells alone and over 11 fold higher than that seen in the absence of co-stimulation. The apparent stimulation provided by tumour cells alone may arise from residual accessory cells in the purified T-cell population. Similar increases in T cell proliferation were consistently observed in wells containing tumour cell bound fusion protein in each of 5 assays carried out compared with wells containing T cells and unbound tumour cells.

REFERENCE EXAMPLE 4
Preparation of IgG3-pBSIIKS+

This example describes the preparation of a vector containing a gene for the human IgG3 heavy chain constant and hinge region.

A gene containing the sequence shown in SEQ ID NO: 115 [this contains a sequence (residues 8 to 508) that is similar to SEQ ID NO: 25, but with residues 312 and 501 of SEQ ID NO: 25 changed to C and G respectively], was prepared by PCR by a method similar to that described by Jayaraman et al. (1991) Proc. Natl. Acad. Sci USA 88, 4084–4088.

The gene was made in two parts, known as IgG3A and IgG3B. These were cloned separately into the SacI and XmaI sites of pBluescript KS+(Stratagene Cloning Systems) to give vectors IgG3A-pBSIIKS+clone A7 and IgG3B-pBSIIKS+clone B17 respectively. IgG3A was made to extend past the PmaCI restriction site (CACGTG at positions 334–339 in SEQ ID NO: 115). Similarly, IgG3B was made such that the 5' end of the sequence was upstream of the PmaCI restriction site. To obtain the desired IgG3 gene sequence, the intermediate IgG3A and IgG3B vectors were cut with AflIII and PmaCI. The vector fragment (2823 bp) from IgG3A-pBSIIKS+clone A7, and insert fragment from IgG3B-pBSIIKS+clone B17 (666 bp) were isolated by electrophoresis in a 1% agarose gel and purified. The fragments were ligated and the ligation mix used to transform *E. coli* strain DH5α. Clones containing the required gene were identified by digestion of isolated DNA with SacI and XmaI to give a 520 bp fragment. The sequence of the insert was confirmed by DNA sequence analysis and clone number F3 was designated IgG3-pBSIIKS+.

What is claimed is:

1. An anti-CEA (carcinoembryonic antigen) antibody ("806.077 Ab") comprising complementarity determining regions (CDRs) in which the CDRs comprise the following sequences:

a) heavy chain
      CDR1 DNYMH (SEQ ID NO: 29)
      CDR2 WIDPENGDTE YAPKFRG (SEQ ID NO: 31)
      CDR3 LIYAGYLAMD Y(SEQ ID NO: 32); and
   b) light chain
      CDR1 SASSSVTYMH (SEQ ID NO: 26)
      CDR2 STSNLAS (SEQ ID NO: 27)
      CDR3 QQRSTYPLT (SEQ ID NO: 28).

2. An antibody according to claim 1 in which the heavy chain CDRs 1 and 3 are further defined as:
   CDR1 FNIKDNYMH (SEQ ID NO: 30); and
   CDR3 HVLIYAGYLA MDY (SEQ ID NO: 33).

3. An antibody according to claim 1 comprising the following sequence:

a heavy chain variable region sequence (SEQ ID NO: 11)
   EVQLQQSGAE LVRSGASVKL SCTASGFNIK DNYMHWVKQR 40
   PEQGLEWIAW IDPENGDTEY APKFRGKATL TADSSSNTAY 80
   LHLSSLTSED TAVYYCHVLI YAGYLAMDYW GQGTSVAVSS 120 and;

a light chain variable region sequence (SEQ ID NO: 9):
   DIELTQSPAI MSASPGEKVT ITCSASSSVT YMHWFQQKPG 40
   TSPKLWIYST SNLASGVPAR FSGSGSGTSY SLTISRMEAE 80
   DAATYYCQQR STYPLTFGAG TKLELKRA 108.

4. An antibody according to claim 3 which is in the form of a humanized antibody.

5. A humanised antibody according to claim 4, comprising at least one of the following sequences:
   a heavy chain variable region sequence which is VH1 (SEQ ID NO: 55);
   a light chain variable region sequence which is VK4 (SEQ ID NO: 71);
   a human CH1 heavy chain IgG3 constant region;
   a human kappa light chain CL region; and
   a human IgG3 hinge region.

6. Hybridoma 806.077 deposited as ECACC deposit no. 96022936.

7. A method of making an antibody as defined in claim 1, 2, 3, 5 or 4 which comprises:
   subjecting either a host cell transformed with a polynucleotide sequence capable of encoding a polypeptide of an antibody defined in claim 1, 2, 3, 5 or 4 or the hybridoma of claim 6, to conditions conducive to expression.

8. A humanized antibody according to claim 5 which is in the form of an F(ab')₂ fragment.

* * * * *